(12) United States Patent
Aburatani et al.

(10) Patent No.: US 9,079,957 B2
(45) Date of Patent: Jul. 14, 2015

(54) DIAGNOSIS AND TREATMENT OF CANCER USING ANTI-TMPRSS11E ANTIBODY

(75) Inventors: Hiroyuki Aburatani, Tokyo (JP); Shunpei Ishikawa, Tokyo (JP); Kiyotaka Nakano, Tokyo (JP)

(73) Assignees: THE UNIVERSITY OF TOKYO, Tokyo (JP); FORERUNNER PHARMA RESEARCH CO., LTD., Tokyo (JP)

( * ) Notice: Subject to any disclaimer, the term of this patent is extended or adjusted under 35 U.S.C. 154(b) by 758 days.

(21) Appl. No.: 13/138,880

(22) PCT Filed: Apr. 15, 2010

(86) PCT No.: PCT/JP2010/002750
§ 371 (c)(1),
(2), (4) Date: Dec. 20, 2011

(87) PCT Pub. No.: WO2010/119691
PCT Pub. Date: Oct. 21, 2010

(65) Prior Publication Data
US 2012/0128678 A1    May 24, 2012

(30) Foreign Application Priority Data
Apr. 16, 2009 (JP) ................. 2009-100163

(51) Int. Cl.
| A61K 39/395 | (2006.01) |
| C07K 16/28 | (2006.01) |
| C07K 16/30 | (2006.01) |
| C07K 16/40 | (2006.01) |
| G01N 33/574 | (2006.01) |
| A61K 39/00 | (2006.01) |

(52) U.S. Cl.
CPC .............. *C07K 16/28* (2013.01); *C07K 16/30* (2013.01); *C07K 16/40* (2013.01); *G01N 33/57423* (2013.01); *G01N 33/57442* (2013.01); *A61K 2039/505* (2013.01); *C07K 2316/96* (2013.01); *C07K 2317/24* (2013.01); *C07K 2317/565* (2013.01); *C07K 2317/72* (2013.01); *C07K 2317/732* (2013.01); *C07K 2317/76* (2013.01); *G01N 2333/96433* (2013.01)

(58) Field of Classification Search
None
See application file for complete search history.

(56) References Cited

U.S. PATENT DOCUMENTS

| 2003/0083462 A1 | 5/2003 | Baker et al. |
| 2010/0061933 A1 | 3/2010 | Kimura |
| 2010/0240872 A1 | 9/2010 | Nakano |

FOREIGN PATENT DOCUMENTS

| JP | 2002-509430 A | 3/2002 |
| JP | 2003-265183 A | 9/2003 |
| WO | 98-28426 A2 | 7/1998 |
| WO | 2008047925 | 4/2008 |
| WO | 2008-079352 A2 | 7/2008 |
| WO | 2009-004822 A1 | 1/2009 |

OTHER PUBLICATIONS

Viloria et al. (British Journal of Cancer, 2007, vol. 97, pp. 201-209).*
Office Action for Japanese Application No. 2011-509221 dated Sep. 2, 2014.
Kashyap et al., "Genomewide mRNA profiling of esophageal squamous cell carcinoma for identification of cancer biomarkers", Cancer Biology & Therapy, 8(1):1-11 (2009).
Communication for EP 10764278 dated Jul. 30, 2013, received Jul. 29, 2013 along with Supplementary European Search Report dated Jul. 19, 2013.
Lang, J.C., et al. Differential expression of a novel serine protease homologue in squamous cell carcinoma of the head and neck. IN: British Journal of Cancer; vol. 84(2); 2001; pp. 237-243.
Viloria, C.G., et al. Human DESC1 serine protease confers tumorigenic properties to MDCK cells and it is upregulated in tumours of different origin. IN: British Journal of Cancer; vol. 97; 2007; pp. 201-209.
Sedghizadeh, P.P., et al. Expression of the serine protease DESC1 correlates directly with normal keratinocyte differentiation and inversely with head and neck squamous cell carcinoma progression. IN: Head & Neck; vol. 28; May 2006; pp. 432-440.
International Search Report for PCT/JP2010/002750; Jun. 1, 2010.

* cited by examiner

*Primary Examiner* — Laura B Goddard
*Assistant Examiner* — Meera Natarajan
(74) *Attorney, Agent, or Firm* — Sughrue Mion, PLLC

(57) ABSTRACT

[Problem to be Solved]
An object of the present invention is to provide novel means for the treatment and diagnosis of cancer.
[Solution]
The present inventors have obtained a monoclonal antibody against TMPRSS11E and found that this antibody binds to a native form of TMPRSS11E, and TMPRSS11E is highly expressed on the cell membranes of cancer cell lines in flow cytometry. This antibody exhibits antibody-dependent cell-mediated cytotoxicity activity (ADCC activity) and antitumor effect based on internalization activity and is promising as a therapeutic target. Moreover, this antibody has neutralization activity against protease activity and is also expected to have effect brought about by the inhibition of TMPRSS11E functions.

14 Claims, 6 Drawing Sheets
(1 of 6 Drawing Sheet(s) Filed in Color)

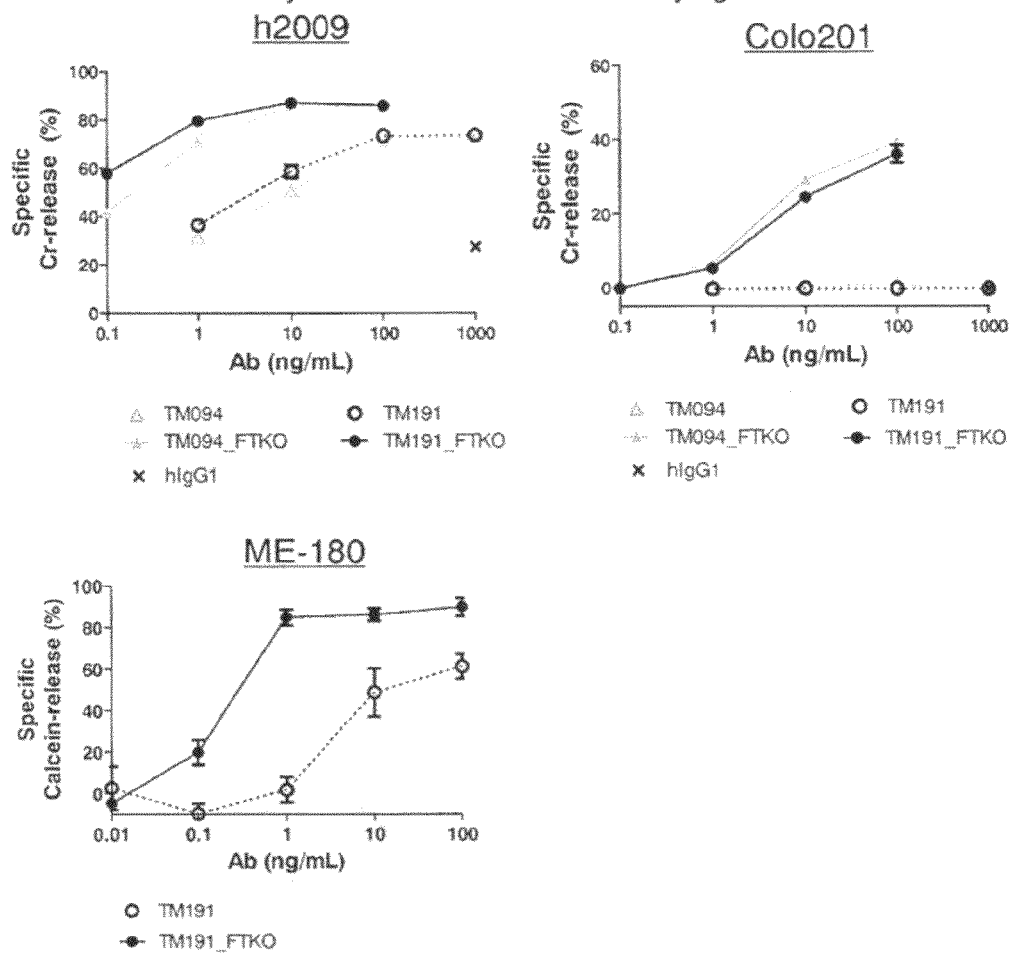
Fig.4 ADCC activity of anti-TMPRSS11E antibody against cancer cell lines
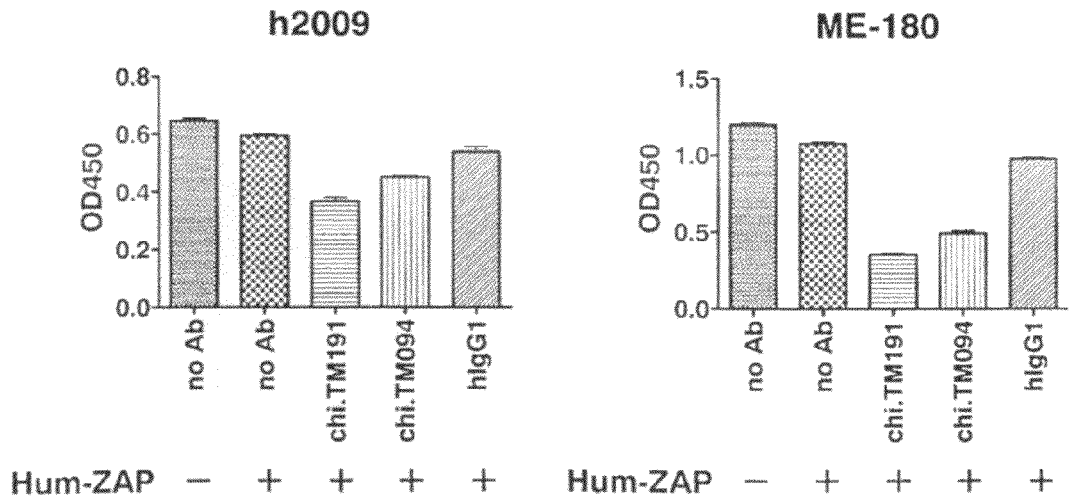
Fig.5 Antitumor effect of anti-TMPRSS11E antibody using Hum-ZAP Protease-neutralizing activity of anti-TMPRSS11E antibody Immunoblot analysis using anti-TMPRSS11E antibody Fig.8
Immunohistochemical analysis using anti-TMPRSS11E antibody
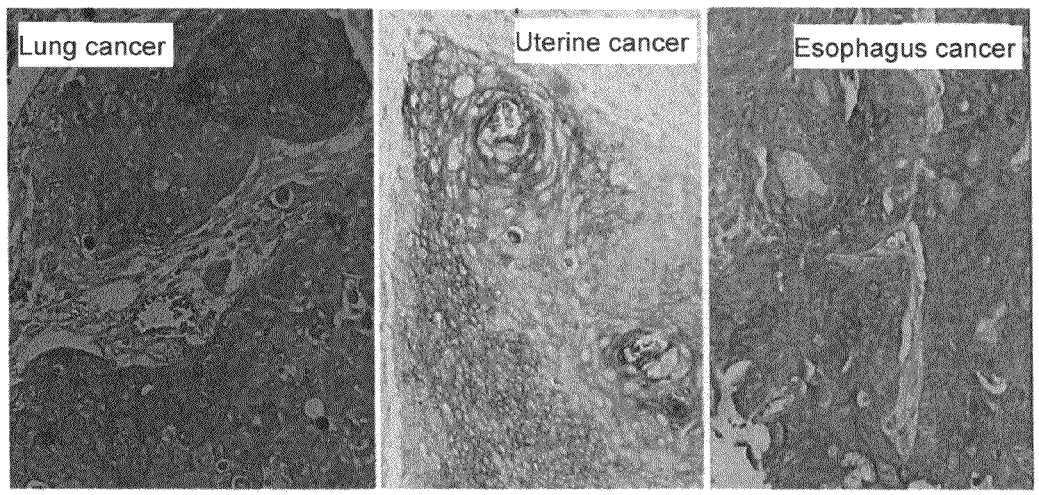
Fig.9
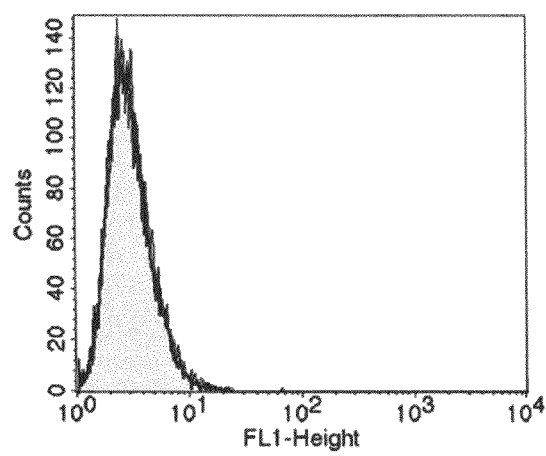
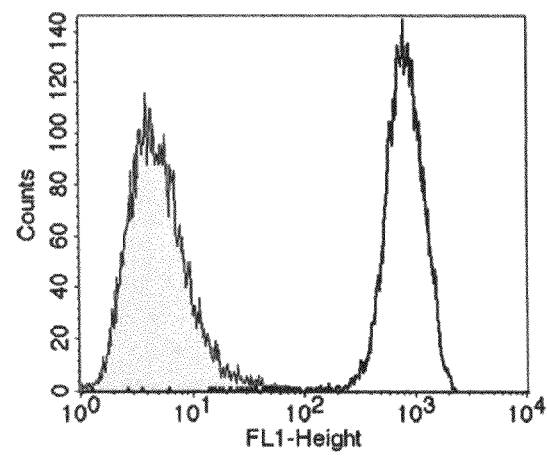

SEQUENCE LISTING

```
<160> NUMBER OF SEQ ID NOS: 60

<210> SEQ ID NO 1
<211> LENGTH: 1272
<212> TYPE: DNA
<213> ORGANISM: Homo Sapiens
<223> OTHER INFORMATION: TMPRSS11E

<400> SEQUENCE: 1
atgatgtatc ggccagatgt ggtgagggct aggaaaagag tttgttggga accctgggtt      60
atcggcctcg tcatcttcat atccctgatt gtcctggcag tgtgcattgg actcactgtt     120
cattatgtga gatataatca aaagaagacc tacaattact atagcacatt gtcatttaca     180
actgacaaac tatatgctga gtttggcaga gaggcttcta acaattttac agaaatgagc     240
```

-continued

```
cagagacttg aatcaatggt gaaaaatgca ttttataaat ctccattaag ggaagaattt    300
gtcaagtctc aggttatcaa gttcagtcaa cagaagcatg gagtgttggc tcatatgctg    360
ttgatttgta gatttcactc tactgaggat cctgaaactg tagataaaat tgttcaactt    420
gttttacatg aaaagctgca agatgctgta ggaccccta aagtagatcc tcactcagtt    480
aaaattaaaa aaatcaacaa gacagaaaca gacagctatc taaaccattg ctgcggaaca    540
cgaagaagta aaactctagg tcagagtctc aggatcgttg gtgggacaga agtagaagag    600
ggtgaatggc cctggcaggc tagcctgcag tgggatggga gtcatcgctg tggagcaacc    660
ttaattaatg ccacatggct tgtgagtgct gctcactgtt ttacaacata taagaaccct    720
gccagatgga ctgcttcctt tggagtaaca ataaaacctt cgaaaatgaa acggggtctc    780
cggagaataa ttgtccatga aaaatacaaa cacccatcac atgactatga tatttctctt    840
gcagagcttt ctagccctgt tccctacaca aatgcagtac atagagtttg tctccctgat    900
gcatcctatg agtttcaacc aggtgatgtg atgtttgtga caggatttgg agcactgaaa    960
aatgatggtt acagtcaaaa tcatcttcga caagcacagg tgactctcat agacgctaca   1020
acttgcaatg aacctcaagc ttacaatgac gccataactc ctagaatgtt atgtgctggc   1080
tccttagaag gaaaaacaga tgcatgccag ggtgactctg gaggaccact ggttagttca   1140
gatgctagag atatctggta ccttgctgga atagtgagct ggggagatga atgtgcgaaa   1200
cccaacaagc ctggtgttta tactagagtt acggccttgc gggactggat tacttcaaaa   1260
actggtatct aa                                                        1272
```

```
<210> SEQ ID NO 2
<211> LENGTH: 423
<212> TYPE: PRT
<213> ORGANISM: Homo Sapiens
<223> OTHER INFORMATION: TMPRSS11E

<400> SEQUENCE: 2
```

```
Met Met Tyr Arg Pro Asp Val Val Arg Ala Arg Lys Arg Val Cys Trp
1               5                   10                  15

Glu Pro Trp Val Ile Gly Leu Val Ile Phe Ile Ser Leu Ile Val Leu
            20                  25                  30

Ala Val Cys Ile Gly Leu Thr Val His Tyr Val Arg Tyr Asn Gln Lys
        35                  40                  45

Lys Thr Tyr Asn Tyr Tyr Ser Thr Leu Ser Phe Thr Thr Asp Lys Leu
    50                  55                  60

Tyr Ala Glu Phe Gly Arg Glu Ala Ser Asn Asn Phe Thr Glu Met Ser
65                  70                  75                  80

Gln Arg Leu Glu Ser Met Val Lys Asn Ala Phe Tyr Lys Ser Pro Leu
                85                  90                  95

Arg Glu Glu Phe Val Lys Ser Gln Val Ile Lys Phe Ser Gln Gln Lys
            100                 105                 110

His Gly Val Leu Ala His Met Leu Leu Ile Cys Arg Phe His Ser Thr
        115                 120                 125

Glu Asp Pro Glu Thr Val Asp Lys Ile Val Gln Leu Val Leu His Glu
    130                 135                 140

Lys Leu Gln Asp Ala Val Gly Pro Pro Lys Asp Pro His Ser Val
145                 150                 155                 160

Lys Ile Lys Lys Ile Asn Lys Thr Glu Thr Asp Ser Tyr Leu Asn His
                165                 170                 175

Cys Cys Gly Thr Arg Arg Ser Lys Thr Leu Gly Gln Ser Leu Arg Ile
```

```
            180                 185                 190
Val Gly Gly Thr Glu Val Glu Gly Glu Trp Pro Trp Gln Ala Ser
            195                 200                 205

Leu Gln Trp Asp Gly Ser His Arg Cys Gly Ala Thr Leu Ile Asn Ala
    210                 215                 220

Thr Trp Leu Val Ser Ala His Cys Phe Thr Tyr Lys Asn Pro
225                 230                 235                 240

Ala Arg Trp Thr Ala Ser Phe Gly Val Thr Ile Lys Pro Ser Lys Met
                    245                 250                 255

Lys Arg Gly Leu Arg Arg Ile Ile Val His Glu Lys Tyr Lys His Pro
            260                 265                 270

Ser His Asp Tyr Asp Ile Ser Leu Ala Glu Leu Ser Ser Pro Val Pro
        275                 280                 285

Tyr Thr Asn Ala Val His Arg Val Cys Leu Pro Asp Ala Ser Tyr Glu
    290                 295                 300

Phe Gln Pro Gly Asp Val Met Phe Val Thr Gly Phe Gly Ala Leu Lys
305                 310                 315                 320

Asn Asp Gly Tyr Ser Gln Asn His Leu Arg Gln Ala Gln Val Thr Leu
                    325                 330                 335

Ile Asp Ala Thr Thr Cys Asn Glu Pro Gln Ala Tyr Asn Asp Ala Ile
            340                 345                 350

Thr Pro Arg Met Leu Cys Ala Gly Ser Leu Gly Lys Thr Asp Ala
        355                 360                 365

Cys Gln Gly Asp Ser Gly Gly Pro Leu Val Ser Ser Asp Ala Arg Asp
    370                 375                 380

Ile Trp Tyr Leu Ala Gly Ile Val Ser Trp Gly Asp Glu Cys Ala Lys
385                 390                 395                 400

Pro Asn Lys Pro Gly Val Tyr Thr Arg Val Thr Ala Leu Arg Asp Trp
                    405                 410                 415

Ile Thr Ser Lys Thr Gly Ile
            420

<210> SEQ ID NO 3
<211> LENGTH: 5
<212> TYPE: PRT
<213> ORGANISM: Mus musculus
<223> OTHER INFORMATION: TM094 VH CDR1

<400> SEQUENCE: 3

Ser Tyr Ala Ile Ser
1               5

<210> SEQ ID NO 4
<211> LENGTH: 17
<212> TYPE: PRT
<213> ORGANISM: Mus musculus
<223> OTHER INFORMATION: TM094 VH CDR2

<400> SEQUENCE: 4

Glu Ile Tyr Pro Arg Asn Asn Asp Thr Tyr Tyr Asn Glu Lys Phe Lys
1               5                   10                  15

Gly

<210> SEQ ID NO 5
<211> LENGTH: 13
<212> TYPE: PRT
<213> ORGANISM: Mus musculus
<223> OTHER INFORMATION: TM094 VH CDR3
```

-continued

```
<400> SEQUENCE: 5

Glu Gly Asp Tyr Tyr Gly Asp Tyr Glu Gly Phe Ala Tyr
1               5                   10

<210> SEQ ID NO 6
<211> LENGTH: 5
<212> TYPE: PRT
<213> ORGANISM: Mus musculus
<223> OTHER INFORMATION: TM191 VH CDR1

<400> SEQUENCE: 6

Asp Tyr Gly Met Ala
1               5

<210> SEQ ID NO 7
<211> LENGTH: 17
<212> TYPE: PRT
<213> ORGANISM: Mus musculus
<223> OTHER INFORMATION: TM191 VH CDR2

<400> SEQUENCE: 7

Phe Ile Ser Asn Leu Ala Tyr Ser Ser Tyr Tyr Ala Asp Thr Val Thr
1               5                   10                  15

Gly

<210> SEQ ID NO 8
<211> LENGTH: 14
<212> TYPE: PRT
<213> ORGANISM: Mus musculus
<223> OTHER INFORMATION: TM191 VH CDR3

<400> SEQUENCE: 8

Arg Ile Phe Asp Tyr Asp Gly Asp Gly Pro Tyr Glu Asp Tyr
1               5                   10

<210> SEQ ID NO 9
<211> LENGTH: 5
<212> TYPE: PRT
<213> ORGANISM: Mus musculus
<223> OTHER INFORMATION: EA230 VH CDR1

<400> SEQUENCE: 9

Asn Tyr Trp Met Ser
1               5

<210> SEQ ID NO 10
<211> LENGTH: 19
<212> TYPE: PRT
<213> ORGANISM: Mus musculus
<223> OTHER INFORMATION: EA230 VH CDR2

<400> SEQUENCE: 10

Glu Val Arg Leu Lys Ser Asn Asn Tyr Val Thr His Tyr Ala Glu Ser
1               5                   10                  15

Val Lys Gly

<210> SEQ ID NO 11
<211> LENGTH: 3
<212> TYPE: PRT
<213> ORGANISM: Mus musculus
<223> OTHER INFORMATION: EA230 VH CDR3

<400> SEQUENCE: 11
```

Phe Ala Tyr
1

<210> SEQ ID NO 12
<211> LENGTH: 11
<212> TYPE: PRT
<213> ORGANISM: Mus musculus
<223> OTHER INFORMATION: TM094 VL CDR1

<400> SEQUENCE: 12

Arg Ala Ser Gln Asp Val Arg Asn Phe Leu Asn
1               5                   10

<210> SEQ ID NO 13
<211> LENGTH: 7
<212> TYPE: PRT
<213> ORGANISM: Mus musculus
<223> OTHER INFORMATION: TM094 VL CDR2

<400> SEQUENCE: 13

Tyr Thr Ser Arg Leu His Ser
1               5

<210> SEQ ID NO 14
<211> LENGTH: 9
<212> TYPE: PRT
<213> ORGANISM: Mus musculus
<223> OTHER INFORMATION: TM094 VL CDR3

<400> SEQUENCE: 14

Gln Gln Tyr Ser Asn Leu Pro Tyr Thr
1               5

<210> SEQ ID NO 15
<211> LENGTH: 12
<212> TYPE: PRT
<213> ORGANISM: Mus musculus
<223> OTHER INFORMATION: TM191 VL CDR1

<400> SEQUENCE: 15

Ser Ala Thr Ser Ser Val Ser Ser Arg Tyr Val His
1               5                   10

<210> SEQ ID NO 16
<211> LENGTH: 7
<212> TYPE: PRT
<213> ORGANISM: Mus musculus
<223> OTHER INFORMATION: TM191 VL CDR2

<400> SEQUENCE: 16

Gly Thr Ser Asn Leu Ala Ser
1               5

<210> SEQ ID NO 17
<211> LENGTH: 9
<212> TYPE: PRT
<213> ORGANISM: Mus musculus
<223> OTHER INFORMATION: TM191 VL CDR3

<400> SEQUENCE: 17

Gln Gln Tyr His Asn Asp Pro Pro Thr
1               5

<210> SEQ ID NO 18
<211> LENGTH: 12
<212> TYPE: PRT

```
<213> ORGANISM: Mus musculus
<223> OTHER INFORMATION: EA230 VL CDR1

<400> SEQUENCE: 18

Ser Ala Asn Ser Ser Val Ser Ser Tyr Leu Tyr
1               5                   10

<210> SEQ ID NO 19
<211> LENGTH: 7
<212> TYPE: PRT
<213> ORGANISM: Mus musculus
<223> OTHER INFORMATION: EA230 VL CDR2

<400> SEQUENCE: 19

Arg Thr Ser Lys Leu Ala Ser
1               5

<210> SEQ ID NO 20
<211> LENGTH: 9
<212> TYPE: PRT
<213> ORGANISM: Mus musculus
<223> OTHER INFORMATION: EA230 VL CDR3

<400> SEQUENCE: 20

His Gln Trp Asp Thr Tyr Pro Pro Thr
1               5

<210> SEQ ID NO 21
<211> LENGTH: 4
<212> TYPE: PRT
<213> ORGANISM: Artificial Sequence
<220> FEATURE:
<223> OTHER INFORMATION: peptide linker

<400> SEQUENCE: 21

Gly Gly Gly Ser
1

<210> SEQ ID NO 22
<211> LENGTH: 4
<212> TYPE: PRT
<213> ORGANISM: Artificial Sequence
<220> FEATURE:
<223> OTHER INFORMATION: peptide linker

<400> SEQUENCE: 22

Ser Gly Gly Gly
1

<210> SEQ ID NO 23
<211> LENGTH: 5
<212> TYPE: PRT
<213> ORGANISM: Artificial Sequence
<220> FEATURE:
<223> OTHER INFORMATION: peptide linker

<400> SEQUENCE: 23

Gly Gly Gly Gly Ser
1               5

<210> SEQ ID NO 24
<211> LENGTH: 5
<212> TYPE: PRT
<213> ORGANISM: Artificial Sequence
<220> FEATURE:
<223> OTHER INFORMATION: peptide linker
```

```
<400> SEQUENCE: 24

Ser Gly Gly Gly Gly
1               5

<210> SEQ ID NO 25
<211> LENGTH: 6
<212> TYPE: PRT
<213> ORGANISM: Artificial Sequence
<220> FEATURE:
<223> OTHER INFORMATION: peptide linker

<400> SEQUENCE: 25

Gly Gly Gly Gly Gly Ser
1               5

<210> SEQ ID NO 26
<211> LENGTH: 6
<212> TYPE: PRT
<213> ORGANISM: Artificial Sequence
<220> FEATURE:
<223> OTHER INFORMATION: peptide linker

<400> SEQUENCE: 26

Ser Gly Gly Gly Gly Gly
1               5

<210> SEQ ID NO 27
<211> LENGTH: 7
<212> TYPE: PRT
<213> ORGANISM: Artificial Sequence
<220> FEATURE:
<223> OTHER INFORMATION: peptide linker

<400> SEQUENCE: 27

Gly Gly Gly Gly Gly Gly Ser
1               5

<210> SEQ ID NO 28
<211> LENGTH: 7
<212> TYPE: PRT
<213> ORGANISM: Artificial Sequence
<220> FEATURE:
<223> OTHER INFORMATION: peptide linker

<400> SEQUENCE: 28

Ser Gly Gly Gly Gly Gly Gly
1               5

<210> SEQ ID NO 29
<211> LENGTH: 5
<212> TYPE: PRT
<213> ORGANISM: Artificial Sequence
<220> FEATURE:
<223> OTHER INFORMATION: peptide linker

<400> SEQUENCE: 29

Gly Gly Gly Gly Ser
1               5

<210> SEQ ID NO 30
<211> LENGTH: 5
<212> TYPE: PRT
<213> ORGANISM: Artificial Sequence
<220> FEATURE:
<223> OTHER INFORMATION: peptide linker

<400> SEQUENCE: 30
```

Ser Gly Gly Gly Gly
1               5

<210> SEQ ID NO 31
<211> LENGTH: 30
<212> TYPE: DNA
<213> ORGANISM: Artificial Sequence
<220> FEATURE:
<223> OTHER INFORMATION: primer TMPRSS11E

<400> SEQUENCE: 31
acctcaagct tacaatgacg ccataactcc                                        30

<210> SEQ ID NO 32
<211> LENGTH: 30
<212> TYPE: DNA
<213> ORGANISM: Artificial Sequence
<220> FEATURE:
<223> OTHER INFORMATION: primer TMPRSS11E

<400> SEQUENCE: 32
tgaagtaatc cagtcccgca aggccgtaac                                        30

<210> SEQ ID NO 33
<211> LENGTH: 1593
<212> TYPE: DNA
<213> ORGANISM: Artificial Sequence
<220> FEATURE:
<223> OTHER INFORMATION: construct sTMPRSS11Ep1_mIgG2aFc

<400> SEQUENCE: 33
gaattccacc atggttcttg ccagctctac caccagcatc acaccatgc tgctcctgct         60 cctgatgctg gcccagccgg ccatggcgtc agttaaaatt aaaaaaatca acaagacaga       120
aacagacagc tatctaaacc attgctgcgg aacacgaaga agtaaaactc taggtcagag       180
tctcaggatc gttggtggga cagaagtaga agagggtgaa tggccctggc aggctagcct       240
gcagtgggat gggagtcatc gctgtggagc aaccttaatt aatgccacat ggcttgtgag       300
tgctgctcac tgttttacaa catataagaa ccctgccaga tggactgctt cctttggagt       360
aacaataaaa ccttcgaaaa tgaaacgggg tctccggaga ataattgtcc atgaaaaata       420
caaacaccca tcacatgact atgatatttc tcttgcagag cttttctagcc ctgttcccta       480 cacaaatgca gtacatagag tttgtctccc tgatgcatcc tatgagtttc aaccaggtga       540
tgtgatgttt gtgacaggat ttggagcact gaaaaatgat ggttacagtc aaaatcatct       600
tcgacaagca caggtgactc tcatagacgc tacaacttgc aatgaacctc aagcttacaa       660
tgacgccata actcctagaa tgttatgtgc tggctcctta aaggaaaaaa cagatgcatg       720 ccaggggtgac tctggaggac cactggttag ttcagatgct agagatatct ggtaccttgc       780
tggaatagtg agctggggag atgaatgtgc gaaacccaac aagcctggtg tttatactag       840
agttacggcc ttgcgggact ggattacttc aaaaactggt atcgaacctc gcggaccgac       900
aatcaagccc tgtcctccat gcaaatgccc agcacctaac ctcttgggtg accatccgt       960 cttcatcttc cctccaaaga tcaaggatgt actcatgatc tccctgagcc ccatagtcac      1020
atgtgtggtg gtgatgtga gcgaggatga cccagatgtc cagatcagct ggtttgtgaa      1080
caacgtggaa gtacacacag ctcagacaca aacccataga gaggattaca acagtactct      1140
ccgggtggtc agtgccctcc ccatccagca ccaggactgg atgagtggca aggagttcaa      1200
atgcaaggtc aacaacaaag acctgccagc gcccatcgag agaaccatct caaaacccaa      1260

-continued

```
agggtcagta agagctccac aggtatatgt cttgcctcca ccagaagaag agatgactaa   1320
gaaacaggtc actctgacct gcatggtcac agacttcatg cctgaagaca tttacgtgga   1380
gtggaccaac aacgggaaaa cagagctaaa ctacaagaac actgaaccag tcctggactc   1440
tgatggttct tacttcatgt acagcaagct gagagtggaa aagaagaact gggtggaaag   1500
aaatagctac tcctgttcag tggtccacga gggtctgcac aatcaccaca cgactaagag   1560
cttctcccgg actccgggta atgagcggc cgc                                1593
```

<210> SEQ ID NO 34
<211> LENGTH: 524
<212> TYPE: PRT
<213> ORGANISM: Artificial Sequence
<220> FEATURE:
<223> OTHER INFORMATION: construct sTMPRSS11Ep1_mIgG2aFc

<400> SEQUENCE: 34

```
Met Val Leu Ala Ser Ser Thr Thr Ser Ile His Thr Met Leu Leu Leu
1               5                   10                  15

Leu Leu Met Leu Ala Gln Pro Ala Met Ala Ser Val Lys Ile Lys Lys
            20                  25                  30

Ile Asn Lys Thr Glu Thr Asp Ser Tyr Leu Asn His Cys Cys Gly Thr
        35                  40                  45

Arg Arg Ser Lys Thr Leu Gly Gln Ser Leu Arg Ile Val Gly Gly Thr
    50                  55                  60

Glu Val Glu Glu Gly Glu Trp Pro Trp Gln Ala Ser Leu Gln Trp Asp
65                  70                  75                  80

Gly Ser His Arg Cys Gly Ala Thr Leu Ile Asn Ala Thr Trp Leu Val
                85                  90                  95

Ser Ala Ala His Cys Phe Thr Thr Tyr Lys Asn Pro Ala Arg Trp Thr
            100                 105                 110

Ala Ser Phe Gly Val Thr Ile Lys Pro Ser Lys Met Lys Arg Gly Leu
        115                 120                 125

Arg Arg Ile Ile Val His Glu Lys Tyr Lys His Pro Ser His Asp Tyr
    130                 135                 140

Asp Ile Ser Leu Ala Glu Leu Ser Ser Pro Val Pro Tyr Thr Asn Ala
145                 150                 155                 160

Val His Arg Val Cys Leu Pro Asp Ala Ser Tyr Glu Phe Gln Pro Gly
                165                 170                 175

Asp Val Met Phe Val Thr Gly Phe Gly Ala Leu Lys Asn Asp Gly Tyr
            180                 185                 190

Ser Gln Asn His Leu Arg Gln Ala Gln Val Thr Leu Ile Asp Ala Thr
        195                 200                 205

Thr Cys Asn Glu Pro Gln Ala Tyr Asn Asp Ala Ile Thr Pro Arg Met
    210                 215                 220

Leu Cys Ala Gly Ser Leu Glu Gly Lys Thr Asp Ala Cys Gln Gly Asp
225                 230                 235                 240

Ser Gly Gly Pro Leu Val Ser Ser Asp Ala Arg Asp Ile Trp Tyr Leu
                245                 250                 255

Ala Gly Ile Val Ser Trp Gly Asp Glu Cys Ala Lys Pro Asn Lys Pro
            260                 265                 270

Gly Val Tyr Thr Arg Val Thr Ala Leu Arg Asp Trp Ile Thr Ser Lys
        275                 280                 285

Thr Gly Ile Glu Pro Arg Gly Pro Thr Ile Lys Pro Cys Pro Pro Cys
    290                 295                 300
```

Lys Cys Pro Ala Pro Asn Leu Leu Gly Gly Pro Ser Val Phe Ile Phe
305                 310                 315                 320

Pro Pro Lys Ile Lys Asp Val Leu Met Ile Ser Leu Ser Pro Ile Val
            325                 330                 335

Thr Cys Val Val Val Asp Val Ser Glu Asp Asp Pro Asp Val Gln Ile
        340                 345                 350

Ser Trp Phe Val Asn Asn Val Glu Val His Thr Ala Gln Thr Gln Thr
    355                 360                 365

His Arg Glu Asp Tyr Asn Ser Thr Leu Arg Val Val Ser Ala Leu Pro
370                 375                 380

Ile Gln His Gln Asp Trp Met Ser Gly Lys Glu Phe Lys Cys Lys Val
385                 390                 395                 400

Asn Asn Lys Asp Leu Pro Ala Pro Ile Glu Arg Thr Ile Ser Lys Pro
            405                 410                 415

Lys Gly Ser Val Arg Ala Pro Gln Val Tyr Val Leu Pro Pro Pro Glu
        420                 425                 430

Glu Glu Met Thr Lys Lys Gln Val Thr Leu Thr Cys Met Val Thr Asp
    435                 440                 445

Phe Met Pro Glu Asp Ile Tyr Val Glu Trp Thr Asn Asn Gly Lys Thr
450                 455                 460

Glu Leu Asn Tyr Lys Asn Thr Glu Pro Val Leu Asp Ser Asp Gly Ser
465                 470                 475                 480

Tyr Phe Met Tyr Ser Lys Leu Arg Val Glu Lys Lys Asn Trp Val Glu
            485                 490                 495

Arg Asn Ser Tyr Ser Cys Ser Val Val His Glu Gly Leu His Asn His
        500                 505                 510

His Thr Thr Lys Ser Phe Ser Arg Thr Pro Gly Lys
    515                 520

<210> SEQ ID NO 35
<211> LENGTH: 21
<212> TYPE: DNA
<213> ORGANISM: Artificial Sequence
<220> FEATURE:
<223> OTHER INFORMATION: oligonucleotide MHC-IgG1

<400> SEQUENCE: 35
gggccagtgg atagacagat g                                            21

<210> SEQ ID NO 36
<211> LENGTH: 23
<212> TYPE: DNA
<213> ORGANISM: Artificial Sequence
<220> FEATURE:
<223> OTHER INFORMATION: oligonucleotide kappa

<400> SEQUENCE: 36
gctcactgga tggtgggaag atg                                          23

<210> SEQ ID NO 37
<211> LENGTH: 423
<212> TYPE: DNA
<213> ORGANISM: Mus musculus
<223> OTHER INFORMATION: TM094 VH

<400> SEQUENCE: 37
atggaatgga tctggatctt tctcttcatc ctgtcaggaa ctgcaggtgt ccaattccag    60
gttcagctgc agcagtctgg agctgagctg gagaggcctg ggcttcagt gaagctgtcc   120

```
tgcaaggctt ctggctacac cttcacaagc tatgctataa gctgggtgaa gcagagaatc    180
ggacagggcc ttgagtggat tggagagatc tatcctagaa ataatgatac ttactacaat    240
gagaaattca agggcaaggc cacactgact gcagacaaat cctccagcac agcctacatg    300
cagctcagca gcctgacatc tgaggactct gcagtctatt tctgtgcaag agaaggggac    360
tactatggtg actacgaggg gtttgcttac tggggccaag gactctggt cgctgtctct    420 gca                                                                  423

<210> SEQ ID NO 38
<211> LENGTH: 141
<212> TYPE: PRT
<213> ORGANISM: Mus musculus
<223> OTHER INFORMATION: TM094 VH

<400> SEQUENCE: 38

Met Glu Trp Ile Trp Ile Phe Leu Phe Ile Leu Ser Gly Thr Ala Gly
1               5                   10                  15

Val Gln Phe Gln Val Gln Leu Gln Gln Ser Gly Ala Glu Leu Glu Arg
                20                  25                  30

Pro Gly Ala Ser Val Lys Leu Ser Cys Lys Ala Ser Gly Tyr Thr Phe
            35                  40                  45

Thr Ser Tyr Ala Ile Ser Trp Val Lys Gln Arg Ile Gly Gln Gly Leu
        50                  55                  60

Glu Trp Ile Gly Glu Ile Tyr Pro Arg Asn Asn Asp Thr Tyr Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Glu Gly Asp Tyr Tyr Gly Asp Tyr Glu Gly Phe
        115                 120                 125

Ala Tyr Trp Gly Gln Gly Thr Leu Val Ala Val Ser Ala
    130                 135                 140

<210> SEQ ID NO 39
<211> LENGTH: 381
<212> TYPE: DNA
<213> ORGANISM: Mus musculus
<223> OTHER INFORMATION: TM094 VL

<400> SEQUENCE: 39
atgatgtcct ctgctcagtt ccttggtctc ctgttgctct gttttcaagg taccagatgt    60
gatatccaga tgacacagac tacatcctcc ctgtctgcct ctctgggaga cagagtcacc    120
atcagttgca gggcaagtca ggatgttcgc aattttttaa actggtatca gcagaaacca    180
gatggaactg ttaaactcct gatctactac acatcaagat acactcagg agtcccatca     240 aggttcagtg gcagtgggtc tgggacagat tattctctca ccatcagcaa cctggaacct    300
gaagatattg ccacttacta ttgtcagcag tatagtaatc ttccgtatac gttcggatcg    360
gggaccaagt tggaaataaa a                                              381

<210> SEQ ID NO 40
<211> LENGTH: 127
<212> TYPE: PRT
<213> ORGANISM: Mus musculus
<223> OTHER INFORMATION: TM094 VL
```

<400> SEQUENCE: 40

Met Met Ser Ser Ala Gln Phe Leu Gly Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Val Arg Asn Phe Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Pro Glu Asp Ile Ala Thr Tyr Tyr Cys Gln Gln Tyr Ser
            100                 105                 110

Asn Leu Pro Tyr Thr Phe Gly Ser Gly Thr Lys Leu Glu Ile Lys
        115                 120                 125

<210> SEQ ID NO 41
<211> LENGTH: 426
<212> TYPE: DNA
<213> ORGANISM: Mus musculus
<223> OTHER INFORMATION: TM191 VH

<400> SEQUENCE: 41
atggacttca ggctcagctt acttattttt gtccttattt taaaaggtgt ccagtgtgag      60
gtgaagctgg tggagtctgg gggaggctta gtgaagcctg agggtccct gaaactctcc     120 tgtgcagcct ctggattcac tttcagtgac tacggaatgg cgtgggttcg acaggctcca     180
gggaaggggc ctgagtgggt agcattcatt agtaatttgg catatagtag ttattatgca     240
gacactgtga cgggccgatt caccatctct agagagaatg ccaagaacac cctgtacctg     300
gaaatgagca gtctgaggtc tgaggactca gccatgtatt actgtgcaag acgaatcttt     360
gattacgacg ggacggtcc ttatgaggat tactggggtc aaggaacctc agtcaccgtc     420
tcctca                                                                426

<210> SEQ ID NO 42
<211> LENGTH: 142
<212> TYPE: PRT
<213> ORGANISM: Mus musculus
<223> OTHER INFORMATION: TM191 VH

<400> SEQUENCE: 42

Met Asp Phe Arg Leu Ser Leu Leu Ile Phe Val Leu Ile Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asp Tyr Gly Met Ala Trp Val Arg Gln Ala Pro Gly Lys Gly Pro
    50                  55                  60

Glu Trp Val Ala Phe Ile Ser Asn Leu Ala Tyr Ser Ser Tyr Tyr Ala
65                  70                  75                  80

Asp Thr Val Thr Gly Arg Phe Thr Ile Ser Arg Glu Asn Ala Lys Asn
                85                  90                  95

Thr Leu Tyr Leu Glu Met Ser Ser Leu Arg Ser Glu Asp Ser Ala Met

```
                    100                 105                 110
Tyr Tyr Cys Ala Arg Arg Ile Phe Asp Tyr Asp Gly Asp Gly Pro Tyr
            115                 120                 125

Glu Asp Tyr Trp Gly Gln Gly Thr Ser Val Thr Val Ser Ser
    130                 135                 140
```

<210> SEQ ID NO 43
<211> LENGTH: 390
<212> TYPE: DNA
<213> ORGANISM: Mus musculus
<223> OTHER INFORMATION: TM191 VL

<400> SEQUENCE: 43

```
atggattttc aagtgcagat tttcagcttc ttgctgatca gtgcctcagt cataatgacc     60
agaggacaaa ttgttctcac ccagtctcca gcaatcatgt ctgcctctcc agggagaag    120
gtcactttga cctgcagtgc cacctcaagt gttagttcca ggtacgtgca ctggtaccag    180
cagaagtcag gagcctcccc caaactctgg atttatggca catccaacct ggcttctgga   240
gtccctgctc gcttcagtgg cagtgggtct ggaacctctt actctctcac aatcagcagc   300
gtggaggctg aagatgctgc cacttattac tgccagcagt atcataatga cccacccacg   360
ttcggtgctg ggaccaagct ggagctgaaa                                    390
```

<210> SEQ ID NO 44
<211> LENGTH: 130
<212> TYPE: PRT
<213> ORGANISM: Mus musculus
<223> OTHER INFORMATION: TM191 VL

<400> SEQUENCE: 44

```
Met Asp Phe Gln Val Gln Ile Phe Ser Phe Leu Leu Ile Ser Ala Ser
1               5                   10                  15

Val Ile Met Thr Arg Gly Gln Ile Val Leu Thr Gln Ser Pro Ala Ile
            20                  25                  30

Met Ser Ala Ser Pro Gly Glu Lys Val Thr Leu Thr Cys Ser Ala Thr
        35                  40                  45

Ser Ser Val Ser Ser Arg Tyr Val His Trp Tyr Gln Gln Lys Ser Gly
    50                  55                  60

Ala Ser Pro Lys Leu Trp Ile Tyr Gly Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Val Glu Ala Glu Asp Ala Ala Thr Tyr Tyr Cys Gln
            100                 105                 110

Gln Tyr His Asn Asp Pro Pro Thr Phe Gly Ala Gly Thr Lys Leu Glu
        115                 120                 125

Leu Lys
    130
```

<210> SEQ ID NO 45
<211> LENGTH: 1416
<212> TYPE: DNA
<213> ORGANISM: Artificial Sequence
<220> FEATURE:
<223> OTHER INFORMATION: chimera antibody TM094 H

<400> SEQUENCE: 45

```
atggaatgga tctggatctt tctcttcatc ctgtcaggaa ctgcaggtgt ccaattccag     60
```

```
gttcagctgc agcagtctgg agctgagctg gagaggcctg ggcttcagt gaagctgtcc      120 tgcaaggctt ctggctacac cttcacaagc tatgctataa gctgggtgaa gcagagaatc      180
ggacagggcc ttgagtggat tggagagatc tatcctagaa ataatgatac ttactacaat      240
gagaaattca gggcaaggc cacactgact gcagacaaat cctccagcac agcctacatg      300
cagctcagca gcctgacatc tgaggactct gcagtctatt tctgtgcaag agaaggggac      360
tactatggtg actacgaggg gtttgcttac tggggccaag ggactctggt cgctgtctct      420
gcagctagca ccaagggccc atcggtcttc cccctggcac cctcctccaa gagcacctct      480
gggggcacag cggccctggg ctgcctggtc aaggactact cccccgaacc ggtgacggtg      540
tcgtggaact caggcgccct gaccagcggc gtgcacacct tcccggctgt cctacagtcc      600
tcaggactct actccctcag cagcgtggtg accgtgccct ccagcagctt gggcacccag      660
acctacatct gcaacgtgaa tcacaagccc agcaacacca aggtggacaa gaaagttgag      720
cccaaatctt gtgacaaaac tcacacatgc ccaccgtgcc cagcacctga actcctgggg      780
ggaccgtcag tcttcctctt ccccccaaaa cccaaggaca cctcatgat ctcccggacc      840 cctgaggtca catgcgtggt ggtggacgtg agccacgaag accctgaggt caagttcaac      900
tggtacgtgg acggcgtgga ggtgcataat gccaagacaa agccgcggga ggagcagtac      960
aacagcacgt accgtgtggt cagcgtcctc accgtcctgc accaggactg gctgaatggc     1020
aaggagtaca agtgcaaggt ctccaacaaa gccctcccag cccccatcga gaaaaccatc     1080
tccaaagcca aagggcagcc ccgagaacca caggtgtaca ccctgccccc atcccgggat     1140
gagctgacca agaaccaggt cagcctgacc tgcctggtca aaggcttcta tcccagcgac     1200
atcgccgtgg agtgggagag caatgggcag ccggagaaca actacaagac cacgcctccc     1260
gtgctggact ccgacggctc cttcttcctc tacagcaagc tcaccgtgga caagagcagg     1320
tggcagcagg ggaacgtctt ctcatgctcc gtgatgcatg aggctctgca caaccactac     1380
acgcagaaga gcctctccct gtctccgggt aaatga                              1416
```

<210> SEQ ID NO 46
<211> LENGTH: 471
<212> TYPE: PRT
<213> ORGANISM: Artificial Sequence
<220> FEATURE:
<223> OTHER INFORMATION: chimera antibody TM094 H

<400> SEQUENCE: 46

```
Met Glu Trp Ile Trp Ile Phe Leu Phe Ile Leu Ser Gly Thr Ala Gly
1               5                   10                  15

Val Gln Phe Gln Val Gln Leu Gln Gln Ser Gly Ala Glu Leu Glu Arg
            20                  25                  30

Pro Gly Ala Ser Val Lys Leu Ser Cys Lys Ala Ser Gly Tyr Thr Phe
        35                  40                  45

Thr Ser Tyr Ala Ile Ser Trp Val Lys Gln Arg Ile Gly Gln Gly Leu
    50                  55                  60

Glu Trp Ile Gly Glu Ile Tyr Pro Arg Asn Asn Asp Thr Tyr Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Glu Gly Asp Tyr Tyr Gly Asp Tyr Glu Gly Phe
        115                 120                 125
```

Ala Tyr Trp Gly Gln Gly Thr Leu Val Ala Val Ser Ala Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 47
<211> LENGTH: 705
<212> TYPE: DNA
<213> ORGANISM: Artificial Sequence
<220> FEATURE:
<223> OTHER INFORMATION: chimera antibody TM094 L

<400> SEQUENCE: 47
atgatgtcct ctgctcagtt ccttggtctc ctgttgctct gttttcaagg taccagatgt    60

```
gatatccaga tgacacagac tacatcctcc ctgtctgcct ctctgggaga cagagtcacc    120
atcagttgca gggcaagtca ggatgttcgc aatttttaa actggtatca gcagaaacca    180
gatggaactg ttaaactcct gatctactac acatcaagat tacactcagg agtcccatca    240
aggttcagtg gcagtgggtc tgggacagat tattctctca ccatcagcaa cctggaacct    300
gaagatattg ccacttacta ttgtcagcag tatagtaatc ttccgtatac gttcggatcg    360
gggaccaagt tggaaataaa acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttga                   705
```

<210> SEQ ID NO 48
<211> LENGTH: 234
<212> TYPE: PRT
<213> ORGANISM: Artificial Sequence
<220> FEATURE:
<223> OTHER INFORMATION: chimera antibody TM094 L

<400> SEQUENCE: 48

```
Met Met Ser Ser Ala Gln Phe Leu Gly Leu Leu Leu Cys Phe Gln
1               5                   10                  15

Gly Thr Arg Cys Asp Ile Gln Met Thr Gln Thr Thr Ser Ser Leu Ser
                20                  25                  30

Ala Ser Leu Gly Asp Arg Val Thr Ile Ser Cys Arg Ala Ser Gln Asp
            35                  40                  45

Val Arg Asn Phe Leu Asn Trp Tyr Gln Gln Lys Pro Asp Gly Thr Val
        50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Pro Glu Asp Ile Ala Thr Tyr Tyr Cys Gln Gln Tyr Ser
            100                 105                 110

Asn Leu Pro Tyr Thr Phe Gly Ser Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 49

<211> LENGTH: 1419
<212> TYPE: DNA
<213> ORGANISM: Artificial Sequence
<220> FEATURE:
<223> OTHER INFORMATION: chimera antibody TM191 H

<400> SEQUENCE: 49

| | |
|---|---:|
| atggacttca ggctcagctt acttattttt gtccttattt taaaaggtgt ccagtgtgag | 60 |
| gtgaagctgg tggagtctgg gggaggctta gtgaagcctg agggtccct gaaactctcc | 120 |
| tgtgcagcct ctggattcac tttcagtgac tacggaatgg cgtgggttcg acaggctcca | 180 |
| gggaaggggc tgagtgggt agcattcatt agtaatttgg catatagtag ttattatgca | 240 |
| gacactgtga cgggccgatt caccatctct agagagaatg ccaagaacac cctgtacctg | 300 |
| gaaatgagca gtctgaggtc tgaggactca gccatgtatt actgtgcaag acgaatcttt | 360 |
| gattacgacg gggacggtcc ttatgaggat tactggggtc aaggaacctc agtcaccgtc | 420 |
| tcctcagcta gcaccaaggg cccatcggtc ttccccctgg caccctcctc caagagcacc | 480 |
| tctgggggca gcggccct gggctgcctg gtcaaggact acttccccga accggtgacg | 540 |
| gtgtcgtgga actcaggcgc cctgaccagc ggcgtgcaca ccttcccggc tgtcctacag | 600 |
| tcctcaggac tctactccct cagcagcgtg gtgaccgtgc cctccagcag cttgggcacc | 660 |
| cagacctaca tctgcaacgt gaatcacaag cccagcaaca ccaaggtgga caagaaagtt | 720 |
| gagcccaaat cttgtgacaa aactcacaca tgcccaccgt gcccagcacc tgaactcctg | 780 |
| gggggaccgt cagtcttcct cttccccca aacccaagg acaccctcat gatctcccgg | 840 |
| acccctgagg tcacatgcgt ggtggtggac gtgagccacg aagaccctga ggtcaagttc | 900 |
| aactggtacg tggacggcgt ggaggtgcat aatgccaaga caaagccgcg ggaggagcag | 960 |
| tacaacagca cgtaccgtgt ggtcagcgtc ctcaccgtcc tgcaccagga ctggctgaat | 1020 |
| ggcaaggagt acaagtgcaa ggtctccaac aaagccctcc cagcccccat cgagaaaacc | 1080 |
| atctccaaag ccaagggca gccccgagaa ccacaggtgt acaccctgcc cccatcccgg | 1140 |
| gatgagctga ccaagaacca ggtcagcctg acctgcctgg tcaaaggctt ctatcccagc | 1200 |
| gacatcgccg tggagtggga gagcaatggg cagccggaga caactacaa gaccacgcct | 1260 |
| cccgtgctgg actccgacgg ctccttcttc ctctacagca agctcaccgt ggacaagagc | 1320 |
| aggtggcagc aggggaacgt cttctcatgc tccgtgatgc atgaggctct gcacaaccac | 1380 |
| tacacgcaga agagcctctc cctgtctccg ggtaaatga | 1419 |

<210> SEQ ID NO 50
<211> LENGTH: 472
<212> TYPE: PRT
<213> ORGANISM: Artificial Sequence
<220> FEATURE:
<223> OTHER INFORMATION: chimera antibody TM191 H

<400> SEQUENCE: 50

Met Asp Phe Arg Leu Ser Leu Leu Ile Phe Val Leu Ile Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asp Tyr Gly Met Ala Trp Val Arg Gln Ala Pro Gly Lys Gly Pro
    50                  55                  60

Glu Trp Val Ala Phe Ile Ser Asn Leu Ala Tyr Ser Ser Tyr Tyr Ala

Asp Thr Val Thr Gly Arg Phe Thr Ile Ser Arg Glu Asn Ala Lys Asn
65                  70                  75                  80

Thr Leu Tyr Leu Glu Met Ser Ser Leu Arg Ser Glu Asp Ser Ala Met
            85                  90                  95

Tyr Tyr Cys Ala Arg Arg Ile Phe Asp Tyr Asp Gly Asp Gly Pro Tyr
        100                 105                 110

Glu Asp Tyr Trp Gly Gln Gly Thr Ser Val Thr Val Ser Ser Ala Ser
    115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
        180                 185                 190

Ser Val Val Thr Val Pro Ser Ser Ser Leu Gly Thr Gln Thr Tyr Ile
    195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
        260                 265                 270

Val Asp Val Ser His Glu Asp Pro Glu Val Lys Phe Asn Trp Tyr Val
    275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
        340                 345                 350

Arg Glu Pro Gln Val Tyr Thr Leu Pro Pro Ser Arg Asp Glu Leu Thr
    355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
        420                 425                 430

Ser Cys Ser Val Met His Glu Ala Leu His Asn His Tyr Thr Gln Lys
    435                 440                 445

Ser Leu Ser Leu Ser Pro Gly Lys
450                 455

<210> SEQ ID NO 51

```
<211> LENGTH: 714
<212> TYPE: DNA
<213> ORGANISM: Artificial Sequence
<220> FEATURE:
<223> OTHER INFORMATION: chimera antibody TM191 L

<400> SEQUENCE: 51
atggattttc aagtgcagat tttcagcttc ttgctgatca gtgcctcagt cataatgacc      60
agaggacaaa ttgttctcac ccagtctcca gcaatcatgt ctgcctctcc aggggagaag     120
gtcactttga cctgcagtgc cacctcaagt gttagttcca ggtacgtgca ctggtaccag     180
cagaagtcag gagcctcccc caaactctgg atttatggca catccaacct ggcttctgga     240
gtccctgctc gcttcagtgg cagtgggtct gggacctctt actctctcac aatcagcagc     300
gtggaggctg aagatgctgc cacttattac tgccagcagt atcataatga cccacccacg     360
ttcggtgctg ggaccaagct ggagctgaaa cgtacggtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg ttga           714

<210> SEQ ID NO 52
<211> LENGTH: 237
<212> TYPE: PRT
<213> ORGANISM: Artificial Sequence
<220> FEATURE:
<223> OTHER INFORMATION: chimera antibody TM191 L

<400> SEQUENCE: 52

Met Asp Phe Gln Val Gln Ile Phe Ser Phe Leu Leu Ile Ser Ala Ser
1               5                   10                  15

Val Ile Met Thr Arg Gly Gln Ile Val Leu Thr Gln Ser Pro Ala Ile
            20                  25                  30

Met Ser Ala Ser Pro Gly Glu Lys Val Thr Leu Thr Cys Ser Ala Thr
        35                  40                  45

Ser Ser Val Ser Ser Arg Tyr Val His Trp Tyr Gln Gln Lys Ser Gly
    50                  55                  60

Ala Ser Pro Lys Leu Trp Ile Tyr Gly Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Val Glu Ala Glu Asp Ala Ala Thr Tyr Tyr Cys Gln
            100                 105                 110

Gln Tyr His Asn Asp Pro Pro Thr Phe Gly Ala Gly Thr Lys Leu Glu
        115                 120                 125

Leu Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
```

195                 200                 205
Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235

<210> SEQ ID NO 53
<211> LENGTH: 399
<212> TYPE: DNA
<213> ORGANISM: Mus musculus
<223> OTHER INFORMATION: EA230 VH

<400> SEQUENCE: 53
atgtacttgg gactgaactg tgtattcata gtttttatct taaaaggtgt ccagagtgaa      60
gtgaaacttg aggagtctgg aggagccttg gtgcaacctg gcggatccat gaaactctcc    120
tgtgttgcct caggattcac tgtcagtaac tactggatga gctgggtccg ccagtctcca    180
gagaaggggc ttgagtgggt tgctgaagtt agattgaaat ctaataatta tgtgacccat    240
tatgcggagt ctgtgaaagg gaggttcacc atctcaagag atgattccaa agtagtgtc     300 tacctgcaaa tgaacaactt aagacctgaa gacactggca tttattactg taccccttt     360 gcttactggg gccaagggac tctggtcact gtctctgca                           399

<210> SEQ ID NO 54
<211> LENGTH: 133
<212> TYPE: PRT
<213> ORGANISM: Mus musculus
<223> OTHER INFORMATION: EA230 VH

<400> SEQUENCE: 54

Met Tyr Leu Gly Leu Asn Cys Val Phe Ile Val Phe Ile Leu Lys Gly
1               5                   10                  15

Val Gln Ser Glu Val Lys Leu Glu Glu Ser Gly Gly Ala Leu Val Gln
            20                  25                  30

Pro Gly Gly Ser Met Lys Leu Ser Cys Val Ala Ser Gly Phe Thr Val
        35                  40                  45

Ser Asn Tyr Trp Met Ser Trp Val Arg Gln Ser Pro Glu Lys Gly Leu
    50                  55                  60

Glu Trp Val Ala Glu Val Arg Leu Lys Ser Asn Asn Tyr Val Thr His
65                  70                  75                  80

Tyr Ala Glu Ser Val Lys Gly Arg Phe Thr Ile Ser Arg Asp Asp Ser
                85                  90                  95

Lys Ser Val Tyr Leu Gln Met Asn Asn Leu Arg Pro Glu Asp Thr
            100                 105                 110

Gly Ile Tyr Tyr Cys Thr Pro Phe Ala Tyr Trp Gly Gln Gly Thr Leu
        115                 120                 125

Val Thr Val Ser Ala
    130

<210> SEQ ID NO 55
<211> LENGTH: 390
<212> TYPE: DNA
<213> ORGANISM: Mus musculus
<223> OTHER INFORMATION: EA230 VL

<400> SEQUENCE: 55
atggattttc aggtgcagat tttcagcttc ctgctaatca gtgtctcagt cataatgtcc      60
agaggacaaa ttgttctcac ccagtctcca gcaatcctgt ctgcatctcc tggggagaag    120

| | |
|---|---|
| gtcaccttga cctgcagtgc caattcaagt gtgagttcca gctacttata ctggcaccag | 180 |
| cagaagccag gatcctcccc caaactctgg atttatagga catccaagtt ggcttctgga | 240 |
| gtccctgctc gcttcagtgg cagtgggtct gggacctctt actctctcac aatcagcagc | 300 |
| atggaggctg aagatgctgc ctcttatttc tgccatcagt gggatactta tccacccacg | 360 |
| ttcggagggg ggaccaaact ggaaataaaa | 390 |

<210> SEQ ID NO 56
<211> LENGTH: 130
<212> TYPE: PRT
<213> ORGANISM: Mus musculus
<223> OTHER INFORMATION: EA230 VL

<400> SEQUENCE: 56

Met Asp Phe Gln Val Gln Ile Phe Ser Phe Leu Leu Ile Ser Val Ser
1               5                   10                  15

Val Ile Met Ser Arg Gly Gln Ile Val Leu Thr Gln Ser Pro Ala Ile
            20                  25                  30

Leu Ser Ala Ser Pro Gly Glu Lys Val Thr Leu Thr Cys Ser Ala Asn
        35                  40                  45

Ser Ser Val Ser Ser Ser Tyr Leu Tyr Trp His Gln Gln Lys Pro Gly
    50                  55                  60

Ser Ser Pro Lys Leu Trp Ile Tyr Arg Thr Ser Lys Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Ser Tyr Phe Cys His
            100                 105                 110

Gln Trp Asp Thr Tyr Pro Pro Thr Phe Gly Gly Gly Thr Lys Leu Glu
        115                 120                 125

Ile Lys
    130

<210> SEQ ID NO 57
<211> LENGTH: 1419
<212> TYPE: DNA
<213> ORGANISM: Artificial Sequence
<220> FEATURE:
<223> OTHER INFORMATION: IgG2a type TM191 H

<400> SEQUENCE: 57

| | |
|---|---|
| atggacttca ggctcagctt acttattttt gtccttattt taaaaggtgt ccagtgtgag | 60 |
| gtgaagctgg tggagtctgg gggaggctta gtgaagcctg agggtccct gaaactctcc | 120 |
| tgtgcagcct ctggattcac tttcagtgac tacggaatgg cgtgggttcg acaggctcca | 180 |
| gggaaggggc tgagtgggt agcattcatt agtaatttgg catatagtag ttattatgca | 240 |
| gacactgtga cggccgatt caccatctct agagagaatg ccaagaacac cctgtacctg | 300 |
| gaaatgagca gtctgaggtc tgaggactca gccatgtatt actgtgcaag acgaatcttt | 360 |
| gattacgacg ggacggtcc ttatgaggat tactggggtc aaggaacctc agtcaccgtc | 420 |
| tcctcagcta gcacaacagc cccatcggtc tatccactgg ccctgtgtg tggagataca | 480 |
| actggctcct cggtgactct aggatgcctg gtcaagggtt atttccctga gccagtgacc | 540 |
| ttgacctgga actctgggtc cctgtccagt ggtgtgcaca cttcccagc tgtcctgcag | 600 |
| tctgacctct acaccctcag cagctcagtg actgtaacct cgagcacctg gcccagccag | 660 |

```
tccatcacct gcaatgtggc ccacccggca agcagcacca aggtggacaa gaaaattgag    720
cccagagggc ccacaatcaa gccctgtcct ccatgcaaat gcccagcacc taacctcttg    780
ggtggaccat ccgtcttcat cttccctcca aagatcaagg atgtactcat gatctccctg    840
agccccatag tcatatgtgt ggtggtggat gtgagcgagg atgacccaga tgtccagatc    900
agctggtttg tgaacaacgt ggaagtacac acagctcaga cacaaaccca tagagaggat    960
tacaacagta ctctccgggt ggtcagtgcc ctccccatcc agcaccagga ctggatgagt   1020
ggcaaggagt tcaaatgcaa ggtcaacaac aaagacctcc cagcgcccat cgagagaacc   1080
atctcaaaac ccaaagggtc agtaagagca ccacaggtat atgtcttgcc tccaccagaa   1140
gaagagatga ctaagaaaca ggtcactctg acctgcatgg tcacagactt catgcctgaa   1200
gacatttacg tggagtggac caacaacggg aaaacagagc taaactacaa gaacactgaa   1260
ccagtcctgg actctgatgg ttcttacttc atgtacagca agctgagagt ggaaaagaag   1320
aactgggtgg aaagaaatag ctactcctgt tcagtggtcc acgagggtct gcacaatcac   1380
cacacgacta agagcttctc ccggactccg ggtaaatga                          1419
```

<210> SEQ ID NO 58
<211> LENGTH: 472
<212> TYPE: PRT
<213> ORGANISM: Artificial Sequence
<220> FEATURE:
<223> OTHER INFORMATION: IgG2a type TM191 H

<400> SEQUENCE: 58

```
Met Asp Phe Arg Leu Ser Leu Leu Ile Phe Val Leu Ile Leu Lys Gly
1               5                   10                  15

Val Gln Cys Glu Val Lys Leu Val Glu Ser Gly Gly Gly Leu Val Lys
                20                  25                  30

Pro Gly Gly Ser Leu Lys Leu Ser Cys Ala Ala Ser Gly Phe Thr Phe
            35                  40                  45

Ser Asp Tyr Gly Met Ala Trp Val Arg Gln Ala Pro Gly Lys Gly Pro
        50                  55                  60

Glu Trp Val Ala Phe Ile Ser Asn Leu Ala Tyr Ser Ser Tyr Tyr Ala
65                  70                  75                  80

Asp Thr Val Thr Gly Arg Phe Thr Ile Ser Arg Glu Asn Ala Lys Asn
                85                  90                  95

Thr Leu Tyr Leu Glu Met Ser Ser Leu Arg Ser Glu Asp Ser Ala Met
            100                 105                 110

Tyr Tyr Cys Ala Arg Arg Ile Phe Asp Tyr Asp Gly Asp Gly Pro Tyr
        115                 120                 125

Glu Asp Tyr Trp Gly Gln Gly Thr Ser Val Thr Val Ser Ser Ala Ser
    130                 135                 140

Thr Thr Ala Pro Ser Val Tyr Pro Leu Ala Pro Val Cys Gly Asp Thr
145                 150                 155                 160

Thr Gly Ser Ser Val Thr Leu Gly Cys Leu Val Lys Gly Tyr Phe Pro
                165                 170                 175

Glu Pro Val Thr Leu Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Thr Ser Ser Thr Trp Pro Ser Gln Ser Ile Thr Cys
    210                 215                 220

Asn Val Ala His Pro Ala Ser Ser Thr Lys Val Asp Lys Lys Ile Glu
```

Pro Arg Gly Pro Thr Ile Lys Pro Cys Pro Cys Lys Cys Pro Ala
            225                 230                 235                 240

Pro Asn Leu Leu Gly Gly Pro Ser Val Phe Ile Phe Pro Pro Lys Ile
        245                 250                 255

Lys Asp Val Leu Met Ile Ser Leu Ser Pro Ile Val Thr Cys Val Val
                260                 265                 270

275                 280                 285

Val Asp Val Ser Glu Asp Asp Pro Asp Val Gln Ile Ser Trp Phe Val
        290                 295                 300

Asn Asn Val Glu Val His Thr Ala Gln Thr Gln Thr His Arg Glu Asp
305                 310                 315                 320

Tyr Asn Ser Thr Leu Arg Val Val Ser Ala Leu Pro Ile Gln His Gln
                325                 330                 335

Asp Trp Met Ser Gly Lys Glu Phe Lys Cys Lys Val Asn Asn Lys Asp
            340                 345                 350

Leu Pro Ala Pro Ile Glu Arg Thr Ile Ser Lys Pro Lys Gly Ser Val
        355                 360                 365

Arg Ala Pro Gln Val Tyr Val Leu Pro Pro Glu Glu Glu Met Thr
    370                 375                 380

Lys Lys Gln Val Thr Leu Thr Cys Met Val Thr Asp Phe Met Pro Glu
385                 390                 395                 400

Asp Ile Tyr Val Glu Trp Thr Asn Asn Gly Lys Thr Glu Leu Asn Tyr
                405                 410                 415

Lys Asn Thr Glu Pro Val Leu Asp Ser Asp Gly Ser Tyr Phe Met Tyr
            420                 425                 430

Ser Lys Leu Arg Val Glu Lys Lys Asn Trp Val Glu Arg Asn Ser Tyr
        435                 440                 445

Ser Cys Ser Val Val His Glu Gly Leu His Asn His His Thr Thr Lys
    450                 455                 460

Ser Phe Ser Arg Thr Pro Gly Lys
465                 470

<210> SEQ ID NO 59
<211> LENGTH: 714
<212> TYPE: DNA
<213> ORGANISM: Artificial Sequence
<220> FEATURE:
<223> OTHER INFORMATION: kappa type TM191 L

<400> SEQUENCE: 59
atggattttc aagtgcagat tttcagcttc ttgctgatca gtgcctcagt cataatgacc      60
agaggacaaa ttgttctcac ccagtctcca gcaatcatgt ctgcctctcc aggggagaag     120
gtcactttga cctgcagtgc cacctcaagt gttagttcca ggtacgtgca ctggtaccag     180
cagaagtcag gagcctcccc caaactctgg atttatggca catccaacct ggcttctgga     240
gtccctgctc gcttcagtgg cagtgggtct gggacctctt actctctcac aatcagcagc     300
gtggaggctg aagatgctgc cacttattac tgccagcagt atcataatga cccacccacg     360
ttcggtgctg ggaccaagct ggagctgaaa cgtacggtgg cggccccaac tgtatccatc     420
ttcccaccat ccagtgagca gttaacatct ggaggtgcct cagtcgtgtg cttcttgaac     480
aacttctacc ccaaagacat caatgtcaag tggaagattg atggcagtga cgacaaaat     540 ggcgtcctga cagttggac tgatcaggac agcaaagaca gcacctcag catgagcagc     600 accctcacgt tgaccaagga cgagtatgaa cgacataaca gctatacctg tgaggccact     660

```
cacaagacat caacttcacc cattgtcaag agcttcaaca ggaatgagtg ttga          714
```

<210> SEQ ID NO 60
<211> LENGTH: 237
<212> TYPE: PRT
<213> ORGANISM: Artificial Sequence
<220> FEATURE:
<223> OTHER INFORMATION: kappa type TM191 L

<400> SEQUENCE: 60

```
Met Asp Phe Gln Val Gln Ile Phe Ser Phe Leu Leu Ile Ser Ala Ser
1               5                   10                  15

Val Ile Met Thr Arg Gly Gln Ile Val Leu Thr Gln Ser Pro Ala Ile
            20                  25                  30

Met Ser Ala Ser Pro Gly Glu Lys Val Thr Leu Thr Cys Ser Ala Thr
        35                  40                  45

Ser Ser Val Ser Ser Arg Tyr Val His Trp Tyr Gln Gln Lys Ser Gly
    50                  55                  60

Ala Ser Pro Lys Leu Trp Ile Tyr Gly Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Val Glu Ala Glu Asp Ala Ala Thr Tyr Tyr Cys Gln
            100                 105                 110

Gln Tyr His Asn Asp Pro Pro Thr Phe Gly Ala Gly Thr Lys Leu Glu
        115                 120                 125

Leu Lys Arg Thr Val Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235
```

DIAGNOSIS AND TREATMENT OF CANCER USING ANTI-TMPRSS11E ANTIBODY

TECHNICAL FIELD

The present application claims the priority based on Japanese Patent Application No. 2009-100163 (filed on Apr. 16, 2009), the contents of which are incorporated herein by reference.

The present invention relates to an anti-TMPRSS11E antibody and the diagnosis and treatment of cancer using the antibody.

BACKGROUND ART

TMPRSS11E (also called DESC1) belongs to the type II transmembrane serine protease family. The gene of this protein was discovered as a novel gene whose expression is reduced in squamous cell carcinoma (Lang and Schuller, 2001; Sedghizadeh et al., 2006). Purified soluble TMPRSS11E exhibits protease activity, and it has been reported that cells forced to express TMPRSS11E have an increased ability of cellular infiltration (Viloria et al., 2007). This paper has reported as a result of immunohistological staining using polyclonal antibodies, staining in kidney cancer and breast cancer in some cases, in addition to strong staining in the normal kidney and the normal liver.

However, no document has reported whether or not an antibody targeting TMPRSS11E is effective as a pharmaceutical composition such as an anticancer agent.

CITATION LIST

Non Patent Literature

Non Patent Literature 1: Lang, J. C. and Schuller, D. E. (2001) Differential expression of a novel serine protease homologue in squamous cell carcinoma of the head and neck. Br J Cancer 84, 237-43.

Non Patent Literature 2: Sedghizadeh, P. P., Mallery, S. R., Thompson, S. J., Kresty, L., Beck, F. M., Parkinson, E. K., Biancamano, J. and Lang, J. C. (2006) Expression of the serine protease DESC1 correlates directly with normal keratinocyte differentiation and inversely with head and neck squamous cell carcinoma progression. Head Neck 28, 432-40.

Non Patent Literature 3: Viloria, C. G., Peinado, J. R., Astudillo, A., Garcia-Suarez, O. Gonzalez, M. V., Suarez, C. and Cal, S. (2007) Human DESC1 serine protease confers tumorigenic properties to MDCK cells and it is upregulated in tumors of different origin. Br J Cancer 97, 201-9.

SUMMARY OF INVENTION

Technical Problem

An object of the present invention is to provide novel means for the treatment and diagnosis of cancer.

Solution to Problem

This time, we have obtained a monoclonal antibody against TMPRSS11E for the first time. We have found that this antibody binds to a native form of TMPRSS11E, and TMPRSS11E is highly expressed on the cell membranes of cancer cell lines in flow cytometry. This antibody exhibited antibody-dependent cell-mediated cytotoxicity activity (ADCC activity) and antitumor effect based on internalization activity, demonstrating that it is promising as a therapeutic target. Moreover, this antibody has neutralization activity against protease activity and is also expected to have effect brought about by the inhibition of TMPRSS11E functions.

Specifically, the present invention has been achieved based on these findings and relates to the diagnosis and treatment of cancer using the anti-TMPRSS11E antibody. The present invention provides the following [1] to [20]:

[1]
An antibody binding to a TMPRSS11E protein.

[2]
The antibody according to [1], wherein the antibody has cytotoxic activity.

[3]
The antibody according to [2], wherein the cytotoxic activity is antibody-dependent cellular cytotoxicity (ADCC activity).

[4]
The antibody according to [2], wherein the cytotoxic activity is complement-dependent cytotoxicity (CDC activity).

[5]
The antibody according to any of [1] to [4], wherein the antibody has internalization activity.

[6]
The antibody according to [5], wherein the antibody is conjugated to a cytotoxic substance.

[7]
The antibody according to any of [1] to [6], wherein the antibody has neutralization activity.

[8]
An antibody binding to a TMPRSS11E protein, the antibody being selected from the followings:
(1) an antibody comprising a heavy chain variable region comprising heavy chain CDR1 having the amino acid sequence represented by SEQ ID NO: 3, heavy chain CDR2 having the amino acid sequence represented by SEQ ID NO: 4, and heavy chain CDR3 having the amino acid sequence represented by SEQ ID NO: 5;
(2) an antibody comprising a heavy chain variable region comprising heavy chain CDR1 having the amino acid sequence represented by SEQ ID NO: 6, heavy chain CDR2 having the amino acid sequence represented by SEQ ID NO: 7, and heavy chain CDR3 having the amino acid sequence represented by SEQ ID NO: 8;
(3) an antibody comprising a heavy chain variable region comprising heavy chain CDR1 having the amino acid sequence represented by SEQ ID NO: 9, heavy chain CDR2 having the amino acid sequence represented by SEQ ID NO: 10, and heavy chain CDR3 having the amino acid sequence represented by SEQ ID NO: 11;
(4) an antibody comprising a light chain variable region comprising light chain CDR1 having the amino acid sequence represented by SEQ ID NO: 12, light chain CDR2 having the amino acid sequence represented by SEQ ID NO: 13, and light chain CDR3 having the amino acid sequence represented by SEQ ID NO: 14;
(5) an antibody comprising a light chain variable region comprising light chain CDR1 having the amino acid sequence represented by SEQ ID NO: 15, light chain CDR2 having the amino acid sequence represented by SEQ ID NO: 16, and light chain CDR3 having the amino acid sequence represented by SEQ ID NO: 17;
(6) an antibody comprising a light chain variable region comprising light chain CDR1 having the amino acid sequence represented by SEQ ID NO: 18, light chain CDR2 having the amino acid sequence represented by SEQ ID NO: 19, and light chain CDR3 having the amino acid sequence represented by SEQ ID NO: 20;

(7) an antibody comprising the heavy chain variable region of the antibody (1) and the light chain variable region of the antibody (4);

(8) an antibody comprising the heavy chain variable region of the antibody (2) and the light chain variable region of the antibody (5);

(9) an antibody comprising the heavy chain variable region of the antibody (3) and the light chain variable region of the antibody (6);

(10) an antibody derived from any antibody of (1) to (9) by the substitution, deletion, addition, and/or insertion of one or more amino acid(s), wherein the antibody has activity equivalent to that of the any antibody of (1) to (9); and

(11) an antibody binding to the same epitope as that via which any antibody of (1) to (9) binds to the TMPRSS11E protein.

[9]

The antibody according to any of [1] to [7], wherein the antibody recognizes an epitope consisting of amino acids 159-423 in the amino acid sequence of SEQ ID NO: 2.

[10]

A pharmaceutical composition comprising the antibody according to any of [1] to [9] as an active ingredient.

[11]

The pharmaceutical composition according to [10], wherein the pharmaceutical composition is an anticancer agent.

[12]

The pharmaceutical composition according to [11], wherein the anticancer agent targets lung cancer, uterine cervix cancer, or esophagus cancer.

[13]

A method for diagnosing cancer, comprising the following steps:

(a) preparing a sample isolated from a test subject; and (b) detecting the expression level of a TMPRSS11E protein or a TMPRSS11E gene in the sample.

[14]

The diagnosis method according to [13], wherein the diagnosis method is intended for the diagnosis of lung cancer, uterine cervix cancer, or esophagus cancer.

[15]

A diagnostic drug for cancer comprising the antibody according to any of [1] to [9].

[16]

The diagnostic drug according to [15], wherein the diagnostic drug is intended for the diagnosis of lung cancer, uterine cervix cancer, or esophagus cancer.

[17]

The antibody according to any of [1] to [9], wherein the antibody is used in the diagnosis or treatment of cancer.

[18]

The antibody according to [17] or [18], wherein the cancer is lung cancer, uterine cervix cancer, or esophagus cancer.

[19]

A method for treating cancer using the antibody according to any of [1] to [9].

[20]

The method for treating cancer according to [19], wherein the treatment method is intended for the treatment of lung cancer, uterine cervix cancer, or esophagus cancer.

Advantageous Effects of Invention

The present invention provides novel means for the treatment and diagnosis of cancer, particularly, lung cancer, uterine cervix cancer, or esophagus cancer.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 4 shows the ADCC activity of an anti-TMPRSS11E antibody against cancer cell lines.

FIG. 5 shows the antitumor effect of an anti-TMPRSS11E antibody using Hum-ZAP.

FIG. 8 shows immunohistochemical analysis using an anti-TMPRSS11E antibody.

FIG. 9 shows the avidity of an anti-TMPRSS11E antibody to a parental strain SK-Hep1 and a TMPRSS11E-expressing strain by flow cytometry.

DESCRIPTION OF EMBODIMENTS

1. TMPRSS11E

Figure 1:
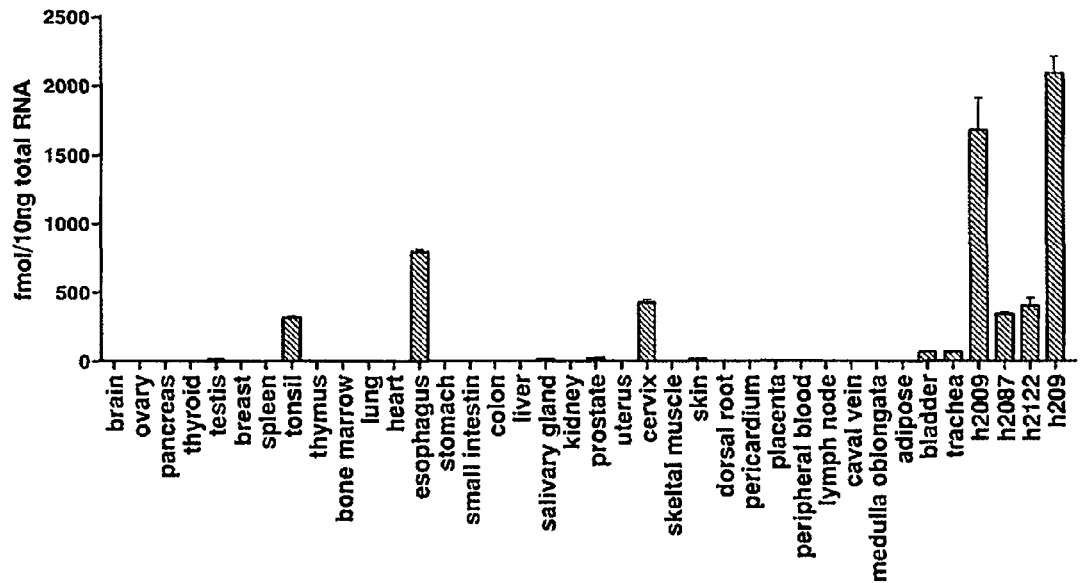
FIG. 1 shows TMPRSS11E mRNA levels in normal tissues and cancer cell lines.

TMPRSS11E (also called DESC1) belongs to the type II transmembrane serine protease family.

The origin of the TMPRSS11E protein used in the present invention is not particularly limited, and any of TMPRSS11E proteins known in the art can be used. Preferably, the TMPRSS11E protein is human TMPRSS11E. The amino acid sequence of human TMPRSS11E and a nucleotide sequence encoding this are known in the art and registered in a public database such as GenBank or Unigene, for example, as GenBank Accession No: NM_014058 (nucleotide sequence=SEQ ID NO: 1, amino acid sequence=SEQ ID NO: 2).

As a result of expression analysis using an anti-TMPRSS11E antibody, the present inventors have found that TMPRSS11E is expressed in lung cancer, uterine cervix cancer, or esophagus cancer tissues.

2. Anti-TMPRSS11E Antibody 2.1 Anti-TMPRSS11E Antibody

An anti-TMPRSS11E antibody used in the present invention is not limited by its origin, type, shape, and the like as long as the anti-TMPRSS11E antibody binds to the TMPRSS11E protein. Specifically, antibodies such as non-human animal antibodies (e.g., mouse, rat, and camel antibodies), human antibodies, chimeric antibodies, and humanized antibodies can be used. The anti-TMPRSS11E antibody used in the present invention may be a polyclonal or monoclonal antibody and is preferably a monoclonal antibody. It is preferred that the antibody should bind to the TMPRSS11E protein with high specificity. More preferably, its binding is particularly specific for human TMPRSS11E.

The anti-TMPRSS11E antibody used in the present invention can be obtained as a polyclonal or monoclonal antibody using means known in the art. The anti-TMPRSS11E antibody used in the present invention is particularly preferably a mammal-derived monoclonal antibody. The mammal-derived monoclonal antibody encompasses, for example, those produced by hybridomas and those produced by hosts transformed with expression vectors comprising the antibody gene by a genetic engineering approach.

The anti-TMPRSS11E antibody of the present invention may be modified with various molecules such as polyethylene glycol (PEG). Moreover, the anti-TMPRSS11E antibody of the present invention may be modified with a chemotherapeutic agent, a radioactive chemical, or the like, having cytotoxic activity, as described later.

Examples of the antibody that recognizes TMPRSS11E, used in the present invention, can include the following antibodies:

(1) an antibody comprising a heavy chain variable region comprising heavy chain CDR1 having the amino acid sequence represented by SEQ ID NO: 3, heavy chain CDR2 having the amino acid sequence represented by SEQ ID NO: 4, and heavy chain CDR3 having the amino acid sequence represented by SEQ ID NO: 5;
(2) an antibody comprising a heavy chain variable region comprising heavy chain CDR1 having the amino acid sequence represented by SEQ ID NO: 6, heavy chain CDR2 having the amino acid sequence represented by SEQ ID NO: 7, and heavy chain CDR3 having the amino acid sequence represented by SEQ ID NO: 8;
(3) an antibody comprising a heavy chain variable region comprising heavy chain CDR1 having the amino acid sequence represented by SEQ ID NO: 9, heavy chain CDR2 having the amino acid sequence represented by SEQ ID NO: 10, and heavy chain CDR3 having the amino acid sequence represented by SEQ ID NO: 11;
(4) an antibody comprising a light chain variable region comprising light chain CDR1 having the amino acid sequence represented by SEQ ID NO: 12, light chain CDR2 having the amino acid sequence represented by SEQ ID NO: 13, and light chain CDR3 having the amino acid sequence represented by SEQ ID NO: 14;
(5) an antibody comprising a light chain variable region comprising light chain CDR1 having the amino acid sequence represented by SEQ ID NO: 15, light chain CDR2 having the amino acid sequence represented by SEQ ID NO: 16, and light chain CDR3 having the amino acid sequence represented by SEQ ID NO: 17;
(6) an antibody comprising a light chain variable region comprising light chain CDR1 having the amino acid sequence represented by SEQ ID NO: 18, light chain CDR2 having the amino acid sequence represented by SEQ ID NO: 19, and light chain CDR3 having the amino acid sequence represented by SEQ ID NO: 20;
(7) an antibody comprising the heavy chain variable region of the antibody (1) and the light chain variable region of the antibody (4);
(8) an antibody comprising the heavy chain variable region of the antibody (2) and the light chain variable region of the antibody (5);
(9) an antibody comprising the heavy chain variable region of the antibody (3) and the light chain variable region of the antibody (6);
(10) an antibody derived from any antibody of (1) to (9) by the substitution, deletion, addition, and/or insertion of one or more amino acid(s), wherein the antibody has activity equivalent to that of the any antibody of (1) to (9); and
(11) an antibody binding to the same epitope as that via which any antibody of (1) to (9) binds to the TMPRSS11E protein.

In the present invention, the phrase "having activity equivalent to that of the antibody of the present invention" refers to having avidity to TMPRSS11E, neutralization activity, internalization activity, and/or cytotoxic activity (ADCC activity, CDC activity, etc.) against TMPRSS11E-expressing cells equivalent to those of the antibody of the present invention. In the present invention, the equivalent activity is not necessarily required to be identical activity and needs only to be, for example, 50% or more, preferably 70% or more, more preferably 90% or more activity compared to that of any antibody of (1) to (9). The upper limit of the activity is not particularly limited, and examples thereof can include 1000% or less, 500% or less, 300% or less, 150% or less, and 100% or less.

The antibody derived from the antibody of the present invention by the substitution, deletion, addition, and/or insertion of one or more amino acid(s) is also incorporated in the scope of the present invention and may be prepared artificially or may naturally occur. A method for introducing a mutation to polypeptides is one of methods well known by those skilled in the art for preparing polypeptides functionally equivalent to certain polypeptides. For example, those skilled in the art can prepare an antibody functionally equivalent to the antibody of the present invention by appropriately introducing a mutation to the antibody of the present invention using site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc Natl Acad Sci USA. 82, 488-492; and Kunkel (1988) Methods Enzymol. 85, 2763-2766) or the like. Moreover, such an amino acid mutation can occur in the natural world. Such an antibody which has an amino acid sequence derived from the amino acid sequence of the antibody of the present invention by the mutation of one or more amino acid(s) and is functionally equivalent to the antibody of the present invention is also encompassed by the antibody of the present invention.

In such a variant, the number of amino acids to be varied is usually within 50 amino acids, preferably within 30 amino acids, more preferably within 10 amino acids (e.g., within 5 amino acids).

For amino acid residues to be varied, it is preferred that this mutation should be performed conservatively between amino acids having the same side chain property. For example, the following classification has been established based on the properties of amino acid side chains:
hydrophobic amino acids (A, I, L, M, F, P, W, Y, and V),
  hydrophilic amino acids (R, D, N, C, E, Q, G, H, K, S, and T),
amino acids having an aliphatic side chain (G, A, V, L, I, and P),
amino acids having a hydroxyl group-containing side chain (S, T, and Y),
amino acids having a sulfur atom-containing side chain (C and M), amino acids having a carboxylic acid- and amide-containing side chain (D, N, E, and Q),
amino acids having a base-containing side chain (R, K, and H), and
amino acids having an aromatic group-containing side chain (H, F, Y, and W).
(All the symbols within the parentheses represent a single-character code for each amino acid)

It is already known that a polypeptide having an amino acid sequence modified from a certain amino acid sequence by the deletion and/or addition of one or more amino acid residue(s) and/or by the substitution by other amino acids maintains the biological activity of the original polypeptide. (Mark, D. F. et al., Proc. Natl. Acad. Sci. USA (1984) 81, 5662-5666; Zoller, M. J. and Smith, M., Nucleic Acids Research (1982) 10, 6487-6500; Wang, A. et al., Science 224, 1431-1433; and Dalbadie-McFarland, G. et al., Proc. Natl. Acad. Sci. USA (1982) 79, 6409-6413). Specifically, when an amino acid in an amino acid sequence constituting a certain polypeptide is substituted by an amino acid classified into the same group thereas, it is allegedly highly probable that the polypeptide maintains the activity. In the present invention, the substitution between amino acids within each of the amino acid groups is referred to as conservative substitution.

Moreover, the present invention also provides an antibody binding to the same epitope as that to which any antibody of (1) to (9) binds. Specific examples of the antibodies (1) to (9) can include TM094, TM191, and EA230 described in Examples of the present application. Specifically, the present invention also provides an antibody which recognizes the same epitope as that recognized by TM094, TM191, or EA230.

Whether an antibody to be tested and a certain antibody share an epitope can be confirmed based on their competition for the same epitope. The competition between the antibodies is detected by cross-blocking assay or the like. For example, competitive ELISA assay is preferable cross-blocking assay.

Specifically, in the cross-blocking assay, TMPRSS11E proteins coated on the wells of a microtiter plate are preincubated in the presence or absence of a candidate competing antibody, and the anti-TMPRSS11E antibody of the present invention is then added to the wells. The amount of the anti-TMPRSS11E antibody of the present invention bound to the TMPRSS11E protein in the well indirectly correlates with the binding capability of the candidate competing antibody (antibody to be tested) that competes therewith for the binding to the same epitope. Specifically, the larger affinity the antibody to be tested has for the same epitope, the smaller amount of the anti-TMPRSS11E antibody of the present invention is bound to the TMPRSS11E protein-coated well while the larger amount of the antibody to be tested is bound to the TMPRSS11E protein-coated well.

The amount of the antibody bound to the well can be measured easily by labeling the antibody in advance. For example, a biotin-labeled antibody can be measured by use of an avidin-peroxidase conjugate and an appropriate substrate. The cross-blocking assay using enzyme (e.g., peroxidase) labeling is particularly referred to as competitive ELISA assay. The antibody can be labeled with other detectable or measurable labeling substances. Specifically, radiolabeling, fluorescent labeling, or the like is known in the art.

Furthermore, when the antibody to be tested has constant regions derived from a species different from that of the anti-TMPRSS11E antibody of the present invention, the amount of any antibody bound to the well can also be measured using a labeled antibody that recognizes any constant region. Alternatively, even antibodies differing in class, albeit derived from the same species, can be measured for their respective amounts bound to the well using antibodies that discriminate each class.

Provided that the candidate competing antibody can block the binding of the anti-TMPRSS11E antibody by at least 20%, preferably at least 30%, more preferably at least 50%, yet more preferably at least 80%, compared to the avidity obtained in the control test performed in the absence of the candidate competing antibody, this candidate competing antibody is determined as an antibody that binds to substantially the same epitope as that to which the anti-TMPRSS11E antibody of the present invention binds or as an antibody that competes therewith for the binding to the same epitope.

Moreover, examples of a preferable aspect of the antibody of the present invention can include an antibody which recognizes a region from Ser 159 to Ile 423 or a region from Tyr 42 to Arg 191 in TMPRSS11E.

Such an antibody has high cytotoxic activity, internalization activity, and/or neutralization activity, is useful as a pharmaceutical drug, particularly, an anticancer agent.

2.2 Genetically Modified Anti-TMPRSS11E Antibody

The antibody, when administered to humans, can be converted to a genetically recombinant antibody that has been engineered artificially, for example, for the purpose of reducing heteroantigenicity in humans. The genetically recombinant antibody encompasses, for example, chimeric antibodies and humanized antibodies. These engineered antibodies can be produced using a method known in the art.

(1) Chimeric Antibody

The chimeric antibodies refer to antibodies comprising variable and constant regions of different origins ligated with each other. For example, mouse-human heterogeneous chimeric antibodies are antibodies comprising the heavy and light chain variable regions of a mouse antibody and the heavy and light chain constant regions of a human antibody. Mouse antibody variable region-encoding DNAs are ligated with human antibody constant region-encoding DNAs, and the ligation products can be incorporated into expression vectors to prepare chimeric antibody-expressing recombinant vectors. Cells transformed with these vectors (recombinant cells) can be cultured for the expression of the DNA insert to obtain the chimeric antibodies produced during the culture.

Human antibody constant regions are used as the constant regions of the chimeric antibodies. For example, Cγ1, Cγ2, Cγ3, Cγ4, Cμ, Cδ, Cα1, Cα2, and Cε can be used as heavy chain constant regions. Moreover, Cκ and Cλ can be used as light chain constant regions. The amino acid sequences of these constant regions and nucleotide sequences encoding them are known in the art. Moreover, one or more amino acid(s) in the human antibody constant regions can be substituted, deleted, added, and/or inserted for improving the stability of the antibody itself or its production.

(2) Humanized Antibody

In general, the chimeric antibodies comprise non-human animal-derived antibody variable regions and human antibody-derived constant regions. By contrast, the humanized antibodies comprise non-human animal-derived antibody complementarity-determining regions (CDRs), human antibody-derived framework regions (FRs), and human antibody-derived constant regions. The humanized antibodies are also called reshaped human antibodies. Specifically, for example, humanized antibodies comprising non-human animal (e.g., mouse) antibody CDRs grafted in human antibodies are known in the art. The humanized antibodies are useful as active ingredients for a therapeutic agent of the present invention, owing to their reduced antigenicity in the human body.

Each antibody variable region usually comprises 3 CDRs flanked by 4 FRs. The CDR regions substantially determine the binding specificity of the antibody. The CDRs have diverse amino acid sequences. On the other hand, amino acid sequences constituting the FRs often exhibit high homology among antibodies having different binding specificities. Therefore, in general, the binding specificity of a certain antibody can allegedly be transplanted to other antibodies through CDR grafting.

General gene recombination approaches are also known for obtaining the humanized antibodies. Specifically, for example, Overlap Extension PCR is known in the art as a method for grafting mouse antibody CDRs into human FRs. In the Overlap Extension PCR, primers are used in which a nucleotide sequence encoding each mouse antibody CDR to be grafted is added to primers for human antibody FR synthesis. The primers are prepared for each of the 4 FRs. In the mouse CDR grafting into the human FRs, in general, it is allegedly advantageous to select human FRs highly homologous to mouse FRs for maintaining the CDR functions. Specifically, it is generally preferred to use human FRs comprising amino acid sequences highly homologous to those of the FRs adjacent to the mouse CDRs to be grafted.

Moreover, the nucleotide sequences to be ligated are designed such that they are connected in frame. The human FRs are individually synthesized using their respective primers. As a result, products are obtained, which comprise the mouse CDR-encoding DNA added to each FR-encoding sequence. The mouse CDR-encoding nucleotide sequence in each product is designed such that the nucleotide sequence overlaps with another. Subsequently, the overlapping CDR portions in the products synthesized with human antibody genes as templates are annealed to each other for complementary strand synthesis reaction. Through this reaction, the human FR sequences are ligated via the mouse CDR sequences.

Finally, the full length of the gene of the variable region comprising 3 CDRs and 4 FRs ligated is amplified with primers that respectively anneal to the 5' and 3' ends thereof and comprise an added recognition sequence for an appropriate restriction enzyme. The DNA thus obtained and human antibody constant region-encoding DNA can be inserted into expression vectors such that they are fused in frame to prepare vectors for human antibody expression. These vectors are introduced into hosts to establish recombinant cells, which are then cultured for the expression of the humanized antibody-encoding DNA to produce the humanized antibodies into the cultures of the cultured cells (see European Patent Publication No. EP 239400 and International Publication No. WO 96/02576).

The humanized antibodies thus prepared can be evaluated for their avidities for the antigen by qualitative or quantitative assay to preferably select human antibody FRs that allow CDRs to form a favorable antigen-binding site when ligated via the CDRs. If necessary, FR amino acid residue(s) may be substituted such that the CDRs of the humanized antibody form an appropriate antigen-binding site. For example, a mutation can be introduced in the amino acid sequence of FR by applying the PCR method used in the mouse CDR grafting into the human FRs. Specifically, a mutation of a partial nucleotide sequence can be introduced in the primers annealing to the FR nucleotide sequence. The FR nucleotide sequence synthesized using such primers contains the mutation thus introduced. The variant antibodies having the substituted amino acid(s) can be evaluated for their avidities for the antigen by the same assay as above to select variant FR sequences having the desired property (Sato, K. et al., Cancer Res, 1993, 53, 851-856).

(3) Low-Molecular Antibody

The antibody of the present invention encompasses not only bivalent antibodies typified by IgG (IgG1, IgG2, IgG4, etc.) but also monovalent antibodies or polyvalent antibodies typified by IgM as long as these antibodies bind to the TMPRSS11E protein. The polyvalent antibody of the present invention encompasses polyvalent antibodies having antigen-binding sites, all of which are the same as each other or some or all of which are different from each other. The antibody of the present invention is not limited to whole antibody molecules and may be a low-molecular antibody or a modified form thereof as long as the antibody binds to the TMPRSS11E protein.

The low-molecular antibody encompasses an antibody fragment deficient in a portion of the whole antibody (e.g., whole IgG). Such partial deficiency of the antibody molecule is accepted as long as the resultant antibody fragment is capable of binding to the TMPRSS11E antigen. It is preferred that the antibody fragment according to the present invention should contain one or both of heavy chain variable (VH) and light chain variable (VL) regions. It is also preferred that the antibody fragment according to the present invention should contain CDRs. The number of CDRs contained in the antibody fragment of the present invention is not particularly limited and is preferably at least 6 CDRs: heavy chain CDR1, CDR2, and CDR3 and light chain CDR1, CDR2, and CDR3.

The amino acid sequence of VH or VL can contain substitution, deletion, addition, and/or insertion. Furthermore, the antibody fragment of the present invention may be deficient in a portion of one or both of VH and VL as long as the resultant antibody fragment is capable of binding to the TMPRSS11E antigen. Moreover, its variable region may be chimerized or humanized. Specific examples of the antibody fragment can include Fab, Fab', F(ab')2, and Fv. Moreover, specific examples of the low-molecular antibody can include Fab, Fab', F(ab')2, Fv, scFv (single chain Fv), Diabody, sc(Fv)2 (single chain (Fv)2), and scFv-Fc. In the present invention, the low-molecular antibody is preferably Diabody or sc(Fv)2. These antibody multimers (e.g., dimmers, trimers, tetramers, and polymers) are also encompassed by the low-molecular antibody of the present invention.

Such fragments of the antibody can be obtained by enzymatically treating the antibody to form antibody fragments. The digestive enzymes cleave the antibody fragment at a particular position to give antibody fragments having a particular structure. For example, papain, pepsin, or plasmin is known in the art as the enzyme for forming the antibody fragments. The papain digestion gives F(ab)2 or Fab, and the pepsin digestion gives F(ab')2 or Fab'. Alternatively, genes encoding these antibody fragments are constructed, and these genes can be introduced into expression vectors and then expressed in appropriate host cells (see e.g., Co, M. S. et al., J. Immunol. (1994) 152, 2968-2976; Better, M. & Horwitz, A. H. Methods in Enzymology (1989) 178, 476-496; Plueckthun, A. & Skerra, A. Methods in Enzymology (1989) 178, 497-515; Lamoyi, E., Methods in Enzymology (1986) 121, 652-663; Rousseaux, J. et al., Methods in Enzymology (1986) 121, 663-669; and Bird, R. E. et al., TIBTECH (1991) 9, 132-137).

The use of a genetic engineering approach for the enzymatically obtained antibody fragments can delete an arbitrary portion of the antibody. The low-molecular antibody according to the present invention can be an antibody fragment that lacks an arbitrary region as long as the antibody fragment has binding affinity for TMPRSS11E.

i) Diabody

The Diabody refers to a bivalent antibody fragment constructed by gene fusion (e.g., Holliger P et al., Proc. Natl. Acad. Sci. USA 90: 6444-6448 (1993), EP404,097, and WO 93/11161). The Diabody is a dimer comprising two polypeptide chains. Usually, each of the polypeptide chains constituting the dimer comprises the heavy chain variable region and the light chain variable region linked via a linker on the same chain. The linker in the Diabody is generally too short to allow paring between the heavy chain variable region and the light chain variable region on the same chain. Specifically, the number of amino acid residues constituting the linker is, for example, approximately 5 residues. Therefore, the heavy chain variable region and the light chain variable region encoded on the same polypeptide chain cannot together form a single chain variable region fragment. Instead, they form a dimer by pairing with another single chain variable region fragment. As a result, the Diabody has two antigen-binding sites.

ii) scFv

The scFv is obtained by linking the heavy chain variable region and the light chain variable region of the antibody. In the scFv, the heavy chain variable region and the light chain variable region are linked via a linker, preferably, a peptide linker (Huston, J. S. et al., Proc. Natl. Acad. Sci. U.S.A, 1988, 85, 5879-5883.). The heavy chain variable region and the light chain variable region in the scFv can be derived from any of the antibodies described in the present specification. The peptide linker that links the variable regions is not particularly limited. For example, an arbitrary single chain peptide of approximately 3 to 25 residues can be used as the linker. Specifically, for example, a peptide linker described later can be used.

The variable regions of both the chains can be linked, for example, by PCR as described above. First, of the following DNAs, DNAs encoding the whole or desired partial amino acid sequence are used as templates for linking the variable regions by PCR:

DNA sequences encoding the heavy chain or heavy chain variable region of the antibody, and DNA sequences encoding the light chain or light chain variable region of the antibody.

The heavy chain variable region-encoding DNA and the light chain variable region-encoding DNA are respectively amplified by PCR using a pair of primers having sequences corresponding to both terminal sequences of each DNA to be amplified. Subsequently, DNA encoding the peptide linker portion is prepared. The DNA encoding the peptide linker can also be synthesized using PCR. Nucleotide sequences that can be linked to the amplification product of each variable region gene separately synthesized are respectively added to the 5' sequences of primers used in this PCR. Subsequently, PCR reaction is performed using each DNA of [heavy chain variable region DNA]-[peptide linker DNA]-[light chain variable region DNA] and primers for assembly PCR.

The primers for assembly PCR comprises the combination of a primer annealed to the 5' sequence of the [heavy chain variable region DNA] and a primer annealed to the 3' sequence of the [light chain variable region DNA]. Specifically, the primers for assembly PCR are a primer set that is capable of amplifying DNA encoding the full-length sequence of the scFv to be synthesized. On the other hand, the [peptide linker DNA] contains the added nucleotide sequences that can be linked to each variable region DNA. As a result, these DNAs are linked and, further, finally prepared into a full-length scFv gene amplification product using the primers for assembly PCR. Once the scFv-encoding DNA is prepared, expression vectors containing this DNA and cells transformed with the expression vectors (recombinant cells) can be obtained according to a routine method. Moreover, the resultant recombinant cells can be cultured for the expression of the scFv-encoding DNA to obtain the scFv.

iii) scFv-Fc

The scFv-Fc is a low-molecular antibody comprising an Fc region fused to scFv (Cellular & Molecular Immunology 2006; 3: 439-443). The origin of the scFv used in the scFv-Fc is not particularly limited, and, for example, scFv derived from IgM can be used. Moreover, the origin of the Fc is not particularly limited, and, for example, Fc derived from human IgG (human IgG1, etc.) can be used. Thus, examples of a preferable aspect of the scFv-Fc can include scFv-Fc comprising an IgM antibody scFv fragment linked to human IgG1 CH2 (e.g., Cγ2) and CH3 (e.g., Cγ3) via the hinge region (Hγ) of human IgG1.

iv) sc(Fv)2

The sc(Fv)2 is a low-molecular antibody having a single chain comprising two heavy chain variable regions (VHs) and two light chain variable regions (VLs) linked via linkers or the like (Hudson et al., J. Immunol. Methods 1999; 231: 177-189). The sc(Fv)2 can be prepared, for example, by linking scFvs via a linker. The linking of the 4 antibody variable regions usually requires 3 linkers.

Moreover, the sc(Fv)2 is preferably an antibody wherein two VHs and two VLs are aligned as VH, VL, VH, and VL (i.e., [VH]-linker-[VL]-linker-[VH]-linker-[VL]) in this order starting at the N-terminus of the single chain polypeptide.

The order of two VHs and two VLs is not particularly limited to the arrangement described above and may be any order of arrangement. Examples thereof can also include the following arrangements:

[VL]-linker-[VH]-linker-[VH]-linker-[VL],
[VH]-linker-[VL]-linker-[VL]-linker-[VH],
[VH]-linker-[VH]-linker-[VL]-linker-[VL],
[VL]-linker-[VL]-linker-[VH]-linker-[VH], and
[VL]-linker-[VH]-linker-[VL]-linker-[VH].

For example, an arbitrary peptide linker or synthetic compound linker (e.g., linkers disclosed in the reference Protein Engineering, 9 (3), 299-305, 1996) that can be introduced by genetic engineering can be used as the linker that links the antibody variable regions. These plural linkers may be the same. Alternatively, different linkers may be used. In the present invention, the peptide linker is preferable. The length of the peptide linker is not particularly limited and can be selected appropriately by those skilled in the art according to the purpose. The number of amino acid residues constituting the peptide linker is usually 1 to 100 amino acids, preferably 3 to 50 amino acids, more preferably 5 to 30 amino acids, particularly preferably 12 to 18 amino acids (e.g., 15 amino acids).

The amino acid sequence constituting the peptide linker can be an arbitrary sequence as long as this sequence does not inhibit the binding effect of the scFv. For example, the following amino acid sequences can be used for the peptide linker:

Ser,

Gly-Ser,

Gly-Gly-Ser,

```
Ser-Gly-Gly,

Gly-Gly-Gly-Ser  (SEQ ID NO: 21),

Ser-Gly-Gly-Gly  (SEQ ID NO: 22),

Gly-Gly-Gly-Gly-Ser  (SEQ ID NO: 23),

Ser-Gly-Gly-Gly-Gly  (SEQ ID NO: 24),

Gly-Gly-Gly-Gly-Gly-Ser  (SEQ ID NO: 25),

Ser-Gly-Gly-Gly-Gly-Gly  (SEQ ID NO: 26),

Gly-Gly-Gly-Gly-Gly-Gly-Ser  (SEQ ID NO: 27)

Ser-Gly-Gly-Gly-Gly-Gly-Gly  (SEQ ID NO: 28), (Gly-Gly-Gly-Gly-Ser   (SEQ ID NO: 29))n,
and (Ser-Gly-Gly-Gly-Gly   (SEQ ID NO: 30))n.
[n is an integer of 1 or more]
```

The amino acid sequence of the peptide linker can be selected appropriately by those skilled in the art according to the purpose. For example, the integer n that determines the length of the peptide linker is usually 1 to 5, preferably 1 to 3, more preferably 1 or 2.

Accordingly, examples of a particularly preferable aspect of the sc(Fv)2 according to the present invention can include the following sc(Fv)2:
[VH]-peptide linker (15 amino acids)-[VL]-peptide linker (15 amino acids)-[VH]-peptide linker (15 amino acids)-[VL].

Alternatively, the variable regions can also be linked using the chemically synthesized linker (chemical cross-linking agent). Cross-linking agents usually used in the cross-link of peptide compounds or the like can be used in the present invention. For example, chemical cross-linking agents as shown below are known in the art. These cross-linking agents are commercially available.
N-hydroxysuccinimide (NHS),
disuccinimidyl suberate (DSS),
bis(sulfosuccinimidyl) suberate (BS3),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST),
disulfosuccinimidyl tartrate (sulfo-DST),
bis[2-(succinimidoxycarbonyloxy)ethyl]sulfone (BSOCOES), and
bis[2-(sulfosuccinimidoxycarbonyloxy)ethyl]sulfone (sulfo-BSOCOES), etc.

3. Activity of Anti-TMPRSS11E Antibody (1) Cytotoxic Activity

For the treatment of cell-proliferative disease such as cancer, it is preferred that the antibody should maintain its effector activity. Specifically, the preferable antibody according to the present invention has both of binding affinity for TMPRSS11E and effector functions. The effector functions of the antibody encompass antibody-dependent cell-mediated cytotoxicity (ADCC) activity and complement-dependent cytotoxicity (CDC) activity. The therapeutic antibody according to the present invention particularly preferably possesses one or both of ADCC activity and CDC activity as effector functions.

When the antibody of the present invention is used for the therapeutic purpose, the antibody is preferably an antibody having cytotoxic activity.

Examples of the cytotoxic activity according to the present invention can include ADCC activity and CDC activity. In the present invention, the ADCC activity means the activity of damaging target cells through the binding of Fcγ receptor-bearing cells (immunocytes, etc.) via the Fcγ receptors to the Fc domains of antibodies specifically attached to the cell surface antigens of the target cells. On the other hand, the CDC activity means cytotoxic activity mediated by the complement system.

Whether or not the anti-TMPRSS11E antibody has ADCC activity or has CDC activity can be determined by a method known in the art (e.g., Current protocols in Immunology, Chapter 7. Immunologic studies in humans, Editor, John E, Coligan et al., John Wiley & Sons, Inc., (1993)).

Specifically, effector cells, a complement solution, and target cells are first prepared.

i) Preparation of Effector Cells

The spleens are excised from CBA/N mice or the like, and spleen cells are separated therefrom in RPMI1640 medium (manufactured by Invitrogen Corp.). The cells can be washed with the same medium containing 10% fetal bovine serum (FBS, manufactured by HyClone Laboratories, Inc.) and then adjusted to a cell concentration of $5 \times 10^6$ cells/ml to prepare effector cells.

ii) Preparation of Complement Solution

Baby Rabbit Complement (manufactured by CEDARLANE Laboratories Ltd.) can be diluted 10-fold with a medium (manufactured by Invitrogen Corp.) containing 10% FBS to prepare a complement solution.

iii) Preparation of Target Cells

Cells expressing TMPRSS11E proteins can be cultured at 37° C. for 1 hour, together with 0.2 mCi $^{51}$Cr-sodium chromate (manufactured by GE Healthcare Bio-Sciences Corp.), in a DMEM medium containing 10% FBS to radiolabel the target cells. Cells transformed with TMPRSS11E protein-encoding genes, lung cancer cells, uterine cervix cancer cells, esophagus cancer cells, or the like can be used as the cells expressing TMPRSS11E proteins. After the radiolabeling, the cells can be washed three times with an RPMI1640 medium containing 10% FBS and adjusted to a cell concentration of $2 \times 10^5$ cells/ml to prepare the target cells.

The ADCC or CDC activity can be assayed by a method described below. For the ADCC activity assay, the target cells and the anti-TMPRSS11E antibody (50 μl each) are added to a U-bottom 96-well plate (manufactured by Becton, Dickinson and Company) and reacted for 15 minutes on ice. Then, 100 μl of the effector cells is added to the plate, and the cells are cultured for 4 hours in a $CO_2$ incubator. The final concentration of the antibody is set to 0 or 10 μg/ml. After the culture, 100 μl of the supernatant is collected, and the radioactivity is measured using a gamma counter (COBRA II AUTO-GAMMA, MODEL D5005, manufactured by Packard Instrument Company). The cytotoxic activity (%) can be calculated based on the calculation formula $(A-C)/(B-C) \times 100$ using the obtained value. In the formula, A represents radioactivity (cpm) from each sample; B represents radioactivity (cpm) from a sample supplemented with 1% NP-40 (manufactured by Nacalai Tesque, Inc.); and C represents radioactivity (cpm) from a sample containing only the target cells.

On the other hand, for the CDC activity assay, the target cells and the anti-TMPRSS11E antibody (50 μl each) are added to a flat-bottomed 96-well plate (manufactured by Becton, Dickinson and Company) and reacted for 15 minutes on ice. Then, 100 μl of the complement solution is added to the plate, and the cells are cultured for 4 hours in a $CO_2$ incubator. The final concentration of the antibody is set to 0 or 3 μg/ml. After the culture, 100 μl of the supernatant is collected, and the radioactivity is measured using a gamma counter. The cytotoxic activity can be calculated in the same way as in the ADCC activity assay.

On the other hand, in the assay of cytotoxic activity using antibody conjugates, the target cells and the anti-TMPRSS11E antibody conjugates (50 μl each) are added to a flat-bottomed 96-well plate (manufactured by Becton, Dickinson and Company) and reacted for 15 minutes on ice. The cells are cultured for 1 to 4 hours in a $CO_2$ incubator. The final concentration of the antibody is set to 0 or 3 μg/ml. After the culture, 100 μl of the supernatant is collected, and the radioactivity is measured using a gamma counter. The cytotoxic activity can be calculated in the same way as in the ADCC activity assay.

(2) Conjugated Antibody

The antibody may be conjugated to a cytotoxic substance such as a chemotherapeutic agent, a toxic peptide, or a radioactive chemical. Such a modified antibody (hereinafter, referred to as an antibody conjugate) can be obtained by chemically modifying the obtained antibody. A method for the antibody modification has already been established in the art.

Examples of the chemotherapeutic agent whose cytotoxic activity functions through the conjugation to the anti-TMPRSS11E antibody can include the following chemotherapeutic agents: azaribine, anastrozole, azacytidine, bleomycin, bortezomib, bryostatin-1, busulfan, camptothecin, 10-hydroxycamptothecin, carmustine, Celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine, streptozocin, tamoxifen, taxanes, taxol, testosterone propionate, thalidomide, thioguanine, thiotepa, teniposide, topotecan, uracil mustard, vinblastine, vinorelbine, and vincristine.

The chemotherapeutic agent is preferably a low-molecular chemotherapeutic agent. The low-molecular chemotherapeutic agent is less likely to interfere with the antibody functions even after its conjugation to the antibody. In the present invention, the low-molecular chemotherapeutic agent usually has a molecular weight of 100 to 2000, preferably 200 to 1000. All of the chemotherapeutic agents exemplified above are low-molecular chemotherapeutic agents. These chemotherapeutic agents according to the present invention encompass prodrugs that are converted in vivo to active chemotherapeutic agents. The prodrug activation may be enzymatic conversion or nonenzymatic conversion.

Moreover, the antibody can be modified with the toxic peptide. Examples of the toxic peptide can include the followings: diphtheria toxin A chain (Langone J. J., et al., Methods in Enzymology, 93, 307-308, 1983), *Pseudomonas* exotoxin (Nature Medicine, 2, 350-353, 1996), ricin A chain (Fulton R. J., et al., J. Biol. Chem., 261, 5314-5319, 1986; Sivam G., et al., Cancer Res., 47, 3169-3173, 1987; Cumber A. J. et al., J. Immunol. Methods, 135, 15-24, 1990; Wawrzynczak E. J., et al., Cancer Res., 50, 7519-7562, 1990; and Gheeite V., et al., J. Immunol. Methods, 142, 223-230, 1991), deglycosylated ricin A chain (Thorpe P. E., et al., Cancer Res., 47, 5924-5931, 1987), abrin A chain (Wawrzynczak E. J., et al., Br. J. Cancer, 66, 361-366, 1992; Wawrzynczak E. J., et al., Cancer Res., 50, 7519-7562, 1990; Sivam G., et al., Cancer Res., 47, 3169-3173, 1987; and Thorpe P. E., et al., Cancer Res., 47, 5924-5931, 1987), gelonin (Sivam G., et al., Cancer Res., 47, 3169-3173, 1987; Cumber A. J. et al., J. Immunol. Methods, 135, 15-24, 1990; Wawrzynczak E. J., et al., Cancer Res., 50, 7519-7562, 1990; and Bolognesi A., et al., Clin. exp. Immunol., 89, 341-346, 1992), PAP-s (pokeweed anti-viral protein from seeds) (Bolognesi A., et al., Clin. exp. Immunol., 89, 341-346, 1992), bryodin (Bolognesi A., et al., Clin. exp. Immunol., 89, 341-346, 1992), saporin (Bolognesi A., et al., Clin. exp. Immunol., 89, 341-346, 1992), momordin (Cumber A. J., et al., J. Immunol. Methods, 135, 15-24, 1990; Wawrzynczak E. J., et al., Cancer Res., 50, 7519-7562, 1990; and Bolognesi A., et al., Clin. exp. Immunol., 89, 341-346, 1992), momorcochin (Bolognesi A., et al., Clin. exp. Immunol., 89, 341-346, 1992), dianthin 32 (Bolognesi A., et al., Clin. exp. Immunol., 89, 341-346, 1992), dianthin 30 (Stirpe F., Barbieri L., FEBS letter 195, 1-8, 1986), modeccin (Stirpe F., Barbieri L., FEBS letter 195, 1-8, 1986), viscumin (Stirpe F., Barbieri L., FEBS letter 195, 1-8, 1986), volkensin (Stirpe F., Barbieri L., FEBS letter 195, 1-8, 1986), dodecandrin (Stirpe F., Barbieri L., FEBS letter 195, 1-8, 1986), tritin (Stirpe F., Barbieri L., FEBS letter 195, 1-8, 1986), luffin (Stirpe F., Barbieri L., FEBS letter 195, 1-8, 1986), and trichokirin (Casellas P., et al., Eur. J. Biochem. 176, 581-588, 1988; and Bolognesi A., et al., Clin. exp. Immunol., 89, 341-346, 1992).

In the present invention, the radioactive chemical refers to a chemical containing a radioisotope. Any radioisotope may be used without particular limitations as the radioisotope. For example, $^{32}P$, $^{14}C$, $^{125}I$, $^{3}H$, $^{131}I$, $^{186}Re$, or $^{188}Re$ can be used.

In another aspect, one or two or more low-molecular chemotherapeutic agents and one or two or more toxic peptides can be used in combination in the antibody modification. The anti-TMPRSS11E antibody can be conjugated to the low-molecular chemotherapeutic agent via a covalent or noncovalent bond. A method for preparing such a chemotherapeutic agent-conjugated antibody is known in the art.

A proteinous agent or toxin can be conjugated to the antibody by a genetic engineering approach. Specifically, for example, DNA encoding the toxic peptide and DNA encoding the anti-TMPRSS11E antibody are fused in frame with each other, and this fused DNA can be incorporated into expression vectors to construct recombinant vectors. The vectors are introduced into appropriate host cells, and the resultant transformed cells are cultured. The DNA insert can be expressed by the cells to obtain toxic peptide-conjugated anti-TMPRSS11E antibodies as fusion proteins. For obtaining antibody-fusion proteins, the proteinous agent or toxin is generally located on the C-terminal side of the antibody. A peptide linker may be allowed to intervene between the antibody and the proteinous agent or toxin.

(3) Bispecific antibody

Furthermore, the antibody of the present invention may be a bispecific antibody. The bispecific antibody refers to an antibody having, in the same antibody molecule, variable regions that recognize different epitopes. In the present invention, the bispecific antibody can have antigen-binding sites that recognize different epitopes on the TMPRSS11E molecule. Thus, two such bispecific antibody molecules can bind to one TMPRSS11E molecule. As a result, stronger cytotoxic effect can be expected.

Alternatively, the antibody of the present invention may be a bispecific antibody having antigen-binding sites, one of which recognizes TMPRSS11E and the other of which recognizes a cytotoxic substance. The cytotoxic substance specifically encompasses, for example, a chemotherapeutic agent, a toxic peptide, and a radioactive chemical. Such a bispecific antibody binds to cells expressing TMPRSS11E, while it captures the cytotoxic substance. As a result, the cytotoxic substance can be allowed to directly act on the cells expressing TMPRSS11E. Specifically, the bispecific antibody that recognizes the cytotoxic substance can specifically damage tumor cells and inhibit the growth of the tumor cells.

Moreover, in the present invention, the bispecific antibody combined with an antigen-binding site that recognizes an antigen other than TMPRSS11E can also be used. For example, the antigen-binding site that can be combined with the bispecific antibody recognizes an antigen that is specifically expressed on the surface of target cancer cells, as with TMPRSS11E, but is different from TMPRSS11E.

A method for producing the bispecific antibody is known in the art. For example, two antibodies differing in antigen recognized thereby can be bound to prepare the bispecific antibody. Each of the antibodies bound may be a ½ molecule having heavy and light chains or may be a ¼ molecule consisting of heavy chains. Alternatively, different monoclonal antibody-producing hybridomas can also be fused to prepare fusion cells producing bispecific antibodies. Furthermore, the bispecific antibody can be prepared by a genetic engineering approach.

The avidity of the antibody to antigens can be determined using means known in the art (Antibodies A Laboratory Manual. Ed Harlow, David Lane, Cold Spring Harbor Laboratory, 1988). For example, ELISA (enzyme-linked immunosorbent assay), EIA (enzyme immunoassay), RIA (radioimmunoassay), or fluoroimmunoassay can be used.

(4) Modification of Sugar Chain

The antibody of the present invention may be an antibody having a modified sugar chain. It is known that the cytotoxic activities of antibodies can be enhanced by modifying their sugar chains. For example, the following antibodies are known in the art as the antibody having a modified sugar chain: glycosylated antibodies (WO 99/54342, etc.), antibodies deficient in fucose added to their sugar chains (WO 00/61739, WO 02/31140, etc.), and antibodies having a sugar chain having bisecting GlcNAc (WO 02/79255, etc.).

(5) Internalization Activity

Moreover, the antibody of the present invention may have internalization activity. In the present invention, the "antibody having internalization activity" means an antibody that is transported into cells (cytoplasm, vesicles, other organelles, etc.) through its binding to TMPRSS11E.

Whether or not the antibody has internalization activity can be confirmed by a method generally known by those skilled in the art and can be confirmed by, for example, a method comprising contacting labeling substance-bound anti-TMPRSS11E antibodies with TMPRSS11E-expressing cells and confirming whether or not the labeling substance is incorporated into the cells, or a method comprising contacting cytotoxic substance-conjugated anti-TMPRSS11E antibodies with TMPRSS11E-expressing cells and confirming whether or not the death of the TMPRSS11E-expressing cells is induced.

The antibody having internalization activity can be conjugated to, for example, the cytotoxic substance and used as a pharmaceutical composition such as an anticancer agent described later.

(6) Neutralization Activity

Moreover, the antibody of the present invention may have neutralization activity. In the present invention, the neutralization activity refers to the activity of inhibiting the protease activity of TMPRSS11E. The neutralization activity can be assayed by a method known by those skilled in the art and can be assayed, for example, by a method described in Examples.

4. Preparation of Anti-TMPRSS11E Antibody 4.1 Preparation of Anti-TMPRSS11E Antibody Using Monoclonal Antibody-Producing Hybridoma Monoclonal antibody-producing hybridomas can be prepared according to a technique known in the art as follows: first, animals are immunized with TMPRSS11E proteins or partial peptides thereof (which will be described later) used as sensitizing antigens according to a usual immunization method. The obtained immunocytes are fused with parental cells known in the art by a usual cell fusion method to obtain hybridomas. From these hybridomas, cells producing the antibody of interest can further be screened by a usual screening method to select hybridomas producing the anti-TMPRSS11E antibody. The desired anti-TMPRSS11E monoclonal antibody is obtained from the selected hybridomas. Specifically, the anti-TMPRSS11E monoclonal antibody is prepared as follows:

(1) Preparation of TMPRSS11E Protein

First, TMPRSS11E genes can be expressed to obtain TMPRSS11E proteins used as sensitizing antigens for obtaining antibody. Specifically, the TMPRSS11E-encoding gene sequence is inserted into expression vectors known in the art, with which appropriate host cells are then transformed. Then, the human TMPRSS11E proteins of interest are purified from the host cells or a culture supernatant thereof by a method known in the art. Purified natural TMPRSS11E proteins or fusion proteins comprising the desired partial polypeptide of the TMPRSS11E protein fused with a different polypeptide may be used as immunogens. For example, antibody Fc fragments, peptide tags, and so on can be used for producing the fusion proteins used as immunogens. Expression vectors for the fusion proteins can be prepared by fusing, in frame, two or more genes respectively encoding the desired polypeptide fragments and inserting this fusion gene into expression vectors. The method for preparing the fusion proteins is described in Molecular Cloning 2nd ed. (Sambrook, J. et al., Molecular Cloning 2nd ed., 9.47-9.58, Cold Spring Harbor Lab. Press, 1989).

The TMPRSS11E proteins thus purified can be used as sensitizing antigens used for the immunization of mammals. Partial peptides of TMPRSS11E can also be used as sensitizing antigens. For example, the following peptides can be used as sensitizing antigens:

peptides obtained by chemical synthesis based on the amino acid sequence of human TMPRSS11E;

peptides obtained by incorporating a portion of the TMPRSS11E gene to expression vectors, followed by its expression; and peptides obtained by digesting the TMPRSS11E protein with protease.

The region and size of the partial peptide of TMPRSS11E used are not limited. The number of amino acids constituting the peptide serving as a sensitizing antigen is preferably at least 3 or more, for example, 5 or more or 6 or more. More specifically, peptides of 8 to 50, preferably 10 to 30 residues can be used as sensitizing antigens.

(2) Immunization with TMPRSS11E Protein

Mammals are immunized with the TMPRSS11E proteins or partial peptides thereof as sensitizing antigens. The immunized mammals are not particularly limited. For obtaining the monoclonal antibody by the cell fusion method, it is preferred that the immunized animals should be selected in consideration of compatibility with the parental cells used in cell fusion. In general, rodents are preferable as the immunized animals. Specifically, mice, rats, hamsters, or rabbits can be used as the immunized animals. In addition, monkeys or the like may be used as the immunized animals.

These animals can be immunized with the sensitizing antigens according to a method known in the art. For example, a general method can involve immunizing the mammals with the sensitizing antigens by intraperitoneal or subcutaneous injection. Specifically, the sensitizing antigens are administered to the mammals several times at 4- to 21-day intervals. The sensitizing antigens are diluted with PBS (phosphate-buffered saline), saline, or the like at an appropriate dilution ratio and used in the immunization. Furthermore, the sensitizing antigens may be administered together with an adjuvant. For example, the antigens can be mixed with a Freund's complete adjuvant for emulsification to prepare sensitizing antigens. Moreover, an appropriate carrier can be used in the immunization with the sensitizing antigens. Particularly, when partial peptides having a small molecular weight are used as the sensitizing antigens, it is preferred that the sensitizing antigen peptides should be bound to carrier proteins such as albumin or keyhole limpet hemocyanin and used in the immunization.

(3) DNA Immunization

The monoclonal antibody can also be obtained by DNA immunization. The DNA immunization is an immunostimulation method comprising: immunizing animals by the administration of vector DNA that has been constructed in a form capable of expressing antigenic protein-encoding genes in the immunized animals; and allowing the immunized animals to express the immunizing antigens in vivo. The DNA immunization can be expected to be superior to general immunization methods using the administration of protein antigens as follows: it can provide immunostimulation with membrane protein (e.g., TMPRSS11E) structures maintained; and it eliminates the need of purifying immunizing antigens.

For obtaining the monoclonal antibody of the present invention by the DNA immunization, first, animals are immunized by the administration of TMPRSS11E protein expression vector DNA. TMPRSS11E-encoding DNA can be synthesized by a method known in the art such as PCR. The obtained DNA is inserted into appropriate expression vectors, with which animals are immunized by administration. For example, commercially available expression vectors such as pcDNA3.1 can be used as the expression vectors. A method generally used can also be used as a method for administering the vectors to the animals. For example, gold particles with the expression vectors adsorbed onto can be inserted into cells using a gene gun to perform DNA immunization.

(4) Preparation of Hybridoma

Increase in the amount of the desired antibody in the serum of the mammals thus immunized is confirmed. Then, immunocytes are collected from the mammals and subjected to cell fusion. Particularly, spleen cells can be used as preferable immunocytes.

Mammalian myeloma cells are used as cells fused with the immunocytes. It is preferred that the myeloma cells should have an appropriate selection marker for screening. The selection marker refers to a character that can survive (or cannot survive) under particular culture conditions. For example, hypoxanthine-guanine phosphoribosyltransferase deficiency (hereinafter, abbreviated to HGPRT deficiency) or thymidine kinase deficiency (hereinafter, abbreviated to TK deficiency) is known in the art as the selection marker. Cells having the HGPRT or TK deficiency is sensitive to hypoxanthine-aminopterin-thymidine (hereinafter, abbreviated to HAT-sensitive). The HAT-sensitive cells are killed in a HAT selective medium because they cannot synthesize DNA. By contrast, these cells, when fused with normal cells, can grow even in the HAT selective medium because they can continue DNA synthesis by use of the salvage pathway of the normal cells.

The cells having the HGPRT or TK deficiency can be selected using a medium containing 6-thioguanine or 8-azaguanine (hereinafter, abbreviated to 8AG) or 5'-bromodeoxyuridine, respectively. The normal cells are killed in such a medium because they incorporate these pyrimidine analogs into their DNAs. By contrast, the cells deficient in these enzymes can survive in the selective medium because they cannot incorporate the pyrimidine analogs therein. In addition, a selection marker called G418 resistance imparts, to cells, 2-deoxystreptamine antibiotic (gentamicin analog) resistance via a neomycin resistance gene. Various myeloma cells suitable for the cell fusion are known in the art. For example, the following myeloma cells can be used in the production of the monoclonal antibody according to the present invention:

P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S. J. Exp. Med. (1978) 148, 313-323), and R210 (Galfre, G. et al., Nature (1979) 277, 131-133).

Basically, the cell fusion of the immunocytes with the myeloma cells is performed according to a method known in the art, for example, the method of Kohler and Milstein et al. (Kohler. G. and Milstein, C., Methods Enzymol. (1981) 73, 3-46).

More specifically, the cell fusion can be performed, for example, in a usual nutrient culture medium in the presence of a cell fusion promoter. For example, polyethylene glycol (PEG) or hemagglutinating virus of Japan (HVJ) can be used as the fusion promoter. Furthermore, an auxiliary such as dimethyl sulfoxide can also be added thereto, if desired, for enhancing fusion efficiency.

The ratio between the immunocytes and the myeloma cells used can be set arbitrarily. For example, it is preferred that the amount of the immunocytes should be set to 1 to 10 times that of the myeloma cells. For example, RPMI1640 or MEM culture medium suitable for the growth of the myeloma cell line as well as usual culture media used in this kind of cell culture can be used as the culture medium used in the cell fusion. Furthermore, a solution supplemented with serum (e.g., fetal calf serum (FCS)) can be added to the culture medium.

For the cell fusion, the immunocytes and the myeloma cells are well mixed in the predetermined amounts in the culture medium, and these mixed cells are mixed with a PEG solution preheated to approximately 37° C. to form the fusion cells (hybridomas) of interest. In the cell fusion method, for example, PEG with an average molecular weight on the order of 1000 to 6000 can usually be added at a concentration of 30 to 60% (w/v). Subsequently, the appropriate culture medium exemplified above is sequentially added to the hybridomas, and the mixture is centrifuged, followed by removal of the supernatant. This procedure is repeated to remove the cell fusion agents or the like unfavorable for hybridoma growth.

The hybridomas thus obtained can be selected by use of a selective culture medium appropriate for the selection marker of the myeloma cells used in the cell fusion. For example, the cells having the HGPRT or TK deficiency can be selected by culturing the hybridomas in a HAT culture medium (culture medium containing hypoxanthine, aminopterin, and thymidine). Specifically, when HAT-sensitive myeloma cells are used in the cell fusion, only cells successfully fused with normal cells can be grown selectively in the HAT culture medium. The culture using the HAT culture medium is continued for a time long enough to kill cells (non-fused cells) other than the hybridomas of interest. Specifically, the culture can generally be performed for a few days to a few weeks to select the hybridomas of interest. Subsequently, hybridomas producing the antibody of interest can be screened and cloned as single clones by a usual limiting dilution method.

The screening of the antibody of interest and cloning as single clones thereof can be performed preferably by a screening method based on antigen-antibody reaction known in the art. For example, the antigens are bound to a carrier such as beads made of polystyrene or the like or a commercially available 96-well microtiter plate and reacted with the culture supernatant of the hybridomas. Subsequently, the carrier is washed and then reacted with enzyme-labeled secondary antibodies or the like. If the culture supernatant contains the antibody of interest reactive with the sensitizing antigens, the secondary antibodies bind to the carrier via this antibody. Finally, the secondary antibodies bound with the carrier can be detected to determine the presence of the antibody of interest in the culture supernatant. The hybridomas producing the desired antibody capable of binding to the antigen can be cloned by a limiting dilution method or the like. In this screening, the TMPRSS11E proteins used in the immunization or TMPRSS11E proteins substantially identical thereto can be used preferably as the antigens. For example, cell lines expressing TMPRSS11E, soluble TMPRSS11E, or the like can be used as the antigens.

A method described in International Publication No. WO 03/104453 may be used in the production of the antibody against human TMPRSS11E.

Moreover, in addition to the method for obtaining the hybridomas by immunizing non-human animals with the antigens, human lymphocytes may be sensitized with the antigens to obtain the antibody of interest. Specifically, the human lymphocytes are first sensitized with the TMPRSS11E proteins in vitro. Subsequently, the sensitized lymphocytes are fused with appropriate fusion partners. For example, human-derived myeloma cells capable of dividing permanently can be used as the fusion partners (see Japanese Patent Publication No. 1-59878).

Furthermore, the anti-TMPRSS11E human antibody can also be obtained by administering the TMPRSS11E proteins as antigens to transgenic animals having all repertoires of human antibody genes or by immunizing the animals with DNA that has been constructed to express TMPRSS11E in the animals. Antibody-producing cells from the immunized animals can be immortalized by treatment such as cell fusion with appropriate fusion partners or infection with Epstein-Barr virus. From the immortalized cells thus obtained, human antibodies against the TMPRSS11E protein can be isolated (see International Publication Nos. WO 94/25585, WO 93/12227, WO 92/03918, and WO 94/02602). Furthermore, the immortalized cells can also be cloned as cells producing antibodies having the reaction specificity of interest. When transgenic animals are used as the immunized animals, the immune systems of the animals recognize human TMPRSS11E as foreigners. Thus, the human antibodies against human TMPRSS11E can be obtained easily.

(5) Obtainment of Monoclonal Antibody from Hybridoma

The monoclonal antibody-producing hybridomas thus prepared can be subcultured in a usual culture medium. Moreover, the hybridomas can also be stored over a long period in liquid nitrogen.

The hybridomas are cultured according to a usual method, and the monoclonal antibody of interest can be obtained from the culture supernatant thereof. Alternatively, the hybridomas are administered to mammals compatible therewith and grown, and the monoclonal antibody can also be obtained in the form of ascitic fluids. The former method is suitable for obtaining highly pure antibodies.

4.2 Preparation of Anti-TMPRSS11E Antibody by Genetic Engineering Approach (1) Cloning of Antibody Gene The antibody may be prepared by a genetic engineering approach using antibody genes cloned from antibody-producing cells. The cloned antibody genes can be incorporated into appropriate vectors and expressed as antibodies by the transformation of hosts. Methods for the antibody gene isolation, the introduction into vectors, and the transformation of host cells have already been established (see e.g., Vandamme, A. M. et al., Eur. J. Biochem. (1990) 192, 767-775).

For example, cDNAs encoding the variable regions of the anti-TMPRSS11E antibody can be obtained from the anti-TMPRSS11E antibody-producing hybridoma cells. For this purpose, usually, total RNAs are first extracted from the hybridomas. For example, the following methods can be used as a method for mRNA extraction from the cells: guanidine ultracentrifugation method (Chirgwin, J. M. et al., Biochemistry (1979) 18, 5294-5299), and AGPC method (Chomczynski, P. et al., Anal. Biochem. (1987) 162, 156-159).

The extracted mRNAs can be purified using mRNA Purification Kit (manufactured by GE Healthcare Bio-Sciences Corp.) or the like. Alternatively, a kit for directly extracting total mRNAs from cells is also commercially available, such as QuickPrep mRNA Purification Kit (manufactured by GE Healthcare Bio-Sciences Corp.). The total mRNAs may be obtained from the hybridomas using such a kit. From the obtained mRNAs, antibody variable region-encoding cDNAs can be synthesized using reverse transcriptase. In this procedure, arbitrary 15- to 30-base sequences selected from sequences common to the antibody gene can be used as primers. The cDNAs can be synthesized using AMV Reverse Transcriptase First-strand cDNA Synthesis Kit (manufactured by SEIKAGAKU CORP.) or the like. Moreover, 5'-Ampli FINDER RACE Kit (manufactured by Clontech Laboratories, Inc.) and 5'-RACE method using PCR (Frohman, M. A. et al., Proc. Natl. Acad. Sci. USA (1988) 85, 8998-9002; and Belyaysky, A. et al., Nucleic Acids Res. (1989) 17, 2919-2932) can be used for the cDNA synthesis and amplification. Furthermore, appropriate restriction sites described later can be introduced into both ends of the cDNAs in the course of such cDNA synthesis.

From the obtained PCR products, the cDNA fragments of interest are purified and subsequently ligated with vector DNAs. The recombinant vectors thus prepared are introduced into *E. coli* or the like. After colony selection, the desired recombinant vectors can be prepared from *E. coli* that has formed the colony. Then, the nucleotide sequence of the cDNA can be confirmed by a method known in the art, for example, a dideoxynucleotide chain termination method.

Moreover, cDNA libraries may be used for obtaining the antibody variable region-encoding genes. First, cDNAs are synthesized with mRNAs extracted from the antibody-producing cells as templates to obtain cDNA libraries. A commercially available kit is conveniently used in the cDNA library synthesis. In actuality, mRNAs from only a small number of cells are obtained in very small amounts. Therefore, direct purification thereof results in low yields. Thus, carrier RNAs shown to be free from the antibody genes are usually added thereto, followed by purification. Alternatively, when RNAs can be extracted in given amounts, efficient extraction can be achieved only using those from the antibody-producing cells. The addition of the carrier RNAs may be unnecessary for RNA extraction from, for example, 10 or more or 30 or more, preferably 50 or more antibody-producing cells.

The antibody genes are amplified by PCR with the obtained cDNA libraries as templates. Primers for the PCR amplification of the antibody genes are known in the art. For example, primers for human antibody gene amplification can be designed based on the disclosure of the paper (J. Mol. Biol. (1991) 222, 581-597) or the like. These primers have a nucleotide sequence differing on an immunoglobulin subclass basis. Thus, when cDNA libraries whose subclass is unknown are used as templates, PCR is performed in consideration of every possibility.

Specifically, for example, for the purpose of obtaining human IgG-encoding genes, primers can be used, which are capable of respectively amplifying genes encoding γ1 to γ5 heavy chains and κ and λ light chains. For amplifying IgG variable region genes, 3' primers are generally used, which anneal to a portion corresponding to the hinge region. On the other hand, primers appropriate for each subclass can be used as 5' primers.

The PCR products obtained from the primers for gene amplification for these heavy and light chain subclasses are prepared as their respective independent libraries. The libraries thus synthesized can be used to reshape immunoglobulins comprising the heavy and light chains in combination. The antibody of interest can be screened with the avidity of the reshaped immunoglobulins for TMPRSS11E as an index.

(2) Introduction of Antibody Gene into Host Cell

For producing the anti-TMPRSS11E antibody, the cloned antibody genes can be incorporated into expression vectors such that these genes are expressed under the control of expression control regions. The expression control regions for antibody expression encompass, for example, enhancers and promoters. Subsequently, appropriate host cells can be transformed with these expression vectors to obtain recombinant cells expressing the anti-TMPRSS11E antibody-encoding DNA.

For the antibody gene expression, the antibody heavy chain- and light chain-encoding DNAs can be incorporated separately in different expression vectors. The same host cell can be co-transfected with the heavy chain- and light chain-incorporated vectors and thereby allowed to express antibody molecules comprising the heavy and light chains. Alternatively, the heavy chain- and light chain-encoding DNAs may be incorporated in single expression vectors, with which host cells are transformed (see International Publication No. WO 94/11523).

The hosts and the expression vectors for introducing the isolated antibody genes into appropriate hosts for antibody preparation are known in the art as many combinations. All of these expression systems can be applied to the present invention. When eukaryotic cells are used as the hosts, animal, plant, or fungus cells can be used. Specifically, examples of the animal cells that can be used in the present invention can include the following cells:

i) mammalian cells: CHO, COS, myeloma, BHK (baby hamster kidney), Hela, Vero, HEK293, Ba/F3, HL-60, Jurkat, and SK-HEP1 cells;
ii) amphibian cells: *Xenopus* oocytes; and
iii) insect cells: sf9, sf21, and Tn5 cells.

For the plant cells, antibody gene expression systems are known in the art, which involve cells derived from the genus *Nicotiana* (e.g., *Nicotiana tabacum*). Cultured callus cells can be used in the plant cell transformation.

Furthermore, the following cells can be used as the fungus cells:

cells derived from: yeasts such as the genus *Saccharomyces* (e.g., *Saccharomyces cerevisiae*) and the genus *Pichia* (e.g., *Pichia pastoris*); and filamentous fungi such as the genus *Aspergillus* (e.g., *Aspergillus niger*).

Alternatively, antibody gene expression systems using prokaryotic cells are also known in the art. For example, when bacterial cells are used, bacterial cells derived from *E. coli*, *Bacillus subtilis*, or the like can be used in the present invention.

When the mammalian cells are used, a useful promoter routinely used, the antibody gene to be expressed, and a poly A signal located 3'-downstream thereof can be ligated functionally for the gene expression. Examples of the promoter/enhancer can include a human cytomegalovirus immediate early promoter/enhancer.

Moreover, in addition, virus promoters/enhancers and mammalian cell-derived promoters/enhancers (e.g., human elongation factor 1α (HEF1α)) can be used in the antibody expression. Examples of the viruses whose promoter/enhancer can be used can specifically include retrovirus, polyomavirus, adenovirus, and simian virus 40 (SV40).

The SV40 promoter/enhancer can be used according to the method of Mulligan et al. (Nature (1979) 277, 108). Moreover, the HEF1α promoter/enhancer can be used easily in the gene expression of interest by the method of Mizushima et al. (Nucleic Acids Res. (1990) 18, 5322).

When antibodies are produced using animal cells, the signal sequence of the heavy chain or light chain gene of the antibody is preferably used as a signal sequence required for extracellular secretion. Moreover, the signal sequence of a secretory protein such as IL-3 or IL-6 may be used.

For the *E. coli*, a useful promoter routinely used, a signal sequence for antibody secretion, and the antibody gene to be expressed can be ligated functionally for the gene expression. Examples of the promoter can include lacZ and araB promoters. The lacZ promoter can be used according to the method of Ward et al. (Nature (1989) 341, 544-546; and FASEBJ. (1992) 6, 2422-2427). Alternatively, the araB promoter can be used in the gene expression of interest by the method of Better et al. (Science (1988) 240, 1041-1043).

When antibodies are produced in *E. coli* periplasm, a pelB signal sequence (Lei, S. P. et al., J. Bacteriol. (1987) 169, 4379) may be used as the signal sequence for antibody secretion. Then, the antibodies produced in the periplasm are separated and then refolded by use of protein denaturants such as urea and guanidine hydrochloride such that the resultant antibodies have the desired avidity.

A replication origin derived from SV40, polyomavirus, adenovirus, bovine papillomavirus (BPV), or the like can be used as a replication origin inserted in the expression vectors. Furthermore, a selection marker can be inserted in the expression vectors for increasing a gene copy number in the host cell systems. Specifically, selection markers can be used, such as aminoglycoside phosphotransferase (APH) genes, thymidine kinase (TK) genes, *E. coli* xanthine-guanine phosphoribosyltransferase (Ecogpt) genes, and dihydrofolate reductase (dhfr) genes.

(3) Obtainment of Antibody from Host Cell

The host cells are transformed with these expression vectors, and the transformed host cells are then cultured in vitro or in vivo to produce the antibody of interest. The culture of the host cells is performed according to a method known in the art. For example, a DMEM, MEM, RPMI1640, or IMDM culture medium can be used and may be used in combination with a solution supplemented with serum such as fetal calf serum (FCS).

The antibodies thus expressed and produced can be purified by using, alone or in appropriate combination, usual protein purification methods known in the art. For example, affinity or chromatography columns (e.g., protein A columns), filters, ultrafiltration, salting-out, and dialysis can be selected and combined appropriately to separate and purify the antibodies (Antibodies A Laboratory Manual. Ed Harlow, David Lane, Cold Spring Harbor Laboratory, 1988).

4.3 Antibody Production by Transgenic Animal

In addition to the host cells, transgenic animals can also be used in the recombinant antibody production. Specifically, the antibody of interest can be obtained from animals transfected with the genes encoding this antibody of interest. For example, the antibody genes can be inserted in frame into genes encoding proteins specifically produced in milk to construct fusion genes. For example, goat β casein can be used as the proteins secreted into milk. DNA fragments containing the fusion genes having the antibody gene insert are injected into goat embryos, which are in turn introduced into female goats. From milk produced by transgenic goats (or progeny thereof) brought forth by the goats that have received the embryos, the desired antibody can be obtained as a fusion protein with the milk protein. Moreover, in the transgenic goats, hormone can be used appropriately for increasing the amount of milk containing the desired antibody produced from the transgenic goats (Ebert, K. M. et al., Bio/Technology (1994) 12, 699-702).

5. Pharmaceutical Composition

TMPRSS11E is highly expressed in a specific manner in tissues of cancer such as lung cancer, uterine cervix cancer, or esophagus cancer. The anti-TMPRSS11E antibody has cancer cell-specific cytotoxic activity. Thus, the anti-TMPRSS11E antibody is useful in the treatment of these cancers expressing TMPRSS11E.

Specifically, the present invention provides a pharmaceutical composition comprising the antibody binding to a TMPRSS11E protein as an active ingredient. In an embodiment, the pharmaceutical composition is a cell growth inhibitor, particularly, an anticancer agent. It is preferred that the cell growth inhibitor and the anticancer agent of the present invention should be administered to a subject having cancer or possibly having cancer.

The anti-TMPRSS11E antibody used in the pharmaceutical composition (e.g., anticancer agent) of the present invention is not particularly limited, and, for example, any of the anti-TMPRSS11E antibodies described above can be used.

In the present invention, the phrase "comprising the antibody binding to TMPRSS11E as an active ingredient" means comprising the anti-TMPRSS11E antibody as a main active ingredient and does not limit the content of the anti-TMPRSS11E antibody.

The pharmaceutical composition of the present invention may comprise the cytotoxic substance-conjugated anti-TMPRSS11E antibody as an active ingredient. This pharmaceutical composition can be used as a cell growth inhibitor, particularly, an anticancer agent. It is preferred that the cell growth inhibitor and the anticancer agent of the present invention should be administered to a subject having cancer or possibly having cancer.

In the present invention, the phrase "comprising the cytotoxic substance-conjugated anti-TMPRSS11E antibody as an active ingredient" means comprising the cytotoxic substance-conjugated anti-TMPRSS11E antibody as a main active ingredient and does not limit the content of the cytotoxic substance-conjugated anti-TMPRSS11E antibody.

When the disease targeted by the pharmaceutical composition of the present invention is cancer, the targeted cancer is not particularly limited and is preferably lung cancer, uterine cervix cancer, or esophagus cancer. The cancer may be any of primary foci and metastatic foci.

The pharmaceutical composition of the present invention can be administered either orally or parenterally to a patient. Parenteral administration is preferable. Specific examples of such an administration method include injection, transnasal, pulmonary, and transdermal administrations. Examples of the injection administration include intravenous, intramuscular, intraperitoneal, and subcutaneous injections, through which the pharmaceutical composition of the present invention can be administered systemically or locally. Moreover, the administration method can be selected appropriately according to the age or symptoms of the patient. The dose of the pharmaceutical composition of the present invention can be selected from among a dose range of, for example, 0.0001 mg to 1000 mg per kg body weight per dosing. Alternatively, the dose can be selected from among a range of, for example, 0.001 to 100000 mg per patient. However, the pharmaceutical composition of the present invention is not limited to these doses.

The pharmaceutical composition of the present invention can be formulated according to a standard method (e.g., Remington's Pharmaceutical Science, latest edition, Mark Publishing Company, Easton, U.S.A) and may additionally contain pharmaceutically acceptable carriers or additives. Examples thereof include, but not limited thereto, surfactants, excipients, coloring agents, flavoring agents, preservatives, stabilizers, buffers, suspending agents, tonicity agents, binders, disintegrants, lubricants, flow promoters, and corrigents. Other carriers routinely used can be used appropriately. Specific examples of the carriers can include light anhydrous silicic acid, lactose, crystalline cellulose, mannitol, starch, carmellose calcium, carmellose sodium, hydroxypropylcellulose, hydroxypropylmethylcellulose, polyvinyl acetal diethylaminoacetate, polyvinyl pyrrolidone, gelatin, middle chain fatty acid triglyceride, polyoxyethylene hydrogenated castor oil 60, white sugar, carboxymethylcellulose, corn starch, and inorganic salts.

The anti-TMPRSS11E antibody of the present invention can cause damage to TMPRSS11E-expressing cells or inhibition of their growth by contact with the TMPRSS11E-expressing cells. Such a method using the anti-TMPRSS11E antibody is also incorporated in the scope of the present invention. The antibody used is not particularly limited, and, for example, any of the antibodies described above can be used. The cells to which the anti-TMPRSS11E antibody binds are not particularly limited as long as the cells express TMPRSS11E. In the present invention, the TMPRSS11E-expressing cells are preferably cancer cells, more preferably lung cancer cells, uterine cervix cancer cells, or esophagus cancer cells. The method can also be applied to any of the primary foci and metastatic foci of these cancers.

In the present invention, the "contact" is performed, for example, by adding the antibody to a culture medium of TMPRSS11E-expressing cells cultured in a test tube. Moreover, in the present invention, the "contact" is also performed by administering the anti-TMPRSS11E antibody to non-human animals implanted with TMPRSS11E-expressing cells in their bodies or to animals endogenously having cancer cells expressing TMPRSS11E.

Methods shown below are preferably used as methods for evaluating or determining cytotoxicity caused in the TMPRSS11E-expressing cells by the contact of the anti-TMPRSS11E antibody. Examples of methods for evaluating or determining the cytotoxic activity in vitro can include assay for ADCC activity or CDC activity. Whether or not the anti-TMPRSS11E antibody has ADCC activity or has CDC activity can be determined by a method known in the art (e.g., Current protocols in Immunology, Chapter 7. Immunologic studies in humans, Editor, John E, Coligan et al., John Wiley & Sons, Inc., (1993)). In the activity assay, antibodies that have an isotype identical to that of the anti-TMPRSS11E antibody and are free from the cytotoxic activity are used as control antibodies in the same way as in the anti-TMPRSS11E antibody. When the anti-TMPRSS11E antibody exhibits stronger cytotoxic activity than that of the control antibodies, the anti-TMPRSS11E antibody can be determined to have the activity.

The isotype of an antibody is specified based on the sequence of the heavy chain constant region in the amino acid sequence of this antibody. The antibody isotype is finally determined depending on class switching caused by genetic recombination on the chromosome during the maturation of antibody-producing B cells in vivo. Difference in isotype reflects difference between the physiological/pathological functions of antibodies. Specifically, for example, it is known that the strength of cytotoxic activity is influenced not only by antigen expression levels but by antibody isotypes. Thus, for the cytotoxic activity assay, it is preferred that the antibodies used as controls should have an isotype identical to that of the antibody to be tested.

Moreover, for evaluating or determining the cytotoxic activity in vivo, for example, TMPRSS11E-expressing cancer cells are intradermally or subcutaneously transplanted to non-human test animals. Then, the antibody to be tested is intravenously or intraperitoneally administered thereto on a daily basis or at a few day-intervals from the administration day or the next day. The cytotoxic activity can be determined by measuring tumor sizes over time. Control antibodies having an isotype identical thereto are administered in the same way as in the in vitro evaluation. When the anti-TMPRSS11E antibody-administered group has a significantly smaller tumor size than that of the control antibody-administered group, the anti-TMPRSS11E antibody can be determined to have the cytotoxic activity. When mice were used as the non-human test animals, nude (nu/nu) mice can be used preferably, which are genetically deficient in thymus gland and thus lack the functions of T lymphocytes. The use of the mice can exclude the involvement of the T lymphocytes in the test animals in the evaluation/determination of cytotoxic activity of administered antibodies.

6. Diagnostic Drug (Diagnosis Method)

The present invention also provides a method for diagnosing cancer, comprising detecting a TMPRSS11E protein or a TMPRSS11E protein-encoding gene. TMPRSS11E has been confirmed to have remarkably increased expression in various cancer tissues or cancer cell lines. Thus, TMPRSS11E is useful as a marker for specifically detecting cancer.

One specific example of the diagnosis method of the present invention can include a method for diagnosing cancer, comprising the following steps:
(a) preparing a sample isolated from a test subject; and
(b) detecting the expression level of a TMPRSS11E protein or a TMPRSS11E gene in the sample.

The method of the present invention may further comprise the step:
(c) evaluating the possibility that the test subject has cancer, based on the expression level of the TMPRSS11E protein or the TMPRSS11E gene.

6.1 Detection of TMPRSS11E Protein or TMPRSS11E Protein-Encoding Gene

In one aspect of the method of the present invention, cancer is diagnosed by detecting a TMPRSS11E protein in a sample. It is preferred that the TMPRSS11E protein detection should be performed using an antibody that recognizes the TMPRSS11E protein.

In the present invention, the detection encompasses quantitative or qualitative detection. Examples of the qualitative detection can include the following assays: simple assay on the presence or absence of the TMPRSS11E protein, assay on the presence or absence of more than a predetermined amount of the TMPRSS11E protein, and assay comprising comparing the amount of the TMPRSS11E protein with that contained in another sample (e.g., a control sample).

On the other hand, examples of the quantitative detection can include measurement of a TMPRSS11E protein concentration and measurement of the amount of the TMPRSS11E protein.

The test sample according to the present invention is not particularly limited as long as the sample is likely to contain the TMPRSS11E protein. Specifically, samples collected from living bodies such as mammals are preferable. Samples collected from humans are more preferable. Specific examples of the test sample can include blood, interstitial fluid, plasma, extravascular fluid, cerebrospinal fluid, synovial fluid, pleural fluid, serum, lymph, saliva, urine, and tissues. The sample is preferably a preparation on which tissues or cells collected from living body is fixed, or a sample obtained from the test sample, such as a cell culture medium.

The cancer diagnosed by the present invention may be any cancer without particular limitations. Specific examples thereof can include lung cancer, uterine cervix cancer, and esophagus cancer. In the present invention, any of primary foci and metastatic foci of these cancers can be diagnosed.

In the present invention, when the protein is detected in the test sample, cancer is diagnosed with its level as an index. Specifically, when the amount of the TMPRSS11E protein detected in the test sample is larger than that of a negative control or a healthy individual, the test subject is shown to have cancer or possibly have cancer in the future. Specifically, the present invention relates to a method for diagnosing cancer, comprising the following steps:
(1) detecting the expression level of TMPRSS11E in a biological sample collected from a test subject, and
(2) comparing the expression level of TMPRSS11E detected in the step (1) with that of a control, wherein when the expression level of TMPRSS11E is higher than that of the control, the test subject is determined to have cancer.

In the present invention, the control refers to a reference sample for comparison and encompasses negative controls and biological samples of healthy individuals. The negative controls can be obtained by collecting biological samples of healthy individuals and mixing them, if necessary. The expression level of TMPRSS11E in the control can be detected in parallel with the detection of the expression level of TMPRSS11E in the biological sample of the test subject. Alternatively, the expression level of TMPRSS11E in a large number of biological samples of healthy individuals can be detected in advance to statistically determine the standard expression level in the healthy individuals. Specifically, for example, mean±2×standard deviation (S.D.) or mean±3× standard deviation (S.D.) can also be used as the standard value. Statistically, the mean±2×standard deviation (S.D.) and the mean±3×standard deviation (S.D.) include 80% and 90% of the healthy individuals, respectively.

Alternatively, the expression level of TMPRSS11E in the control can be set using an ROC curve. The ROC curve, or receiver operating characteristic curve, is a graph showing detection sensitivity in the ordinate and false positive rates (i.e., "1-specificity") in the abscissa. In the present invention, the ROC curve can be obtained by plotting changes in sensitivity and false positive rate at a series of varying reference values for determining the expression level of TMPRSS11E in biological samples.

The "reference value" for obtaining the ROC curve is a numeric value temporarily used for statistical analysis. In general, the "reference value" for obtaining the ROC curve is serially varied within a range which can cover all selectable reference values. For example, the reference value can be varied between the minimal and maximal measured values of TMPRSS11E in a population to be analyzed.

A standard value that can be expected to offer the desired detection sensitivity and precision can be selected based on the obtained ROC curve. The standard value statistically set based on the ROC curve or the like is also called a cut-off value. In a method for detecting cancer based on the cut-off value, the step (2) comprises comparing the expression level of TMPRSS11E detected in the step (1), with the cut-off value. Then, when the expression level of TMPRSS11E detected in the step (1) is higher than the cut-off value, cancer is detected in the test subject.

In the present invention, the expression level of TMPRSS11E can be determined by an arbitrary method. Specifically, the expression level of TMPRSS11E can be determined by evaluating the amount of TMPRSS11E mRNA, the amount of the TMPRSS11E protein, or the biological activity of the TMPRSS11E protein. The amount of the TMPRSS11E mRNA or protein can be determined by a method as described in the present specification.

In the present invention, the test subject is particularly preferably a human. When a non-human animal is used as the test subject, a TMPRSS11E protein derived from this animal species is detected.

A method for detecting the TMPRSS11E protein contained in the test sample is not particularly limited and is preferably detection by an immunological method using the anti-TMPRSS11E antibody as exemplified below:
enzyme-linked immunosorbent assay (ELISA),
radioimmunoassay (RIA),
enzyme immunoassay (EIA),
fluoroimmunoassay (FIA),
luminescent immunoassay (LIA),
immunoprecipitation (IP),
turbidimetric immunoassay (TIA),
western blotting (WB),
immunohistochemical (IHC) method,
immunodiffusion (SRID),
dot blot, and
slot blot.

Among these approaches, the immunohistochemical (IHC) method is a immunological assay method preferable as a method for diagnosing cancer, comprising the step of detecting TMPRSS11E proteins in sections in which a tissue or cells obtained from a patient having cancer is fixed. The immunological methods such as the immunohistochemical (IHC) method are methods generally known by those skilled in the art.

Since TMPRSS11E is a membrane protein with enhanced expression specific for cancer cells, cancer cells or cancer tissues can be detected using the anti-TMPRSS11E antibody. Cancer cells contained in cells or tissues collected from living bodies are detected by the immunohistological analysis.

In another preferable aspect, cancer tissues can also be detected in vivo using the anti-TMPRSS11E antibody. This method specifically comprises the steps of: (1) administering, to a test subject, a labeling substance (e.g., radioisotope)-labeled antibody binding to a TMPRSS11E protein; and (2) detecting the accumulation of the labeling substance. The antibody can be labeled detectably for tracing the antibody administered into the living body. For example, the antibody can be labeled with a fluorescent or luminescent material or a radioisotope, and its in vivo behavior can be traced. The antibody labeled with the fluorescent or luminescent material can be observed using an endoscope or peritoneoscope. The localization of the antibody can be imaged by tracing the radioactivity of the radioisotope. In the present invention, the in vivo localization of the anti-TMPRSS11E antibody represents the presence of cancer cells.

A positron-emitting nuclide can be used as the radioisotope for labeling the antibody for in vivo cancer detection. For example, the antibody can be labeled with a positron-emitting nuclide such as 18F, 55Co, 64Cu, 66Ga, 68Ga, 76Br, 89Zr, and 124I. A method known in the art (Acta Oncol. 32, 825-830, 1993) can be used in the labeling of the anti-TMPRSS11E antibody with these positron-emitting nuclides.

The anti-TMPRSS11E antibody labeled with the positron-emitting nuclide is administered to humans or animals. Then, radiation emitted by the radionuclide is measured ex vivo using PET (positron emission tomograph) and converted to images by a computed tomographic approach. The PET is an apparatus for noninvasively obtaining data about in vivo drug behavior or the like. The PET can quantitatively image radiation intensity as signal intensity. By such use of the PET, antigen molecules highly expressed in particular cancer can be detected without collecting samples from patients. The anti-TMPRSS11E antibody may be radiolabeled with a short-life nuclide using a positron-emitting nuclide such as 11C, 13N, 15O, 18F, and 45Ti, in addition to the nuclides described above.

Research and development have been pursued as to, for example, techniques of producing short-life nuclides using a medical cyclotron and the nuclides described above or producing short-life radiolabeling compounds. The anti-TMPRSS11E antibody can be labeled with various radioisotopes by these techniques. The anti-TMPRSS11E antibody administered to patients accumulates in primary foci and metastatic foci according to the specificity of the anti-TMPRSS11E antibody for pathological tissues at each site. When the anti-TMPRSS11E antibody is labeled with the positron-emitting nuclide, its radioactivity can be detected to detect the presence of the primary foci and the metastatic foci based on the localization of the radioactivity. An active value of gamma radiation or positron emission of 25 to 4000 keV can be used appropriately for the diagnostic use. Moreover, therapeutic effect can also be expected by selecting an appropriate nuclide and administering the selected nuclide in larger amounts. A nuclide that provides a value of gamma radiation or positron emission of 70 to 700 keV can be used for obtaining anticancer effect attributed to radiation.

6.2 Detection of TMPRSS11E Protein-Encoding Polynucleotide

In an alternative aspect of the method of the present invention, the expression of the TMPRSS11E polynucleotide is detected. In the present invention, the detected polynucleotide is not particularly limited and is preferably mRNA. In the present invention, the detection encompasses quantitative or qualitative detection. Examples of the qualitative detection can include the following assay procedures: simple assay on the presence or absence of the TMPRSS11E mRNA, assay on the presence or absence of more than a predetermined amount of the TMPRSS11E mRNA, and assay comprising comparing the amount of the TMPRSS11E mRNA with that contained in another sample (e.g., a control sample).

On the other hand, examples of the quantitative detection can include measurement of a TMPRSS11E mRNA concentration and measurement of the amount of the TMPRSS11E mRNA.

In the present invention, an arbitrary sample likely to contain the TMPRSS11E mRNA can be used as the test sample. Samples collected from living bodies such as mammals are preferable. Samples collected from humans are more preferable. Specific examples of the test sample can include blood, interstitial fluid, plasma, extravascular fluid, cerebrospinal fluid, synovial fluid, pleural fluid, serum, lymph, saliva, urine, and tissues. The sample is preferably a preparation in which a tissue or cells collected from a living body is fixed, or a sample obtained from the test sample, such as a cell culture medium. These samples are encompassed by the test sample of the present invention.

When a sample obtained from the test sample is used, such as a preparation in which a tissue or cells collected from a living body is fixed, or a cell culture medium, in situ hybridization is preferably used. The in situ hybridization has been evolved as an approach for confirming the presence or absence or distribution of particular DNA or RNA in cells or tissues, and the strength of its expression. This method employs the principles on which a probe nucleic acid having a nucleotide sequence complementary to an intracellular particular nucleic acid sequence has the property of specifically forming a complex. The probe is labeled in advance with a radioisotope (RI), an antigenic substance ((hapten), or the like. As a result, the hybridization site can be distinguished through the detection of the label. Thus, the in situ hybridization is used in, for example, the detection of intracellular DNA or RNA, or the like. Labeling with RI can be used preferably as the probe labeling. Furthermore, for example, fluorescence labeling with a nonradioactive substance such as biotin or hapten (e.g., digoxigenin) can be used more preferably. For example, a detection method by fluorescence in situ hybridization called FISH is particularly preferably used.

The cancer diagnosed by the present invention is not particularly limited. Specific examples thereof can include lung cancer, uterine cervix cancer, and esophagus cancer. In the present invention, any of primary foci and metastatic foci of these cancers can be diagnosed.

In the present invention, an arbitrary animal species expressing the TMPRSS11E gene can be used as the test subject. The test subject is particularly preferably a human. When a non-human animal species is used as the test subject, a TMPRSS11E gene derived from this animal species is detected.

Hereinafter, a specific aspect of the detection method will be described. First, a sample is prepared from a test subject. Subsequently, TMPRSS11E mRNA contained in the sample is detected. In the present invention, cDNA synthesized from the mRNA can also be detected. In the present invention, when TMPRSS11E mRNA or TMPRSS11E-encoding cDNA is detected in the test sample, the test subject is diagnosed as possibly having cancer. For example, when the amount of the TMPRSS11E mRNA or TMPRSS11E-encoding cDNA detected in the test sample is larger than that in negative controls or healthy individuals, the test subject is shown to have cancer or highly possible have cancer in the future.

A method for detecting the mRNA is known in the art. Specific examples of the method that can be used in the present invention include: nucleic acid hybridization using samples immobilized on a solid phase selected from gene chips, cDNA arrays, and membrane filters; RT-PCR; real-time PCR; subtraction method; differential display method; differential hybridization; and cross hybridization.

The detection method of the present invention can be automated using various automatic detectors. Such automation achieves detection of a large number of samples in a short time.

6.3 Kit for Cancer Diagnosis

The present invention also provides a diagnostic drug or a kit for cancer diagnosis, comprising a reagent for detecting a TMPRSS11E protein in a test sample. The diagnostic drug of the present invention comprises at least the anti-TMPRSS11E antibody.

The reagent for cancer diagnosis of the present invention can be combined with other factors used in TMPRSS11E detection to prepare a kit for cancer diagnosis. Specifically, the present invention relates to a kit for cancer diagnosis, which comprises: an antibody binding to TMPRSS11E; and a reagent for detecting the binding of the antibody to TMPRSS11E and may further comprise a control sample comprising a biological sample containing TMPRSS11E. A manual for instruction of assay procedures may further be included in the kit of the present invention.

Hereinafter, the present invention will be described specifically with reference to Examples. However, the present invention is not intended to be limited to these Examples.

EXAMPLES

Example 1

TMPRSS11E mRNA Expression Analysis Using real-time PCR

Lung cancer cell lines h2009, h2087, h2122, and h209 were purchased from ATCC. After culture under conditions described in the attached documents, cells corresponding to $1 \times 10^7$ were collected, and total RNA was prepared therefrom using Trizol (Invitrogen Corp.). 1 µg of the total RNA was treated with DNase I (Invitrogen Corp.). Then, cDNA was synthesized therefrom using SuperScript III First Strand Synthesis System for RT-PCR (Invitrogen Corp.) and oligo (dT) primers. cDNA was also synthesized in the same way as above from the total RNAs of various normal tissues shown in Table 1.

Tissues used in TMPRSS11E gene expression analysis

| Name | Company name | Catlog No. |
| --- | --- | --- |
| Brain, cerebrum | Ambion | 6000 |
| Ovary | Ambion | 6000 |
| Pancreas | Ambion | 7954 |
| Thyroid gland | Ambion | 6000 |
| Testis | Ambion | 7972 |
| Breast | Stratagene | 540045 |
| Spleen | Ambion | 6000 |
| Tonsil | Clontech | 636587 |
| Thymus gland | Ambion | 6000 |
| Bone marrow | Clontech | 636548 |
| Lung | Ambion | 7968 |
| Heart | Stratagene | 540011 |
| Esophagus | Ambion | 6000 |
| Stomach | Stratagene | 540037 |
| Small intestine | Ambion | 6000 |
| Colon | Clontech | 636553 |
| Liver | Ambion | 6000 |
| Salivary gland | Clontech | 636552 |
| Kidney | Ambion | 7976 |
| Prostate | Ambion | 6000 |
| Uterus | Stratagene | 540043 |
| Uterine cervix | Ambion | 6000 |
| Skeleton mascle | Ambion | 6000 |
| Skin | Stratagene | 540031 |
| Posterior root | Clontech | 636150 |
| Pericardium | Ambion | 6852 |
| Placenta | Ambion | 6000 |
| Peripheral blood | Clontech | 636580 |
| Lymph node | Stratagene | 540021 |
| Caval vein | Stratagene | 540121 |
| Medulla oblongata | Clontech | 636562 |
| Adipose | Ambion | 6000 |
| Bladder | Ambion | 6000 |
| Trachea | Ambion | 6000 |

These cDNAs were used to carry out real-time PCR by an intercalator method using SYBR Green I. Specifically, 20 µl of a reaction solution containing SYBR (registered trademark) Premix Ex Taq (Takara Bio Inc.), a sense primer (SEQ ID NO: 31), and an antisense primer (SEQ ID NO: 32) was subjected to 33 cycles each involving 95° C. for 5 seconds and 60° C. for 30 seconds with each cDNA derived from the total RNA corresponding to 3.3 ng as a template. A calibration curve was prepared based on samples obtained with PCR products purified beforehand as a template, and the cDNA levels of samples were calculated from the quantified values. As shown in FIG. 1, TMPRSS11E mRNA exhibited a high value in the lung cancer strains h2009, h2087, h2122, and h209 and was localized to the tonsil, the esophagus, and the uterine cervix among the normal tissues.

Example 2

Preparation of Anti-TMPRSS11E Antibody

TMPRSS11E (Accession No. NM 014058) is a type II membrane protein composed of 423 amino acids. Its nucleotide sequence is shown in SEQ ID NO: 1, and the amino acid sequence is shown in SEQ ID NO: 2. This protein has trypsin-like serine protease and SEA domains in the extracellular region. Since it was found this time that TMPRSS11E is highly expressed in certain kinds of cancers, the present inventors launched the preparation of an anti-TMPRSS11E antibody.

1. Establishment of Human TMPRSS11E-Expressing Cell Line

First, the full-length gene of TMPRSS11E was cloned. Specifically, a sense primer comprising an EcoRI recognition sequence and a kozak sequence added to the 5' end and an antisense primer comprising a tag sequence and a NotI sequence added to the 3' end were designed, and a reaction solution containing 10xKOD-Plus buffer, 2 mM dNTPs, 25 mM MgSO4, and KOD-Plus (manufactured by Takara Bio Inc.) was subjected to 35 cycles each involving 94° C. for 30 seconds, 50° C. for 10 seconds, and 72° C. for 1.5 minutes with H2009 cDNA as a template. The amplification product obtained by the PCR reaction was inserted into pGEM-T easy using pGEM-T Easy Vector System I (Promega Corp.). The sequence was confirmed using ABI3730 DNA Analyzer. This inserted product was cleaved with EcoRI and NotI and then cloned into pMCN vectors. The pMCN vectors are capable of inducing expression under the control of a mouse CMV promoter (Accession No. U68299) and contain a neomycin resistance gene incorporated therein. This expression plasmid DNA was introduced into DG44 cells and Ba/F3 cells by electroporation. Stably expressing strains were established by screening using 500 µg/mL Geneticin. The DG44 cells were purchased from Invitrogen Corp., and the Ba/F3 cells were purchased from RIKEN Japan.

2. Preparation of Soluble Human sTMPRSS11Ep1/Mouse IgG2a Fc Fusion Protein

Fusion proteins of a sTMPESS11Ep1 region (Ser 159-Ile 423) and mouse IgG2a Fc was prepared which contained a serine protease domain as an immunogen. PCR reaction was performed using a sense primer comprising an EcoRI recognition sequence, a kozak sequence, and a mouse IL3 signal sequence added to the 5' end and an antisense primer comprising a CpoI recognition sequence added thereto. The PCR amplification product was cloned into pGEM-T Easy and its nucleotide sequence was confirmed. Then, a fragment obtained by digestion with EcoRI and CpoI was cloned into pMCDN_mIgG2aFc. The pMCDN_mIgG2aFc is derived from a pMCN vector in which the Fc sequence of mouse heavy chain IgG2a from the hinge onward is inserted at EcoRI and NotI recognition sites, and sTMPRSS11Ep1 and mIgG2a Fc sequences are linked via the CpoI recognition sequence. The sequence represented by SEQ ID NO: 33 represents the nucleotide sequence of sTMPRSS11Ep1_mIgG2aFc, and the sequence represented by SEQ ID NO: 34 represents the amino acid sequence of sTMPRSS11Ep1mIgG2aFc.

pMCDN_sTMPRSS11Ep1_mIgG2aFc was introduced into DG44 cells (Invitrogen Corp.) by electroporation. Stably expressing cells were established by screening using 500 µg/mL Geneticin. The stably expressing cells were cultured at large scale, and sTMPRSS11Ep1_mIgG2aFc proteins were purified from the culture supernatant. The culture supernatant was charged into Hi Trap rProtein A (manufactured by GE Healthcare) column, which was then washed with a binding buffer (20 mM sodium phosphate (pH 7.0)), followed by elution with an elution buffer (0.1 M glycine-HCl (pH 2.7)). The elution was performed in a tube supplemented with a neutralization buffer (1 M Tris-HCl (pH 9.0)), with which the eluate was immediately neutralized. Next, the eluate was gel-filtered using Superdex 200 HR 26/60 (GE Healthcare), followed by substitution by PBS. The purified proteins were quantified using DC protein assay (Bio-Rad Laboratories, Inc.) and calculated with bovine IgG included therein as a standard.

3. Preparation of Anti-TMPRSS11E Antibody

Balb/c mice or MRL/MpJUmmCrj-lpr/lpr mice (hereinafter, referred to as MRL/lpr mice; purchased from Charles River Laboratories Japan, Inc.) were used as immunized animals. Immunization was started when the mice were 6 week old. In initial immunization, sTMPRSS11Ep1_mIgG2aFc was adjusted to 50 µg/mouse and emulsified using a Freund's complete adjuvant (FCA, Becton, Dickinson and Company), and this emulsion was subcutaneously administered to each mouse. Two weeks later, the immunogen was adjusted to 25 µg/mouse and emulsified using a Freund's incomplete adjuvant (FIA, Becton, Dickinson and Company), and this emulsion was subcutaneously administered thereto. Subsequently, 2 or 3 boosters were performed at 1-week intervals. Four days after the final immunization, spleen cells were excised therefrom and mixed with mouse myeloma cells P3-X63Ag8U1 (P3U1, purchased from ATCC) at a 2:1 ratio. Cell fusion was performed by gradually adding PEG1500 (Roche Diagnostics GmbH). PEG1500 was diluted by the careful addition of an RPMI1640 medium (GIBCO BRL) and removed by centrifugation. Then, the residue was suspended in RPMI1640 containing 10% FBS, and the suspension was inoculated at a concentration of 100 µL/well to a 96-well culture plate. On the next day, RPMI1640 containing 10% FBS, 1×HAT media supplement (Sigma-Aldrich Corp.), and 0.5×BM-Condimed H1 Hybridoma cloning supplement (Roche Diagnostic GmbH) (hereinafter, referred to as a HAT medium) was added thereto at a concentration of 100 µL/well. Two or three days later, half the culture medium was replaced by a HAT medium. Seven days later, screening was performed using the culture supernatant. The screening was performed by flow cytometry using the TMPRSS11E-expressing DG44 cells established above. Positive clones were confirmed not to bind to the parental strain DG44 cells and then prepared as single clones by a limiting dilution method. As a result of isotyping using Roche Diagnostic GmbH Isostrip, the established hybridomas TM094 and TM191 were both IgG1 kappa.

The antibody was purified using Hi Trap Protein G HP in the same way as above from a culture supernatant of the hybridomas cultured in a HAT medium with FBS (Ultra-low IgG) (GIBCO BRL) as serum. The elution fraction was stored at 4° C. after substitution by PBS using PD-10 column (Amersham Biosciences Corp.). The purified antibody was quantified using DC protein assay (BIO-RAD Laboratories, Inc.) and calculated with bovine IgG included therein as a standard.

Example 3

Sequencing of Anti-TMPRSS11E Antibody Variable Region Gene

The antibody variable region genes were sequenced for TM094 and TM191. Total RNA was extracted from 1×10$^7$ cells of each hybridoma using RNeasy Plant Mini Kits (QIAGEN). 1 µg of the total RNA was used to amplify 5'-terminal gene fragments using SMART RACE cDNA Amplification Kit (CLONTECH Laboratories, Inc.), a synthetic oligonucleotide MHC-IgG1 (SEQ ID NO: 35) complementary to the sequence of a mouse IgG1 constant region or a synthetic oligonucleotide kappa (SEQ ID NO: 36) complementary to the nucleotide sequence of a mouse κ chain constant region. Reverse transcription reaction was performed at 42° C. for 1.5 hours. 50 µL of a PCR solution contained 5 µL of 10×Advantage 2 PCR Buffer, 5 µL of 10×Universal Primer A Mix, 0.2 mM dNTPs (dATP, dGTP, dCTP, and dTTP), 1 µL of Advantage 2 Polymerase Mix (all manufactured by CLONTECH Laboratories, Inc.), 2.5 µL of the reverse transcription reaction product, and 10 pmoles of the synthetic oligonucleotide MHC-IgG1 or kappa and was subjected to an initial temperature of 94° C. for 30 seconds, then 5 repetitive cycles each involving 94° C. for 5 seconds and 72° C. for 3 minutes, 5 repetitive cycles each involving 94° C. for 5 seconds, 70° C. for 10 seconds, and 72° C. for 3 minutes, and 25 repetitive cycles each involving 94° C. for 5 seconds, 68° C. for 10 seconds, and 72° C. for 3 minutes. Finally, the reaction product was heated at 72° C. for 7 minutes. Each PCR product was purified from the agarose gel using QIAquick Gel Extraction Kit (manufactured by QIAGEN), then cloned into pGEM-T Easy vectors, and sequenced. The nucleotide sequence of the TM094 heavy chain variable region is shown in SEQ ID NO: 37, and its amino acid sequence is shown in SEQ ID NO: 38. The nucleotide sequence of the TM094 light chain variable region is shown in SEQ ID NO: 39, and its amino acid sequence is shown in SEQ ID NO: 40. The nucleotide sequence of the TM191 heavy chain variable region is shown in SEQ ID NO: 41, and its amino acid sequence is shown in SEQ ID NO: 42. The nucleotide sequence of the TM191 light chain variable region is shown in SEQ ID NO: 43, and its amino acid sequence is shown in SEQ ID NO: 44.

Example 4

Preparation of Anti-TMPRSS11E Mouse-Human Chimeric Antibody

The sequences of the heavy and light chain variable regions of each antibody were linked to the sequences of the human heavy and light chain constant regions. The heavy chain sequences were amplified by PCR using a synthetic oligonucleotide that was complementary to the 5'-terminal nucleotide sequence of the variable region and had a Kozak sequence and an EcoRI site, and a synthetic oligonucleotide that was complementary to the 3'-terminal nucleotide sequence and had an NheI site. The light chain sequences were amplified by PCR using a synthetic oligonucleotide that was complementary to the 5'-terminal nucleotide sequence of the variable region and had a Kozak sequence and a BamHI site, and a synthetic oligonucleotide that was complementary to the 3'-terminal nucleotide sequence and had a BsiWI site. The obtained PCR products were cloned into antigen expression plasmids pMCDN_G1k. The pMCDN_G1k is derived from a pMCDN vector in which a human IgG1 constant region is cloned, and has a structure in which a mouse heavy chain variable region and a human heavy chain (γ1 chain) constant region are linked via an NheI site. Moreover, this vector has inserts of another expression unit containing a mouse CMV promoter and a human κ chain constant region and has a structure in which a mouse light chain variable region and a human light chain (κ chain) constant region is linked via a BsiWI site. This plasmid induces the expression of the neomycin resistance gene, the DHFR gene, and the anti-TMPRSS11E mouse-human chimeric antibody gene in animal cells. The nucleotide sequence of the chimeric TM094 heavy chain is shown in SEQ ID NO: 45, and its amino acid sequence is shown in SEQ ID NO: 46. The nucleotide sequence of the chimeric TM094 light chain is shown in SEQ ID NO: 47, and its amino acid sequence is shown in SEQ ID NO: 48. The nucleotide sequence of the chimeric TM191 heavy chain is shown in SEQ ID NO: 49, and its amino acid sequence is shown in SEQ ID NO: 50. The nucleotide sequence of the chimeric TM191 light chain is shown in SEQ ID NO: 51, and its amino acid sequence is shown in SEQ ID NO: 52.

pMCDN_G1k_TM094 and pMCDN_G1k_TM191 were introduced into DG44 cells by electroporation. Anti-TMPRSS11E chimeric antibody-constantly expressing CHO cells were established by screening using 500 µg/mL Geneticin. Next, antibodies were purified from the culture supernatant using Hi Trap rProtein A column. After buffer substitution by using PD-10 column, the purified antibodies (chi.TM094 (DG) and chi.TM191 (DG)) were quantified by DC Protein Assay and stored at 4° C.

Example 5

Preparation of Low-fucose Anti-TMPRSS11E Mouse-human Chimeric Antibody

A method which involves modifying the sugar chain of an antibody is known as a method for enhancing the ADCC activity of the antibody. For example, WO 99/54342 discloses that ADCC activity is improved by modifying antibodies by glycosylation. Moreover, WO 00/61739 discloses that ADCC activity is adjusted depending on the presence or absence of fucose in the sugar chains of antibodies. WO 02/31140 discloses that antibodies having a sugar chain free from α-1,6 core-fucose are prepared by allowing YB2/0 cells to produce the antibodies. WO2005/017155 discloses Examples relating to fucose transporter gene-knockout CHO cells (CHO_FTKO). Likewise, antibodies having a sugar chain free from α-1,6 core-fucose can be produced.

The anti-TMPRSS11E mouse-human chimeric antibody expression plasmids constructed above were incorporated into CHO_FTKO cells by electroporation. Anti-TMPRSS11E chimeric antibody-constantly expressing CHO_FTKO cells were established by screening using 500 μg/mL Geneticin. Next, antibodies were purified from the culture supernatant using Hi Trap rProtein A column. After buffer substitution by PBS using PD-10 column, the purified antibodies (chi.TM094 (FTKO) and chi.TM191 (FTKO)) were quantified by DC Protein Assay and stored at 4° C.

Example 6

Evaluation on Avidity of Anti-TMPRSS11E Antibody by Flow Cytometry

Figure 2:
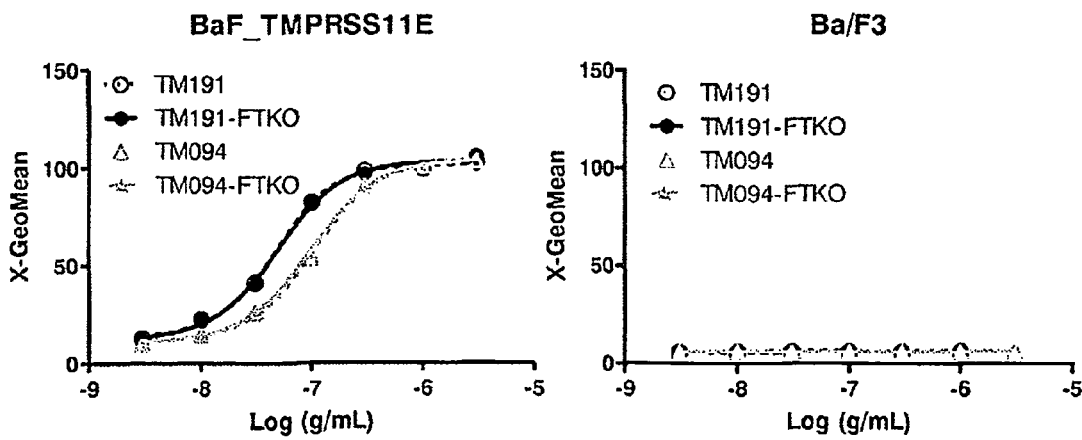
FIG. 2 shows the avidity of a chimeric anti-TMPRSS11E antibody by flow cytometry.
Figure 3:
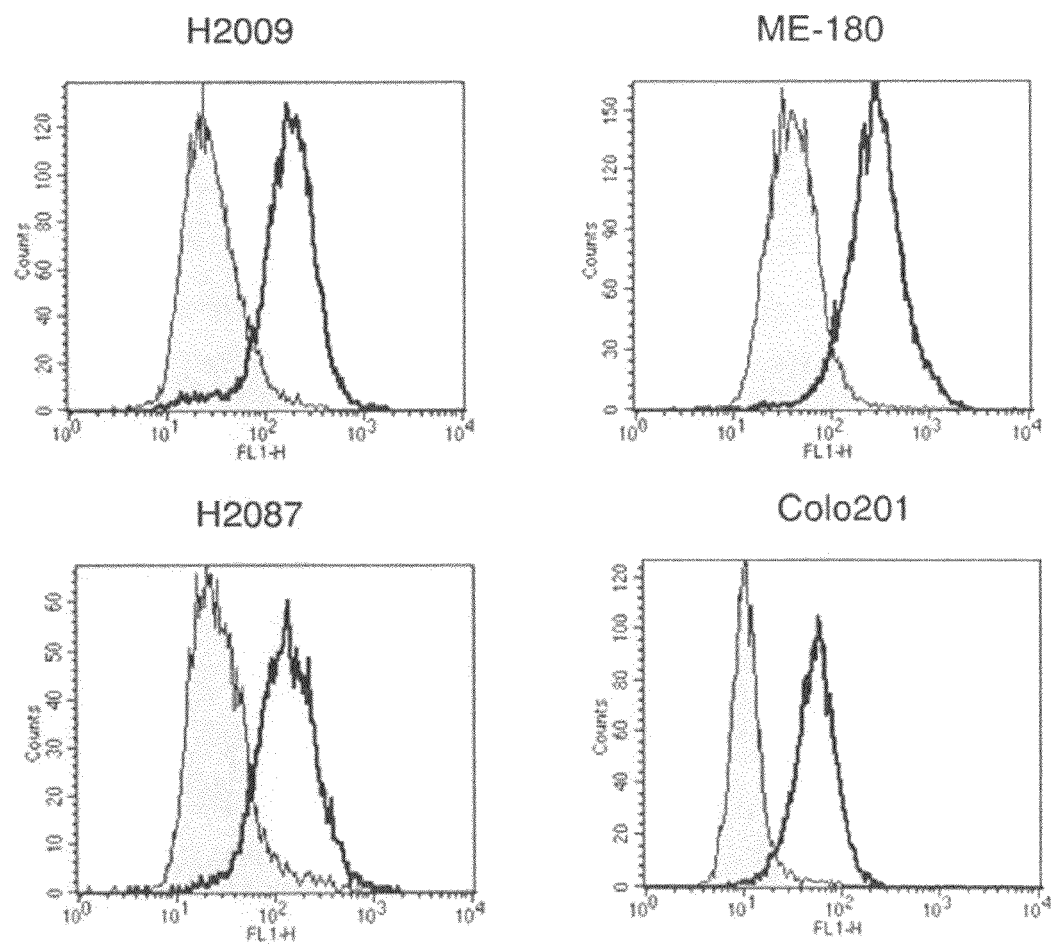
FIG. 3 shows the avidity of an anti-TMPRSS11E antibody to cancer cell lines by flow cytometry.

The TMPRSS11E-constantly expressing cells thus constructed were evaluated for binding to the parental strain thereof by flow cytometry. The anti-TMPRSS11E antibody diluted to an appropriate concentration was added to cells corresponding to $5\times10^5$ and reacted for 1 hour on ice. The cells were washed by centrifugation. Then, FITC-labeled anti-human IgG antibodies were added thereto and reacted for 1 hour on ice. The cells were washed by centrifugation and then suspended in a medium containing 2 μg/mL propidium iodide, and the suspension was applied to FACS Calibur (Becton, Dickinson and Company). As shown in FIG. 2, all the antibodies did not bind to the parental strain Ba/F3 and exhibited strong avidity in a concentration-dependent manner to the strains forced to express TMPRSS11E. This demonstrated that these antibodies specifically bind to TMPRSS11E. The chimeric antibodies and low-fucose chimeric antibodies had equivalent avidity. Next, avidity to various cancer cell lines was evaluated by flow cytometry. As shown in FIG. 3, the antibodies exhibited avidity to lung cancer strains h2009 and h2087, an uterine cancer strain ME-180 (purchased from ATCC), and a colon cancer strain colo201 (purchased from Japanese Collection of Research Bioresources). It was demonstrated that in these cancer cell lines, TMPRSS11E is highly expressed not only at the RNA level but also at the protein level. As a result of roughly calculating the number of antigens expressed per cell using DAKO QIFIKIT, approximately 26,000 molecules for H2009 and approximately 40,000 molecules for ME-180 were expressed, demonstrating sufficient expression as target antigens for antibody drugs.

Example 7

Assay of Antibody-dependent Cell-mediated Cytotoxicity (ADCC) Activity of Anti-TMPRSS11E Antibody 1. Establishment of full-length human CD16-constantly expressing cell Full-length human CD16 (RefSeq ID, NM_000569) was cloned into vectors (pMCDN) for expression in mammalian cells (the resulting vectors were designated as pMCDN/CD16). The pMCDN/CD16 was introduced into NK-92 cells (purchased from ATCC, CRL-2407) by electroporation. An NK-92 cell line (CD16-NK92) constantly expressing full-length human CD16 was established by screening using 500 μg/ml Geneticin. The CD16-NK92 cells were cultured using Alpha minimum essential medium without ribonucleosides and deoxyribonucleosides with L-glutamine medium (Invitrogen Corp.) containing 500 μg/ml Geneticin, penicillin/streptomycin (Invitrogen Corp.), 0.2 mM inositol (Sigma-Aldrich Corp.), 0.1 mM 2-mercaptoethanol (Invitrogen Corp.), 0.02 mM folic acid (Sigma-Aldrich Corp.), 100 U/ml recombinant human interleukin-2 (PeproTech, Inc.), 10% horse serum (Invitrogen Corp.), and 10% fetal bovine serum (Invitrogen Corp.).

2. Assay of ADCC Activity of Anti-TMPRSS11E Antibody

H2009 or colo201 cells were added at 50 μl/well to a 96-well flat-bottomed plate and cultured at 37° C. for 2 days in a 5% $CO_2$ incubator. A solution containing 240 μCi/ml Chromium-51 (Code No. CJS4, GE Healthcare Bio-Sciences Corp.) added to an RPMI1640 medium containing 10% fetal bovine serum and penicillin/streptomycin (hereinafter, referred to as medium) was added thereto at a concentration of 10 μl/well, and the cells were cultured for another 1 hour. Each well was washed with 300 μl of the medium, and 100 μl of the medium was then added thereto. Next, 50 μl of the anti-TMPRSS11E antibody or a control human IgG1 antibody (Cat. No. PHP010, AbD Serotec) was added thereto. Subsequently, 50 μl of CD16-NK92 cells suspended at a concentration of $1\times10^6$ cells/ml in the medium was added thereto. The plate was cultured at 37° C. for 4 hours in a 5% $CO_2$ incubator. Then, the radioactivity of 100 μl of the supernatant was measured using a gamma counter (1480 WIZARD 3", Wallac Corp.). The specific chromium release rate (%) was determined according to the following equation:

$$\text{Specific chromium release rate}(\%)=(A-C)\times100/(B-C).$$

In this equation, A represents radioactivity (cpm) from each well; B represents the mean of radioactivities (cpm) from wells supplemented with 100 μl of 2% Nonidet P-40 solution (Code No. 252-23, Nacalai Tesque); and C represents the mean of radioactivities (cpm) from wells supplemented with 100 μl of a medium. The tests were conducted in duplicate, and the mean of specific chromium release rates and standard deviation were calculated.

ME-180 cells were labeled with 20 μg/mL Calcein-AM (DOJINDO Corp.), and the antibody and effector cells were allowed to act thereon in the same way as above. The fluorescence intensity of 100 μl of the supernatant was measured using ARVO (WALLAC Corp.), and the specific Calcein-AM release rate (%) was calculated.

As shown in FIG. 4, the ADCC activity of the anti-TMPRSS11E antibody was confirmed against each cancer cell line. Moreover, it was confirmed the reduction in fucose enhances ADCC activity.

Example 8

Antitumor Effect of Anti-TMPRSS11E Antibody Using Hum-ZAP

Next, whether an immunotoxin targeting TMPRSS11E could exhibit antitumor effect was evaluated using Hum-ZAP. The Hum-ZAP comprises a protein synthesis-inhibiting toxin, saporin, conjugated to an anti-human IgG antibody and was obtained from Advanced Targeting Systems. On the previous day, h2009 or ME-180 cells were seeded at 500 cells/50 μL/well over a 96-well plate. A mixture of 100 ng of Hum-ZAP and 100 ng of the anti-TMPRSS11E chimeric antibody (TM094 and TM191) was added thereto. After 96-hour culture, 10 μL of Cell Count Reagent SF (Nacalai Tesque Corp.) was added thereto. Two hours later, absorbance at 450 nm was measured. As shown in FIG. 5, the inhibition of growth was not observed in Hum-ZAP alone, whereas antitumor effect was confirmed in a manner dependent on the anti-TMPRSS11E antibody.

Example 9

Neutralization Activity of Anti-TMPRSS11E Antibody Against Protease Activity

Figure 6:
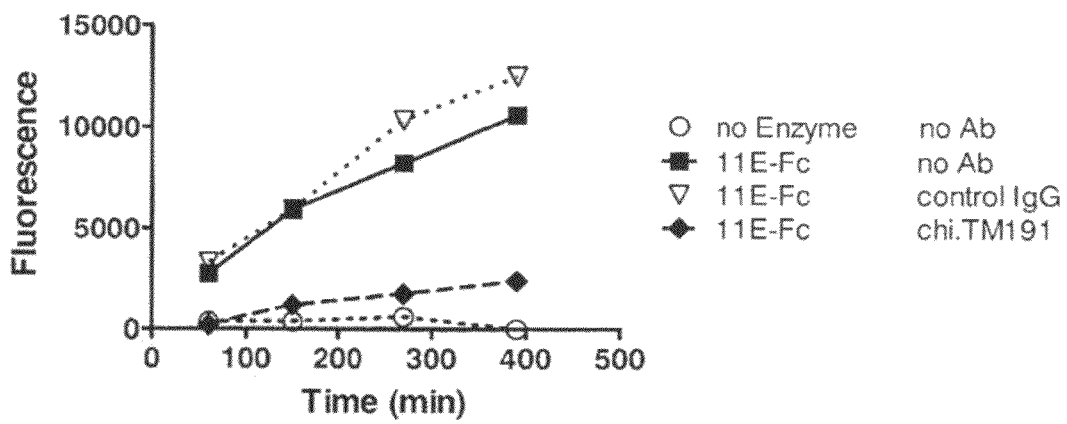
FIG. 6 shows the protease-neutralizing activity of an anti-TMPRSS11E antibody.

TMPRSS11E belongs to the type II serine protease family and has a protease domain. An antibody binding to TMPRSS11E is likely to neutralize this function. Enzchek Gelatinase/Collagenase Assay Kit (Molecular Probes Corp.) was used to construct a protease activity evaluation system. 1 μg of TM191 was added to 600 ng of the soluble human sTMPRSS11Ep1/mouse IgG2a Fc fusion protein (11E-Fc) constructed above, and the mixture was left at 4° C. for 1 hour. DQ-Gelatin labeled with a fluorescent material was added thereto according to the manual included in the kit and reacted at room temperature, and the fluorescence intensity was measured over time. As shown in FIG. 6, rise in fluorescence intensity was not confirmed in the absence of 11E-Fc and was confirmed in a manner dependent on the addition of 11E-Fc. No change was observed in a sample obtained by adding control IgG to 11E-Fc, whereas rice in fluorescence intensity was not confirmed in the sample mixed with TM191. This demonstrated that TM191 has the activity of neutralizing the protease activity of TMPRSS11E.

Example 10

Immunoblot Analysis Using Anti-TMPRSS11E Antibody

A fusion protein of a TMPRSS11E SEA domain (Tyr 42-Arg 191) and a mouse IgG2a Fc region was prepared according to the method described above. This fusion protein was used to immunize Balb/c mice or MRL/lpr mice. Hybridomas were established in the same way as above. New England Biolabs Inc. pMALc2x vectors were used in screening, which was performed by ELISA using fusion proteins of MBP and SEA domains that were expressed in E. coli, then purified, and immobilized on a solid phase. RNA was extracted from hybridomas producing EA230 that exhibited strong avidity, and the antibody variable region gene was sequenced according to the method described above. The nucleotide sequence of the EA230 heavy chain variable region is shown in SEQ ID NO: 53, and its amino acid sequence is shown in SEQ ID NO: 54. The nucleotide sequence of the EA230 light chain variable region is shown in SEQ ID NO: 55, and its amino acid sequence is shown in SEQ ID NO: 56.

Figure 7:
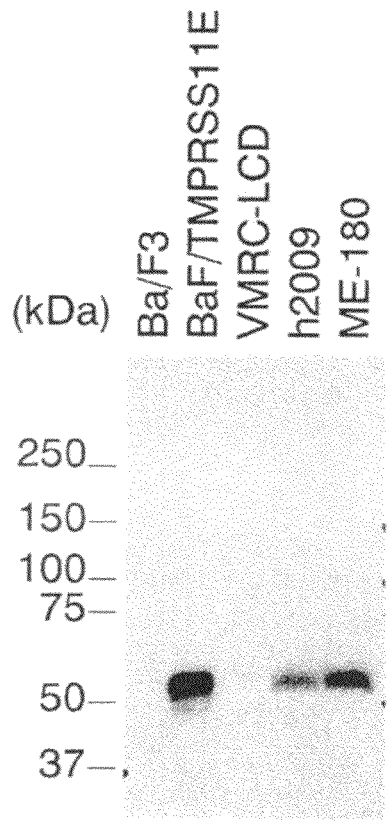
FIG. 7 shows immunoblot analysis using an anti-TMPRSS11E antibody.

Cell lysates of Ba/F3, TMPRSS11E-expressing Ba/F3 (BaF/TMPRSS11E), a TMPRSS11E-negative cancer cell line VMRC-LCD, and TMPRSS11E-positive cancer cell lines h2009 and ME-180 were prepared. 50 μL of NP-40 Lysis Buffer (0.5% (v/v) Nonidet P40, 20 mM Tris-HCl (pH 7.5), 150 mM NaCl, 5 mM EDTA) was added to $1 \times 10^6$ cells and left at 4° C. for 15 minutes. Then, after centrifugation (14,000 rpm, 15 min), the supernatant was used as lysates. The lysates corresponding to $2 \times 10^5$ cells were separated by SDS-PAGE and then transferred to Immobilon-P (Millipore Corp.) using Trans-Blot SD Semi-Dry Electrophoretic Transfer Cell (Bio-Rad Laboratories, Inc.). The membrane was gently washed with TBS-T (0.05% Tween 20, TBS) and then shaken for 1 hour in TBS-T containing 5% skim milk. After shaking for approximately 10 minutes in TBS-T, 0.5 μg/mL EA230 antibodies diluted with TBS-T containing 1% skim milk were added to the membrane, which was then shaken for 1 hour. The membrane was washed with TBS-T (10 min×3 times), then shaken for 1 hour together with HRP-anti-mouse IgG antibodies (GE Healthcare Corp.) diluted 1/2000 with TBS-T containing 1% skim milk, and then washed with TBS-T (10 min×3 times). Color development was performed using ECL-Plus (GE Healthcare Corp.), and the membrane was developed using Hyperfilm ECL (GE Healthcare Corp.). As shown in FIG. 7, EA230 did not react with the parental strain Ba/F3, whereas a band was detected at a position of more than 50 kDa for the strains forced to express TMPRSS11E. Since the presumed molecular weight of TMPRSS11E is 47.7 kDa, it seemed that TMPRSS11E that underwent sugar chain modification was probably detected. This means that TMPRSS11E can be detected specifically by immunoblot using EA230. A similar band was also detected in the cancer cell lines, demonstrating that TMPRSS11E is certainly highly expressed in the cancer cell lines.

Example 11

Immunohistochemical (IHC) Analysis Using Anti-TMPRSS11E Antibody

IHC analysis was conducted using EA230 for the purpose of evaluating the expression of TMPRSS11E in clinical cancer tissues. Test slide, Lung cancer tissues with corresponding normal tissues (ISU ABXIS, A71611) was used as a lung cancer tissue array. Multiple (uterine cervix) cervical squamous cancer tissue array (US Biomax, Inc., CR803) was used as a uterine cervix cancer tissue array. Human Common Cancers Array (SuperBioChips Laboratories, MA1) was used as an esophagus cancer tissue array. DAKO Envision Kit was used in staining. The tissues were deparaffinized, then activated with 10 mM citrate buffer (pH 6.0) in an autoclave (120° C., 10 min), and stained using 10 μg/mL EA230 according to the manual included therein. As shown in FIG. 8, strong staining was confirmed in lung cancer, uterine cervix cancer, and esophagus cancer tissues. This demonstrated that TMPRSS11E is also highly expressed in the clinical cancer tissues (Lang and Schuller, 2001). The staining was localized to cell membranes. Thus, TMPRSS11E was regarded as being promising as a target antigen for antibody drugs.

Example 12

In vivo Antitumor Effect of Anti-TMPRSS11E Antibody

1. Preparation of Mouse IgG2ak-Type TM191

Sequences encoding TM191 H and L chain variable regions were cleaved from the human-mouse chimeric TM191 expression plasmids prepared in Example 4 and cloned into pMCDN mG2ak vectors. The pMCDN mG2ak vectors are derived from a pMCDN vector in which a mouse IgG2a constant region is cloned, and has a structure in which mouse H chain variable and constant regions are linked via an NheI site. Moreover, the vectors have inserts of another expression unit containing a mouse CMV promoter and a mouse κ chain constant region, and have a structure in which mouse L chain variable and constant regions are linked via a BsiWI site. This plasmid induces the expression of the neomycin resistance gene, the DHFR gene, and the mouse IgG2a-type TM191 antibody gene in animal cells. The nucleotide sequence of the mouse IgG2a-type TM191 H chain is shown in SEQ ID NO: 57, and its amino acid sequence is shown in SEQ ID NO: 58. The nucleotide sequence of the mouse kappa-type TM191 L chain is shown in SEQ ID NO: 59, and its amino acid sequence is shown in SEQ ID NO: 60. pMCDN mG2ak TM191 was introduced into DG44 cells and CHO FTKO by electroporation. Constantly expressing CHO cells were established by screening using 500 μg/mL Geneticin. Next, antibodies were purified from the culture supernatant using Hi Trap rProtein A column. After buffer substitution by PBS, the purified antibodies (TM191 mIgG2ak (DG) and TM191 mIgG2ak (FTKO)) were quantified by DC Protein Assay and stored at 4° C.

2. Establishment of TMPRSS11E-expressing Liver Cancer Cell Line

Liver cancer cell line SK-Hep-1 cells were purchased from ATCC. The cells were cultured in D-MEM (Sigma-Aldrich Corp.), 10% FBS (BOVAGEN), and 1% penicillin-streptomycin (GIBCO). The full-length TMPRSS11E gene cloned in Example 2 was cloned into pCOSII-Zeo vectors. The pCOSII-Zeo vectors contain a Zeocin resistance gene incorporated therein. The prepared TPMRSS11E expression plasmids were introduced into SK-Hep-1 cells by electroporation and screened using 800 μg/mL Zeocin. A TMPRSS11E-expressing strain was established by a limiting dilution method. As shown in FIG. 9, TM191 did not bind to the parental strain SK-Hep1 in flow cytometry and exhibited strong binding to the strain forced to express TMPRSS11E.

3. In vivo Antitumor Effect on TMPRSS11E-expressing Cell
3.1. Preparation of Human Liver Cancer-transplanted Mouse Model On the previous day, 0.2 mg of anti-asialo GM1 antibodies (Wako Pure Chemical Industries, Ltd.) was intraperitoneally administered to 56 C.B-17/Icr-scid mice (female, 6-week-old (at the time of tumor transplantation), CLEA Japan) in advance. The TMPRSS11E-expressing liver cancer cell line obtained in the paragraph 1.2 was subcutaneously transplanted thereto at a concentration of 5E6 cells/mouse (a cell suspension of a 1:1 mixture of medium (D-MEM (Sigma-Aldrich Corp.), 10% FBS (BOVAGEN), 1% penicillin-streptomycin (GIBCO), 400 μg/mL Geneticin (GIBCO), 800 μg/mL Zeocin (Invitrogen Corp.)) and matrigel).

14 days after transplantation, the tumor size (major axis× minor axis×minor axis (mm3)) (using calipers) and the body weight were measured. The mice were divided into a total of 6 groups each containing 6 mice, and administration was started.

3.2. Antibody Administration and Measurement

On the day of administration, the antibodies TM191 mIgG2ak (DG) and TM191 mIgG2ak (FTKO) prepared in the paragraph 1. were adjusted to 0.5 mg/mL (5 mg/kg administration group) or 2.5 mg/mL (25 mg/kg administration group) using PBS (−) (Sigma-Aldrich Corp.) and administered at a concentration of 10 mL/kg to the tail veins of the mice divided into groups in the paragraph 3.1. The administration was performed a total of four times (once a week). During this administration period and up to 1 week after the final administration, the tumor size and the body weight were measured twice a week.

3.3. Results

Figure 10:
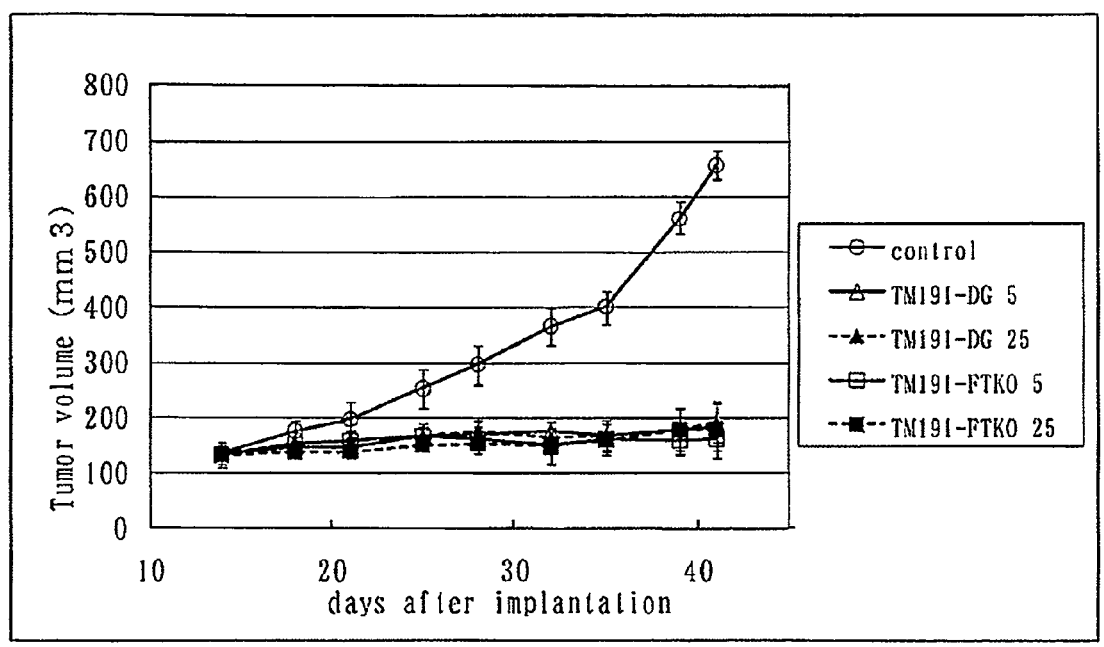
FIG. 10 shows the antitumor effect of an anti-TMPRSS11E antibody.

The administration of TM191 mIgG2ak (DG) and TM191 mIgG2ak (FTKO) significantly inhibited the growth of the subcutaneously transplanted human liver cancer in both the 5 mg/kg and 25 mg/kg administration groups (FIG. 10).

All publications, patents, and patent applications cited herein are incorporated herein by reference with their entirety.

Industrial Applicability

An antibody of the present invention can be used as an anticancer agent and as a diagnostic drug for cancer.

The invention claimed is:

1. An antibody binding to a TMPRSS11E protein, the antibody being selected from the following:

(1) an antibody comprising a heavy chain variable region comprising heavy chain CDR1 having the amino acid sequence represented by SEQ ID NO: 3, heavy chain CDR2 having the amino acid sequence represented by SEQ ID NO: 4, and heavy chain CDR3 having the amino acid sequence represented by SEQ ID NO: 5 and comprising a light chain variable region comprising light chain CDR1 having the amino acid sequence represented by SEQ ID NO: 12, light chain CDR2 having the amino acid sequence represented by SEQ ID NO: 13 and light chain CDR3 having the amino acid sequence represented by SEQ ID NO: 14;

(2) an antibody comprising a heavy chain variable region comprising heavy chain CDR1 having the amino acid sequence represented by SEQ ID NO: 6, heavy chain CDR2 having the amino acid sequence represented by SEQ ID NO: 7, and heavy chain CDR3 having the amino acid sequence represented by SEQ ID NO: 8 and comprising a light chain variable region comprising light chain CDR1 having the amino acid sequence represented by SEQ ID NO: 15, light chain CDR2 having the amino acid sequence represented by SEQ ID NO: 16 and light chain CDR3 having the amino acid sequence represented by SEQ ID NO: 17;

(3) an antibody comprising a heavy chain variable region comprising heavy chain CDR1 having the amino acid sequence represented by SEQ ID NO: 9, heavy chain CDR2 having the amino acid sequence represented by SEQ ID NO: 10, and heavy chain CDR3 having the amino acid sequence represented by SEQ ID NO: 11 and comprising a light chain variable region comprising light chain CDR1 having the amino acid sequence represented by SEQ ID NO: 18, light chain CDR2 having the amino acid sequence represented by SEQ ID NO: 19 and light chain CDR3 having the amino acid sequence represented by SEQ ID NO: 20; and (4) an antibody binding to the same epitope as that via which any antibody of (1) to (3) binds to the TMPRSS11E protein.

2. The antibody according to claim 1, wherein the antibody has cytotoxic activity.

3. The antibody according to claim 2, wherein the cytotoxic activity is antibody-dependent cellular cytotoxicity (ADCC activity) and/or complement-dependent cytotoxicity (CDC activity).

4. The antibody according to claim 2, wherein the antibody has internalization activity.

5. The antibody according to claim 4, wherein the antibody is conjugated to a cytotoxic substance.

6. The antibody according to any one of claims 2, 3, 4 and 5, wherein the antibody has neutralization activity.

7. A pharmaceutical composition comprising the antibody according to any one of claims 2, 3, 4, 5 and 1 as an active ingredient.

8. The pharmaceutical composition according to claim 7, wherein the pharmaceutical composition is an anticancer agent.

9. The pharmaceutical composition according to claim 8, wherein the anticancer agent targets lung cancer, uterine cervix cancer, or esophagus cancer.

10. A diagnostic drug for cancer comprising the antibody according to any of claims 2, 3, 4, 6 and 1.

11. A pharmaceutical composition comprising the antibody according to claim 6 as an active ingredient.

12. The pharmaceutical composition according to claim 11, wherein the pharmaceutical composition is an anticancer agent.

13. The pharmaceutical composition according to claim 12, wherein the anticancer agent targets lung cancer, uterine cervix cancer, or esophagus cancer.

14. A diagnostic drug for cancer comprising the antibody according to claim 6.

* * * * *